(12) United States Patent
Clarke et al.

(10) Patent No.: US 8,122,849 B2
(45) Date of Patent: Feb. 28, 2012

(54) APPARATUS AND METHOD FOR PRODUCING A PHARMACEUTICAL PRODUCT

(75) Inventors: Allan J. Clarke, Collegeville, PA (US);
David George Doughty, Essex (GB);
Frederick H Fiesser, King of Prussia, PA (US); David Tainsh, Brentford (GB);
Dwight Walker, Research Triangle Park, NC (US); David Wagner, Research Triangle Park, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 1375 days.

(21) Appl. No.: 11/148,894

(22) Filed: Jun. 9, 2005

(65) Prior Publication Data

US 2006/0000470 A1     Jan. 5, 2006

Related U.S. Application Data

(60) Provisional application No. 60/621,992, filed on Oct. 25, 2004, provisional application No. 60/578,245, filed on Jun. 9, 2004.

(51) Int. Cl.
*C23C 16/52* (2006.01)
*B05C 11/10* (2006.01)
*A61K 9/28* (2006.01)

(52) U.S. Cl. ........ 118/668; 118/687; 118/669; 118/674; 118/712; 118/713; 427/2.1; 427/2.14; 427/8; 347/19

(58) Field of Classification Search .......... 427/2.1–2.31, 427/8; 118/665, 688, 708, 712, 714
See application file for complete search history.

(56) References Cited

U.S. PATENT DOCUMENTS

| 3,834,590 | A |   | 9/1974  | Robinson et al. ........ 73/864.17 |
| 3,884,143 | A |   | 5/1975  | Ackley ........................ 101/37 |
| 3,923,207 | A |   | 12/1975 | Kyogoku ................... 222/386 |
| 4,006,578 | A |   | 2/1977  | Gamberini |
| 4,197,289 | A | * | 4/1980  | Sturzenegger et al. ....... 424/443 |
| 4,205,384 | A |   | 5/1980  | Merz et al. |
| 4,257,267 | A |   | 3/1981  | Parsons .................... 73/864.14 |
| 4,322,449 | A | * | 3/1982  | Voss et al. .................... 427/2.14 |
| 4,349,531 | A |   | 9/1982  | Mlodozeniec et al. |
| 4,397,556 | A |   | 8/1983  | Muller |
| 4,408,641 | A |   | 10/1983 | Yamamoto et al. |

(Continued)

FOREIGN PATENT DOCUMENTS

AU    2005254510    6/2005

(Continued)

OTHER PUBLICATIONS

International Search Report dated May 2, 2008 from corresponding PCT/US2005/020319.

(Continued)

*Primary Examiner* — Timothy Meeks
*Assistant Examiner* — Cachet Sellman
(74) *Attorney, Agent, or Firm* — Ohlandt, Greeley, Ruggiero & Perle, LLP

(57) ABSTRACT

An apparatus and method are provided for producing pharmaceutical and pharmaceutical-like products. The apparatus and method provide real-time monitoring of the pharmaceutical product and can provide real-time control. The apparatus and method can monitor the dosage both before and after it has been added to a carrier substrate. The apparatus and method can provide monitoring of each pharmaceutical product that is processed.

22 Claims, 29 Drawing Sheets

U.S. PATENT DOCUMENTS

| | | | |
|---|---|---|---|
| 4,450,877 A | 5/1984 | Walker et al. | |
| 4,485,387 A | 11/1984 | Drumheller | 346/140.1 |
| 4,489,026 A | 12/1984 | Yalkowsky | 264/123 |
| 4,545,412 A | 10/1985 | Gamberini | |
| 4,548,825 A * | 10/1985 | Voss et al. | 426/383 |
| 4,784,582 A | 11/1988 | Howseman | |
| 4,866,906 A | 9/1989 | Tayebi | |
| 4,927,062 A | 5/1990 | Walsh | 222/420 |
| 4,936,828 A | 6/1990 | Chiang | |
| 4,978,859 A | 12/1990 | Karsheim | |
| 5,040,353 A | 8/1991 | Evans et al. | 53/54 |
| 5,085,510 A | 2/1992 | Mitchell | |
| 5,195,656 A | 3/1993 | Briehl et al. | 222/1 |
| 5,223,225 A | 6/1993 | Gautsch | 422/100 |
| 5,278,626 A | 1/1994 | Poole et al. | |
| 5,312,233 A | 5/1994 | Tanny et al. | 417/316 |
| 5,324,359 A | 6/1994 | Cleveland | |
| 5,334,353 A | 8/1994 | Blattner | 422/100 |
| 5,442,892 A | 8/1995 | Burns et al. | 53/53 |
| 5,525,515 A | 6/1996 | Blattner | 436/49 |
| 5,588,963 A | 12/1996 | Roelofs | |
| 5,593,290 A | 1/1997 | Greisch et al. | 417/478 |
| 5,753,302 A | 5/1998 | Sun et al. | |
| 5,799,468 A | 9/1998 | Eck et al. | 53/453 |
| 5,810,988 A | 9/1998 | Smith et al. | 204/666 |
| 5,856,200 A | 1/1999 | Krause et al. | |
| 5,900,634 A | 5/1999 | Soloman | |
| 5,906,682 A * | 5/1999 | Bouras et al. | 118/712 |
| 5,916,524 A | 6/1999 | Tisone | 422/100 |
| 5,964,381 A | 10/1999 | El-Hage et al. | 222/386 |
| 5,973,324 A | 10/1999 | Saby | |
| 5,997,518 A | 12/1999 | Laibovitz et al. | 604/296 |
| 6,063,194 A | 5/2000 | Poliniak et al. | |
| 6,149,815 A | 11/2000 | Sauter | 210/635 |
| 6,159,186 A | 12/2000 | Wickham et al. | |
| 6,176,277 B1 | 1/2001 | Mayer | |
| 6,213,354 B1 * | 4/2001 | Kay | 222/420 |
| 6,220,075 B1 * | 4/2001 | Papen et al. | 73/1.74 |
| 6,345,717 B1 | 2/2002 | Flewitt | 206/531 |
| 6,511,712 B1 * | 1/2003 | Poliniak et al. | 427/466 |
| 6,561,224 B1 | 5/2003 | Cho | 137/827 |
| 6,623,785 B2 | 9/2003 | Childers | 427/2.14 |
| 6,667,802 B2 | 12/2003 | Faus et al. | |
| 6,690,464 B1 | 2/2004 | Lewis et al. | |
| 6,702,894 B2 | 3/2004 | Lee et al. | |
| 6,765,212 B2 | 7/2004 | Goetz et al. | |
| 6,772,801 B1 | 8/2004 | Shojaei et al. | |
| 6,786,579 B2 | 9/2004 | Noolandi et al. | |
| 6,791,688 B2 | 9/2004 | Lai et al. | 356/417 |
| 6,919,556 B1 | 7/2005 | Laurence | |
| 6,946,157 B2 * | 9/2005 | Folestad et al. | 427/2.15 |
| 6,962,715 B2 | 11/2005 | Lee et al. | |
| 7,083,937 B2 | 8/2006 | Sasisekharan et al. | |
| 7,118,010 B2 | 10/2006 | Crowder et al. | |
| 7,154,102 B2 | 12/2006 | Poteet et al. | |
| 7,182,959 B2 | 2/2007 | Martani | |
| 7,247,338 B2 | 7/2007 | Pui et al. | 427/2.14 |
| 2001/0050294 A1 | 12/2001 | Plattner et al. | |
| 2002/0001675 A1 | 1/2002 | Tisone | 427/256 |
| 2002/0034592 A1 | 3/2002 | Hogan | |
| 2002/0079325 A1 * | 6/2002 | Estelle | 222/1 |
| 2002/0081236 A1 | 6/2002 | Bass et al. | 435/6 |
| 2002/0100770 A1 | 8/2002 | Strecker | 222/145.1 |
| 2002/0131998 A1 | 9/2002 | Martani | |
| 2002/0136822 A1 | 9/2002 | Folestad et al. | |
| 2002/0169143 A1 | 11/2002 | Sasisekharan | |
| 2002/0173669 A1 | 11/2002 | Schultz et al. | |
| 2002/0187248 A1 | 12/2002 | Childers | 427/2.1 |
| 2002/0187564 A1 | 12/2002 | Chow et al. | 436/169 |
| 2002/0197388 A1 * | 12/2002 | Brown et al. | 427/2.1 |
| 2003/0008386 A1 | 1/2003 | Bass et al. | 435/6 |
| 2003/0032198 A1 | 2/2003 | Lugmair et al. | 436/180 |
| 2003/0054025 A1 | 3/2003 | Cantor et al. | 424/449 |
| 2003/0065294 A1 | 4/2003 | Pickup et al. | 604/305 |
| 2003/0075106 A1 | 4/2003 | Lee et al. | 118/325 |
| 2003/0077315 A1 | 4/2003 | Lee et al. | 424/439 |
| 2003/0080208 A1 | 5/2003 | Williams et al. | 239/290 |
| 2003/0099708 A1 | 5/2003 | Rowe et al. | |
| 2003/0101991 A1 | 6/2003 | Trueba | 128/200.16 |
| 2003/0143315 A1 | 7/2003 | Pui et al. | |
| 2003/0147952 A1 | 8/2003 | Lim et al. | 424/464 |
| 2003/0175410 A1 | 9/2003 | Campbell et al. | 427/2.24 |
| 2003/0189115 A1 | 10/2003 | Klaseboer et al. | 239/690 |
| 2003/0228242 A1 | 12/2003 | Feygin | 141/234 |
| 2004/0005360 A1 | 1/2004 | Wang et al. | |
| 2004/0028732 A1 | 2/2004 | Falkenhausen et al. | |
| 2004/0081689 A1 | 4/2004 | Danfield et al. | |
| 2004/0099159 A1 | 5/2004 | Volder | |
| 2004/0119795 A1 | 6/2004 | Noolandi et al. | |
| 2004/0135086 A1 | 7/2004 | Lewis et al. | |
| 2004/0137140 A1 | 7/2004 | Childers | |
| 2004/0154534 A1 | 8/2004 | Lee et al. | |
| 2004/0172169 A1 | 9/2004 | Wright et al. | |
| 2004/0231594 A1 * | 11/2004 | Edwards et al. | 118/719 |
| 2004/0241872 A1 * | 12/2004 | Wegrzyn et al. | 436/171 |
| 2004/0256453 A1 | 12/2004 | Lammle | 235/381 |
| 2004/0261700 A1 | 12/2004 | Edwards et al. | |
| 2005/0000422 A1 | 1/2005 | Edwards et al. | |
| 2005/0016451 A1 | 1/2005 | Edwards et al. | |
| 2005/0018036 A1 * | 1/2005 | Barron et al. | 347/224 |
| 2005/0077476 A1 | 4/2005 | Poteet et al. | |
| 2005/0118246 A1 | 6/2005 | Wong et al. | |
| 2005/0129746 A1 | 6/2005 | Lee et al. | |
| 2005/0186253 A1 | 8/2005 | Lee et al. | 424/439 |
| 2005/0199788 A1 | 9/2005 | Lewis et al. | 250/226 |
| 2005/0233000 A1 | 10/2005 | Figueroa et al. | |
| 2005/0238697 A1 | 10/2005 | Chinea et al. | |
| 2005/0257738 A1 | 11/2005 | Tateishi et al. | |
| 2006/0008507 A1 | 1/2006 | Gore | |
| 2006/0018969 A1 | 1/2006 | Figueroa et al. | |
| 2006/0144331 A1 | 7/2006 | Hanafusa et al. | |
| 2006/0156120 A1 | 7/2006 | Kim | |
| 2006/0160238 A1 | 7/2006 | Lemernas | |
| 2006/0172060 A1 | 8/2006 | Teichman et al. | |
| 2006/0184043 A1 | 8/2006 | Tromberg et al. | |
| 2006/0190137 A1 | 8/2006 | Free | |
| 2006/0195270 A1 | 8/2006 | Charlton | |
| 2006/0282223 A1 | 12/2006 | Neil et al. | |
| 2007/0035567 A1 | 2/2007 | Kim et al. | |
| 2007/0056511 A1 | 3/2007 | Childers | |
| 2007/0060564 A1 | 3/2007 | But et al. | |

FOREIGN PATENT DOCUMENTS

| | | |
|---|---|---|
| DE | 2658486 | 6/1978 |
| DE | 2849495 | 5/1980 |
| DE | 3239955 | 5/1984 |
| DE | 3246453 | 6/1984 |
| DE | 4203273 | 8/1992 |
| DE | 2244968 | 8/1993 |
| DE | 19535010 | 3/1997 |
| DE | 19852947 | 5/2000 |
| DE | 19930729 | 1/2001 |
| DE | 19940241 | 3/2001 |
| DE | 19940242 | 3/2001 |
| DE | 19955240 | 5/2001 |
| DE | 10121471 | 11/2002 |
| EP | 11268 | 5/1980 |
| EP | 24230 | 2/1981 |
| EP | 127267 | 12/1984 |
| EP | 224930 | 6/1987 |
| EP | 303025 | 2/1989 |
| EP | 0596328 | 5/1994 |
| EP | 788790 | 8/1997 |
| EP | 810438 | 12/1997 |
| EP | 915014 | 5/1999 |
| EP | 950520 | 10/1999 |
| EP | 1099484 | 5/2001 |
| EP | 1150105 | 10/2001 |
| EP | 1206966 | 5/2002 |
| EP | 1306219 | 5/2003 |
| FR | 2674747 | 10/1992 |
| GB | 310855 | 10/1930 |
| GB | 2377661 | 1/2003 |
| JP | 57179712 | 11/1982 |
| JP | 63177022 | 7/1988 |
| JP | 05124954 | 5/1993 |
| JP | 10264411 | 10/1998 |

| | | |
|---|---|---|
| JP | 11128345 | 5/1999 |
| JP | 11337557 | 12/1999 |
| JP | 2000/042089 | 2/2000 |
| JP | 2000/185106 | 7/2000 |
| JP | 2001/213765 | 8/2001 |
| JP | 2001/232178 | 8/2001 |
| JP | 2004/041464 | 2/2004 |
| TW | 419376 | 1/2001 |
| WO | WO 8301053 | 3/1983 |
| WO | WO 8702241 | 4/1987 |
| WO | WO 8907429 | 8/1989 |
| WO | WO 9222800 | 12/1992 |
| WO | WO 9511007 | 4/1995 |
| WO | WO 9734138 | 9/1997 |
| WO | WO 9744134 | 11/1997 |
| WO | WO 9748384 | 12/1997 |
| WO | WO 9800107 | 1/1998 |
| WO | WO 9820861 | 5/1998 |
| WO | WO 9836738 | 8/1998 |
| WO | WO 9836739 | 8/1998 |
| WO | WO 9843762 | 10/1998 |
| WO | WO 9845205 | 10/1998 |
| WO | WO 9857747 | 12/1998 |
| WO | WO 9911373 | 3/1999 |
| WO | WO 9931468 | 6/1999 |
| WO | WO 9936176 | 7/1999 |
| WO | WO 9965704 | 12/1999 |
| WO | WO 00/33087 | 6/2000 |
| WO | WO 00/41723 | 7/2000 |
| WO | WO 00/45051 | 8/2000 |
| WO | WO 00/56463 | 9/2000 |
| WO | WO 00/65352 | 11/2000 |
| WO | WO 01/07354 | 2/2001 |
| WO | WO 01/12327 | 2/2001 |
| WO | WO 01/30573 | 5/2001 |
| WO | WO 01/50877 | 7/2001 |
| WO | WO 01/64345 | 9/2001 |
| WO | WO 01/87272 | 11/2001 |
| WO | WO 02/03966 | 1/2002 |
| WO | WO 02/28534 | 4/2002 |
| WO | WO 02/37096 | 5/2002 |
| WO | WO 02/38280 | 5/2002 |
| WO | WO 02/40165 | 5/2002 |
| WO | WO 02/40273 | 5/2002 |
| WO | WO 02/43845 | 6/2002 |
| WO | WO 02/055199 | 7/2002 |
| WO | WO 02/082024 | 10/2002 |
| WO | WO 02/085521 | 10/2002 |
| WO | WO 02/097445 | 12/2002 |
| WO | WO 02/102514 | 12/2002 |
| WO | WO 02/102515 | 12/2002 |
| WO | WO 03/006177 | 1/2003 |
| WO | WO 03/016832 | 2/2003 |
| WO | WO 03/023410 | 3/2003 |
| WO | WO 03/023692 | 3/2003 |
| WO | WO 03/024596 | 3/2003 |
| WO | WO 03/037244 | 5/2003 |
| WO | WO 03/037607 | 5/2003 |
| WO | WO 03/037632 | 5/2003 |
| WO | WO 03/041690 | 5/2003 |
| WO | WO 03/048665 | 6/2003 |
| WO | WO 03/053582 | 7/2003 |
| WO | WO 03/092633 | 11/2003 |
| WO | WO 2004/005014 | 1/2004 |
| WO | WO 2004/049466 | 6/2004 |

OTHER PUBLICATIONS

Chiarello, K., Fingerprinting Technology Combats Counterfeit Drugs, Aug. 2004, p. 15, Pharmaceutical Technology (Complete Article).

de Gans et al. Inkjet Printing of Polymers: State of the Art and Future Developments (Review), Feb. 3, 2004, 16(3), pp. 203-213, Advanced Materials (Abstract).

Dhiman, M., Designing of Modified Release Tablets, 2003, vol. 2, pp. 25-30, Indian Pharmacist (Abstract).

Lee et al., Evaluation of Critical Formulation Factors in the Development of a Rapidly Dispersing Captopril Oral Dosage Form, 2003, 29(9), pp. 967-979, Drug Development & Industrial Pharmacy (Abstract).

Meng et al., Polymer MEMS for Micro Fluid Delivery Systems, Sep. 7-11, 2003, Abstracts of Papers, 226th ACS National Meeting, New York, NY, United States (Abstract).

Rowe et al., Theriform Technology, 2003, pp. 77-87, Drugs and the Pharmaceutical Sciences (Abstract).

Yoon et al., A New Process for Making Reservoir-Type Microcapsules Using Ink-Jet Technology and Interfacial Phase Separation, Dec. 5, 2003, 93(2), pp. 161-73, Journal of Controlled Release (Abstract).

Gooray et al., Design of a MEMS Ejector for Printing Applications, Sep.-Oct. 2002, 46(5), pp. 415-421, Journal of Imaging Science & Technology (Abstract).

Griss et al., Expandable Microspheres for the Handling of Liquids, May 2002, vol. 2, No. 2, pp. 117-120, Lab on a Chip (Abstract).

Held, P., The µFILL: A New 96-/384- Wellmicroplate Reagent Dispenser for HTS and Drug Discovery, Jul. 3, 2002, pp. 84, Journal of the Association for Laboratory Automation (Abstract).

Howard et al., Ink-Jet Printer Heads for Ultra-Small-Drop Protien Crystallography, Dec. 2002, 33(6), pp. 1302+, Biotechniques (Abstract).

Kuil et al., Protien Nano-Crystallogenesis, Mar. 13, 2002, 30(3), pp. 262-265, Enzyme and Microbial Technology (Abstract).

Puntambekar et al., Fixed-Volume Metering Microdispenser Module, 2002, 2(4), pp. 213-218, Lab on a Chip (Abstract).

Puntamaker et al., 3-D Microfluidic Networks for Combinational Chemistry, Nov. 3-7, 2002, vol. 1, pp. 422-424, Micro Total Analysis Systems 2002, Proceedings of the TAS 2002 Symposium, 6th, Nara, Japan (Abstract).

Ren et al., Dynamics of Electro-Wetting Droplet Transport, Nov. 15, 2002, vol. B87, No. 1, pp. 201-206, Sensors and Actuators B (Chemical) (Abstract).

Ren et al., Micro/Nano Liter Droplet Formation and Dispensing by Capacitance Metering and Electrowetting Actuation, 2002, pp. 369-372, Proceedings of the 2002 2nd IEEE Conference on Nanotechnology, Piscataway, NJ (Abstract).

Shvets et al., Spot-On Technology for Low Volume Liquid Handling, 2002, 7/6, pp. 125-129, Journal of the Association for Laboratory Automation (Abstract).

Sommer et al., Parallel Immunoassays on Hydrogel TM Biochips Using Microspot Arrays, 2002, vol. 4626, pp. 49-57, Proceedings of the SPIE—The International Society for Optical Engineering (Abstract).

Aoyama et al., Novel Liquid Injection Method With Wedge-Shaped Microchannel on a PDMS Microchip System for Diagnostic Analysis, 2001, vol. 2, pp. 1232-1235, Transducers '01. Eurosensors XV, 11th International Conference on Solid-State Sensors and Actuators. Digest of Technical Papers (Abstract).

Hicks et al., Modification of an Automated Liquid-Handling System for Reagent-Jet, Nanoliter-Level Dispensing, Apr. 2001, 30(4), pp. 878-885, BioTechniques (Abstract).

Ikemoto et al., A Head-Attachable Device for Injecting Nanoliter Volume of Drug Solutions Into Brain Sites of Freely Moving Rats, Sep. 30, 2001, 110/1-2, pp. 135-140, Journal of Neuroscience Methods (Abstract).

Koltay et al., Microdispenser Array for Highly Parallel and Accurate Liquid Handling, 2001, vol. 4590, pp. 195-203, Proceedings of SPIE—The International Society for Optical Engineering (Abstract).

Meldrum et al., Automated, Integrated Modules for Fluid Handling, Thermal Cycling and Purification of DNA Samples for High Throughput Sequencing and Analysis, 2001, vol. 2, pp. 1211-1219, 2001 IEEE/ASME International Conference on Advanced Intelligent Mechatronics, Piscataway, NJ (Abstract).

Pearson et al., Microfabrication and Application of Reservoir Pins for Liquid Transfer in Biotechnology, vol. 4407, pp. 281-294, Proceedings of the SPIE—The International Society for Optical Engineering (Abstract).

Pearson et al., Microfluidic Study of the Liquid Transfer Properties of the Liquid Transfer Properties of Reservoir Pins for Use in Microarraying, 2001, vol. 4560, pp. 189-195, Proceedings of SPIE—The International Society for Optical Engineering (Abstract).

Puntambekar et al., A New Fixed-Volume Meteringmicrodispenser Module Based on SPROMS Technology, 2001, vol. 2, pp. 1240-1243, Transducers '01. Eurosensors XV. 11th International Conference on Solid-State Sensors and Actuators. Digest of Technical Papers (Abstract).

Bohm et al., Closed-Loop Controlled Electrochemically Actuated Micro-Dosing System, Dec. 2000, vol. 10, No. 4, pp. 498-504, Journal of Micromechanics and Microengineering (Abstract).

Ducree et al., Production System for Biochips, 2000, vol. 2, pp. 529-533, Proceedings. MICRO. Tec. 2000. VDE World Microtechnologies Congress, Berlin, Germany: VDE Verlag (Abstract).

Katstra et al., Controlling Drug Placement During the Fabrication of Complex Release Oral Forms Using 3DP, 2000, pp. 413-414, Proceedings of the International Symposium on Controlled Release of Bioactive Materials (Abstract).

Katstra et al., Engineering of Complex Oral Delivery Devices Using Three Dimensional Printing, 2000, vol. 28, Supplement 1, pp. S-22, Annals of Biomedical Engineering (Abstract).

Katstra et al., Oral Dosage Forms Fabricated by Three Dimensional Printing, May 3, 2000, 66(1), pp. 1-9, Journal of Controlled Release (Abstract).

Kido et al., Disc-Based Immunoassay Microarrays, May 2000, 411(1-2), pp. 1-11, Analytica Chimica Acta (Abstract).

Meldrum et al., Acapella-1K, A Capillary-Based Submicroliter Automated Fluid Handling System for Genome Analysis, Jan. 2000, 10(1), pp. 95-104, Genome Research (Abstract).

Rowe et al., Multimechanism Oral Dosage Forms Fabricated by Three Dimensional Printing, May 3, 2000, 66(1), 11-7, Journal of Controlled Release (Abstract).

Sastry et al., Recent Technological Advances in Oral Drug Delivery—A Review, Apr. 1, 2000, 3 / 4, pp. 138-145, Pharmaceutical Science and Technology Today (Abstract).

Katstra et al., Pulsatory Oral Drug Delivery Devices Fabricated by Three Dimensional Printing, 1999, 26th, pp. 167-168, Proceedings of the International Symposium on Controlled Release of Bioactive Materials (Abstract).

Boillat et al., Controlled Liquid Dosing in Micro-Instruments, 1999, vol. 3877, pp. 20-27 Proceedings of the SPIE—The International Society for Optical Engineering (Abstract).

Meyer et al., Liquid Handling in the Pico- and Nanoliter Range, Apr. 18-21, 1999, pp. 312-319, Microreaction Technology: Industrial Prospects, Proceedings of the International Conference on Microreaction Technology, 3rd, Frankfurt (Abstract).

Dilhan et al., Experimentation of an Electrostatically Actuated Monochip Micropump for Drug Delivery; 1999, vol. 3680, pt. 1-2, pp. 887-896, Proceedings of the SPIE—The International Society for Optical Engineering (Abstract).

Meldrum etal., Acapella, A Capillary-Based Submicroliter Automated Sample Preparation System for Genome Analysis, 1999, pp. 39-48, 1999 IEEE/ASME International Conference on Advanced Intelligent Mechatronics, Piscataway, NJ, United States: IEEE (Abstract).

Amacker et al., Passive Micro-Flow Regulator for Drug Delivery System, 1998, vol. 1, pp. 591-594, Eurosensors XII. Proceedings of the 12th European Conference on Solid-State Tranducers and the 9th UK Conference on Sensors and their Applications (Abstract).

Backofen et al., Capillary Batch Injection Analysis: A Novel Approach for Analyzing Nanoliter Samples, May 4, 1998, 362/2-3, pp. 213-220, Analytica Chimica Acta (Abstract).

Delamarche et al., Microfluidic Networks for Chemical Patterning of Substrates: Design and Application to Bioassays, Jan. 28, 1998, 120/3, pp. 500-508, Journal of the American Chemical Society (Abstract).

Driscolli et al., Multiprobe NL Components Drug Discovery Assay Miniaturization, Fall 1998, vol. 3, No. 3, pp. 237-239, Journal of Biomolecular Screening (Abstract).

Fernandes, P.B., Technological Advances in High-Throughput Screening, Oct. 1998, 2(5), pp. 597-603, Current Opinion in Chemical Biology (Abstract).

Katstra et al., Oral Dosage Forms by Three Dimensional Printing, 1998, 25th, pp. 760-761, Proceedings of the International Symposium on Controlled Release of Bioactive Materials (Abstract).

Lemmo et al., Inkjet Dispensing Technology: Applications in Drug Discovery, Dec. 1998, 9(6), pp. 615-617, Current Opinion in Biotechnology (Abstract).

Stevens et al., Comparison of Automationequiptment in High Throughput Screening, 1998, 3(4), pp. 305-311, Journal of Biomolecular Screening (Abstract).

Fiehn et al., New Technology for the Precision Dosage of Liquids in the Range of Microlitres and Submicrolitres [in German], 1997, 59/9, pp. 814-817, Pharmazeutische (Abstract).

Houston et al., The Chemical-Biological Interface: Developments in Automated and Miniaturised Screening Technology, Dec. 1997, 8(6), pp. 734-740, Current Opinion in Biotechnology (Abstract).

Skardon, J., Applications for Microfluidic Components, 1997, pp. 330-333, WESCON/97. Conference Proceedings, New York, NY, United States:IEEE (Abstract).

Benjamin et al., Solid-Free Form Fabrication of Drug Delivery Devices, vol. 40, No. 1-2, pp. 77-87, Journal of Controlled Release (Abstract).

Fiehn et al., New Technologies for High Precision Dosage, 1996, No. 176, IEE Colloquium (Digest) (Abstract).

Kaartinen, N., Micro Electro Thermo Fluidic (METF) Liquid Microprocessor, 1996, pp. 395-399, Proceedings of the IEEE Micro Electro Mechanical Systems (MEMS), Piscataway, NJ, United States (Abstract).

Stanchfield et al., Precision 96-Channel Dispenser for Microchemical Techniques, 1996, 20(2), pp. 292-296, BioTechniques (Abstract).

Zen'ichi, Y., Utilization of Antibacterial Agent by Thermo-Transfer Printing, 1995, No. 533, pp. 24-26, Sangyo Kikai (Abstract).

Hogan, B., Adhesive Dispenser Provides Plus or Minus 2% Volume Repeatability, Apr. 11, 1994, vol. 49, No. 7, Design News (Boston) (Abstract).

Lammerink et al., Integrated Micro-Liquid Dosing System, 1993, pp. 254-259, Proceedings, IEEE. Micro Electro Mechanical Systems. An Investigation of Micro Structures, Sensors, Actuators, Machines and Systems, New York, NY, United States (Abstract).

Schober et al., Accurate High-Speed Liquid Handling of Very Small Biological Samples, Aug. 1993, 15(2), pp. 324-329, BioTechniques (Abstract).

Bernardini et al., Applications of Piezoelectric Fluid Jetting Devices to Neuroscience Research, Jun. 1991, 38(1), pp. 81-88, Journal of Neuroscience Methods (Abstract).

Martin et al., Automatic Manipulation of Microlitre Volumes of Liquid Reagents, Jan. 1987, vol. 20, No. 1, pp. 22-26, Journal of Physics E (Scientific Instruments) (Abstract).

Kahl et al., General Purpose Multichannel Micro-Dispensing Device, 1976, 48(4), pp. 789-790, Analytical Chemistry (Abstract).

"Online Quality Control with Raman Spectroscopy in Pharmaceutical Tablet Manufacturing," Bonawi-Tan, Winston; Williams, Julie Ann Stuart, Journal of Manufacturing Systems v23n4 pp. 299-308, 2004.

"Photonic analysis creeps toward the production line," Weiss, Stephanie A., Photonics Spectra, v28, n10, p. 98(2), Oct. 1994.

English translation of Examination Report dated Feb. 25, 2010 for corresponding Patent Application No. 509/2005 in Pakistan.

Supplementary European Search Report dated Aug. 17, 2011 for European application No. 05760236.

Malaysian Search Report dated Sep. 11, 2011 for Malaysian application No. PI 20052606.

Australian Examination Report dated Oct. 27, 2011 for Australian application No. 2011204848.

Australian Examination Report dated Oct. 28, 2011 for Australian application No. 2011204851.

* cited by examiner

Luminescence Imaging Results

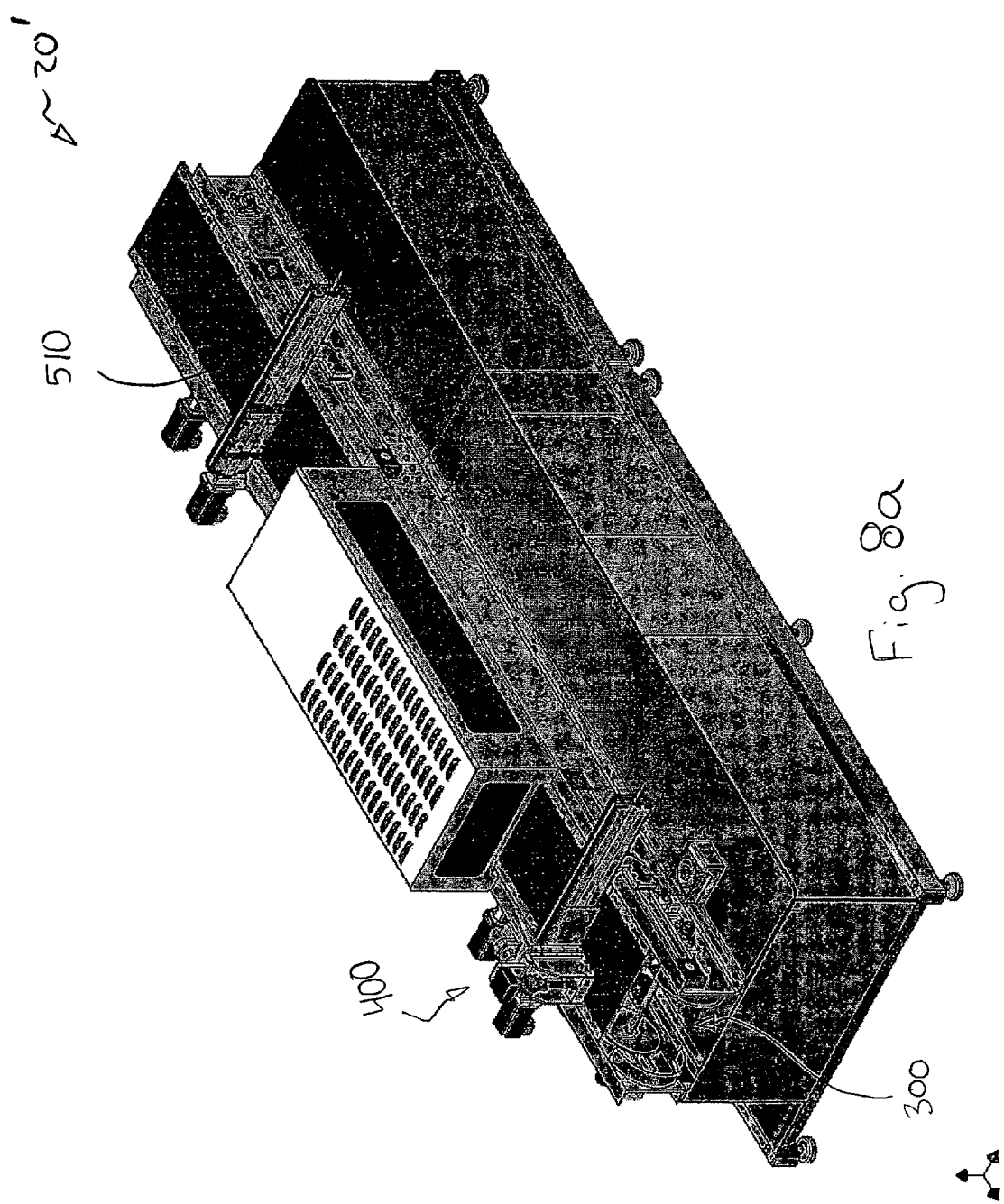

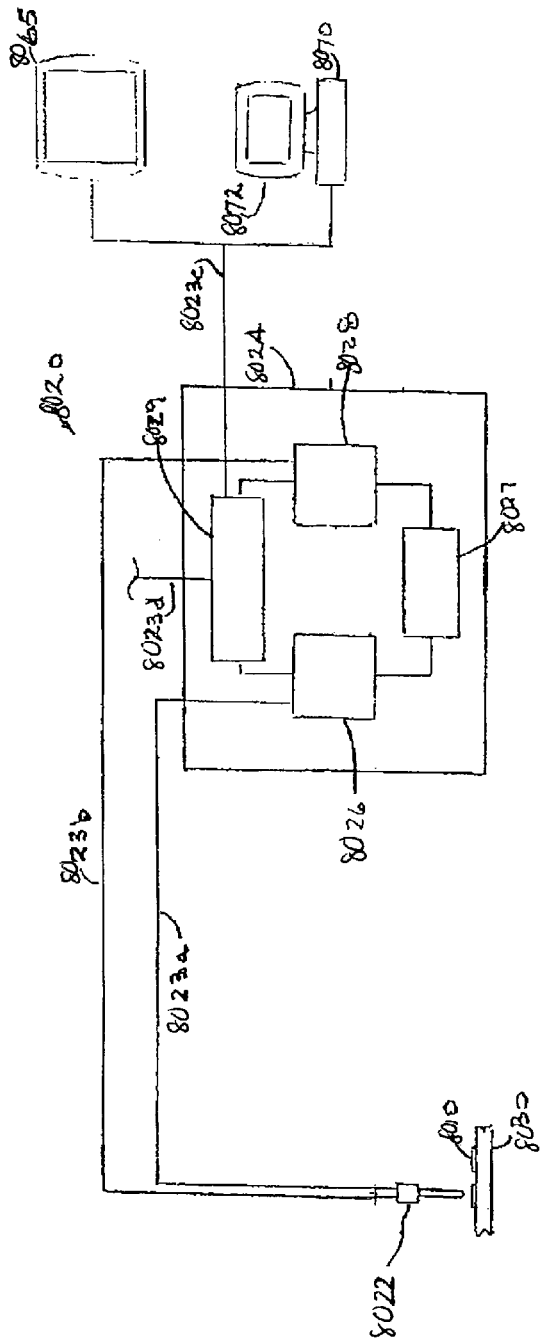
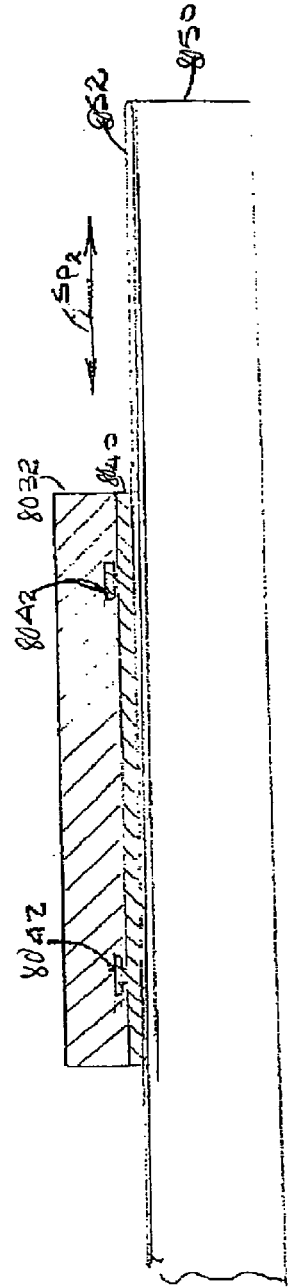
Fig. 8o
Fig. 8n

APPARATUS AND METHOD FOR PRODUCING A PHARMACEUTICAL PRODUCT

RELATED APPLICATIONS

This application is related to, and claims priority in, co-pending U.S. Provisional Application Ser. No. 60/621,992, filed Oct. 25, 2004, the disclosure of which is incorporated herein by reference. This application is also related to, and claims priority in, co-pending U.S. Provisional Application Ser. No. 60/578,245, filed Jun. 9, 2004, the disclosure of which is incorporated herein by reference.

BACKGROUND OF THE INVENTION

1. Field of the Invention

The present invention relates to the manufacture of pharmaceutical and pharmaceutical-like product. More particularly, the present invention relates to an apparatus and process for manufacturing pharmaceutical and pharmaceutical-like product.

2. Description of Related Art

Contemporary quality control methods for pharmaceutical and pharmaceutical-like product involve the use of batch-sampling techniques. The batch-sampling techniques test samples from batches of the product, such as through the use of wet chemistry, after the product has been made. Contemporary batch sampling techniques use frequent and sometimes random batch sampling for various characteristics of the final product, such as, for example, quality, concentration and homogeneity. However, these batch-sampling techniques suffer from drawbacks because of their inefficiency and inaccuracy.

Batch-sampling assumes that all of the product attributes in a particular batch are normally distributed and have the same or very similar characteristics as the sampled product from the batch. Where the chosen samples do not meet the required tolerances, an entire batch can be discarded or re-processed for additional sampling and testing. If the chosen unacceptable samples do not have the same characteristics as other acceptable product in the batch, then acceptable product may be discarded along with the rejected samples or at least need to undergo more costly testing. Batch-sampling can be particularly inaccurate where the error or flaw in the process is random, non-repeating or of a non-linear nature. Such flaws or errors in the manufacturing process may provide for only a fraction of the product of the batch being unacceptable but result in an entire batch being discarded or re-tested, as a result of the use of batch sampling.

Another significant drawback of batch-sampling techniques is where the chosen samples meet the required tolerances, but where a fraction of the batch is actually unacceptable and not representative of the tested sample. In such a situation, unacceptable product may be provided to the consumer because of the inherent flaw in the quality control method.

An additional drawback in batch-sampling techniques is that the testing is done at the end of the process and provides little, if any, information for corrective action to be taken with regard to the manufacturing process and its various steps. The batch-sampling technique can provide overall information for sampled product, but does not indicate at which point or which particular step in the process that a flaw is occurring, such as, for example, inadequate dosing or detrimental heating.

Another drawback of batch-sampling technique is that it is done off-line of the manufacturing process, which adds time to the overall manufacturing process, and can also be labor intensive. The cost in time and labor is increased where more stringent standards are applied to a particular product so the batch-sampling technique utilizes a higher portion of samples for testing.

Contemporary tablet manufacturing methods use wet granulation and direct compression approaches to add the active ingredient into the tablet ingredients. After mixing to achieve homogeneity, tablets are produced, which are each intended to have the required dosage of active ingredient. These types of contemporary batch manufacturing techniques suffer from drawbacks due to their inefficiency and inaccuracy.

Contemporary batch production attempts to homogeneously mix and equally distribute the active ingredient to each of the tablets in the batch. When the active ingredient in the batch is not equally distributed, such as, for example, an unacceptable concentration, the non-homogeneity of the active ingredient will be distributed throughout the entire batch rendering all of the tablets unacceptable. Additionally, inadequate mixing in other ingredients will be distributed throughout the entire batch rather than just to individual tablets.

Contemporary machines that manufacture pharmaceutical product suffer from the drawback of having a large footprint. These machines may be broken into a number of different units that handle different steps of the process. The use of separate units adds labor and time to the process, such as, for example, requiring the product to be moved between different machines.

In addition, the pharmaceutical product is usually stored for days awaiting availability of process machinery for the next manufacturing step. This delay increases production time and increases manufacturing costs.

Contemporary machines and techniques also require a longer time and added labor to change-over to different products, if the machine is capable of doing so at all. To produce a different pharmaceutical product, these contemporary machines require thorough cleaning of the components to avoid contamination of the next batch from the previous production ingredients.

Accordingly, there is a need for an apparatus and process for manufacturing pharmaceutical and pharmaceutical-like products that reduce or eliminate these manufacturing and quality control drawbacks of the contemporary devices and techniques.

SUMMARY OF THE INVENTION

It is an object of the present invention to provide a more efficient process and/or apparatus for manufacturing pharmaceutical and pharmaceutical-like products.

It is another object of the present invention to provide such a process and/or apparatus that provides real-time process monitoring.

It is yet another object of the present invention to provide such a process and/or apparatus that provides real-time feedback and control of the process and product quality.

It is still another object of the present invention to provide such a process and/or apparatus that provides monitoring of each of the product that is manufactured.

It is yet still another object of the present invention to provide such a process and/or apparatus that minimizes or eliminates off-line quality control inspection and facilitates real-time release of the product.

It is a further object of the present invention to provide such a process and/or apparatus that produces a pharmaceutical product that allows for the use of various forms of spectroscopy or chemical imaging to monitor the dose.

It is still a further object of the present invention to provide such a process and/or apparatus that eliminates product with an incorrect dose.

It is yet a further object of the present invention to provide such a process and/or apparatus that facilitates change over to a production of a different product.

It is a further object of the present invention to provide such a process and/or apparatus that enhances stability by reducing excipient interaction with the active pharmaceutical ingredient (API).

It is yet another further object of the present invention to provide a process and/or apparatus that employs Process Analytical Technology to improve the manufacture of pharmaceutical product.

These and other objects and advantages of the present invention are provided by an apparatus for producing pharmaceutical product that each has a carrier substrate and a dosage of active agent. The apparatus has a dispensing system that adds the dosage of active agent to each of the carrier substrates and a dosage monitoring system that determines the dosage of active agent for each of the pharmaceutical product.

In another aspect, a monitoring system for a pharmaceutical machine is provided. The pharmaceutical machine produces pharmaceutical product that each has a carrier substrate and a dosage of active agent. The monitoring system has a dose inspection system operably connected to the pharmaceutical machine. The dose inspection system determines an amount of the dosage of active agent that will be added to each of the carrier substrates by the pharmaceutical machine.

In another aspect, an apparatus for producing pharmaceutical product that each has a carrier substrate and a dosage of active agent is provided. The apparatus has a dispensing system that adds the dosage of active agent to each of the carrier substrates. The apparatus further has a dosage confirmation system that performs real-time monitoring of the liquid dispensing system to determine a volume of the dosing liquid containing active agent for the pharmaceutical product.

In another aspect, a method of producing pharmaceutical product is provided. The method includes, but is not limited to, providing a plurality of carrier substrates; providing a dosage of active agent for each of the plurality of carrier substrates; adding the dosage of active agent to each of the plurality of carrier substrates; and determining volume of the dosing liquid containing the active agent for each of the pharmaceutical product.

In another aspect, a method of providing quality control for a pharmaceutical machine is provided. The method includes, but is not limited to, determining an amount of a dosage of active agent that is being added to each of a plurality of carrier substrates that is processed by the pharmaceutical machine.

In another aspect, a method for producing pharmaceutical product is provided. The method includes, but is not limited to, providing a plurality of carrier substrates, providing a dosage of active agent for each of the plurality of carrier substrates, adding the dosage of active agent to each of the plurality of carrier substrates, and performing real-time monitoring of the adding of the dosage of active agent to determine the amount of active agent for the pharmaceutical product.

In another aspect, a monitoring system, pharmaceutical machine or method of quality control is provided wherein optical profilometry is performed on each of a plurality of carrier substrates to determine the amount of dosage of active agent that has been dispensed thereon.

In another aspect, an apparatus or method is provided for producing a batch of pharmaceutical product that each has a carrier substrate and a dosage of active agent. The apparatus has a dispensing module that dispenses the dosage onto each of the carrier substrates with a content uniformity for the batch of less than 5% relative standard deviation (RSD), and preferably less than 2% RSD, for a dosage of less than 5 mg. Also, the dispensing module dispenses the dosage onto each of the carrier substrates with a content uniformity for the batch of less than 2% RSD for a dosage of less than 10 mg.

The dosage monitoring system can have a dose inspection system that determines the amount of the dosage of active agent that is being added to each of the carrier substrates by the dispensing system. Each of the carrier substrates can move continually along the apparatus as the dose inspection system determines the amount of the dosage of active agent. The dispensing system may dispense the dosage of active agent as a liquid droplet.

The dose inspection system can have a camera or video/digital recording device (herein referred to as "camera") and a flow cell. The dose inspection system may also have a trigger operably connected to the camera. The trigger can actuate the camera to obtain an image of the droplet in-flight.

The apparatus or pharmaceutical machine can have a holding member that holds each of the carrier substrates and a conveyor that moves the holding member along the apparatus. The holding member may move continually along the apparatus as the dose inspection system determines the amount of the dosage of active agent that is being applied to the tablet. The dose inspection system can obtain an image of the droplet in-flight and determine the amount of the dosage of active agent that will be added to each of the carrier substrates. This dose measurement system obtains a video image of the droplet containing the active agent and calculates the droplet volume with image analysis software.

The dosage monitoring system can have a dose confirmation system that determines the amount of the dosage of active agent that has been added to each of the carrier substrates by the dispensing system after the liquid has evaporated, and performs spectroscopy or chemical imaging on each of the carrier substrates to determine the amount of the dosage of active agent. The spectroscopy may be near-infrared, mid-infrared, ultraviolet/visible, fluorescence, laser induced fluorescence, luminescence, Raman, terahertz, or any combinations thereof.

The dose confirmation system can also have a second camera that obtains an image the amount of the dosage of active agent applied to the tablet after the liquid has evaporated for each of the carrier substrates. A position of the dosage on each of the carrier substrates may be determined based on the imaging system. Each of the carrier substrates can continue to move along the apparatus as the camera obtains the image of the dosage of active agent applied to the tablet after the liquid has evaporated.

The apparatus or pharmaceutical machine may also have a drying system with drying monitors. The drying system can dry the dosage of active agent on each of the carrier substrates and the drying monitors can obtain drying conditions for the carrier substrates. The drying conditions may include temperature, air-flow rate, humidity, surface temperature of the carrier substrates, or any combinations thereof.

The apparatus or pharmaceutical machine can have a printing system that applies an identification marker to each of the carrier substrates and a third camera that obtains a third image of the identification marker for inspection and quality control.

Each of the carrier substrates may continue to move along the apparatus as the third camera obtains the third image.

The apparatus may also have a holding member, a conveyor and a fourth camera. The holding member holds each of the carrier substrates. The conveyor moves the holding member along the apparatus. The fourth camera obtains an image of each of the carrier substrates for inspection and quality control. The image is obtained prior to the liquid dispensing system adding the dosage of active agent to each of the carrier substrates, such as, for example, to verify that each of the carrier substrates are free of defects, e.g., cracked, chipped or partial tablets.

The apparatus or pharmaceutical machine may also have a dosage inspection system that performs real-time monitoring of the dispensing system to determine the amount of the dosage of active agent that will be added to each of the carrier substrates. The apparatus can have a control system that performs real-time control of the dispensing system based at least in part on the real-time monitoring. The real-time control can include adjusting the amount of the dosage of active agent that will be added to each of the carrier substrates. The real-time control can also include adjusting a position of the dosage of active agent added to each of the carrier substrates.

The apparatus may also have a flow-cell in the product supply line where the dosing liquid is being provided to the dispensing system. The flow-cell may utilize one or more spectrographic techniques or other techniques to measure the concentration of active agent in the dosing liquid. The spectrographic technique verifies that the correct concentration is maintained throughout the process and, when monitored in conjunction with the volume measurement of the applied liquid droplets, will assure the correct amount of active agent is delivered to the carrier substrate.

The spectrographic techniques may include, but are not limited to, ultraviolet light, visible light, laser induce fluorescence, luminescence, near-infrared, mid-infrared, terahertz or Raman. The flow-cell design can utilize transmission, diffuse reflectance, attenuated total reflection approaches of detection or other techniques. Where needed, multivariant statistical or chemometric approaches can be applied to enhance the detection technique or to compensate for process variability.

This application is related to the following applications which have been filed contemporaneously herewith and the disclosures of which are hereby incorporated by reference in their entirety: APPARATUS AND METHOD FOR PHARMACEUTICAL PRODUCTION, PHARMACEUTICAL PRODUCT, APPARATUS AND METHOD FOR PRODUCING OR PROCESSING A PRODUCT OR SAMPLE, APPARATUS FOR PRODUCING A PHARMACEUTICAL PRODUCT, and METHOD FOR PRODUCING A PHARMACEUTICAL PRODUCT.

Other and further objects, advantages and features of the present invention will be understood by reference to the following:

BRIEF DESCRIPTION OF THE DRAWINGS

FIG. 8a is a perspective view of another alternative embodiment of a pharmaceutical manufacturing machine of the present invention;

FIG. 8d is a perspective, assembly view of the transport system for the spectroscopic detection system of FIG. 8b;

FIG. 8n is a partial sectioned, side plan view of the transport system assembly of FIG. 8d;

FIG. 8o is a schematic illustration of the spectroscopic detection system of FIG. 8b with associated display means;

DETAILED DESCRIPTION OF THE INVENTION

Figure 1:
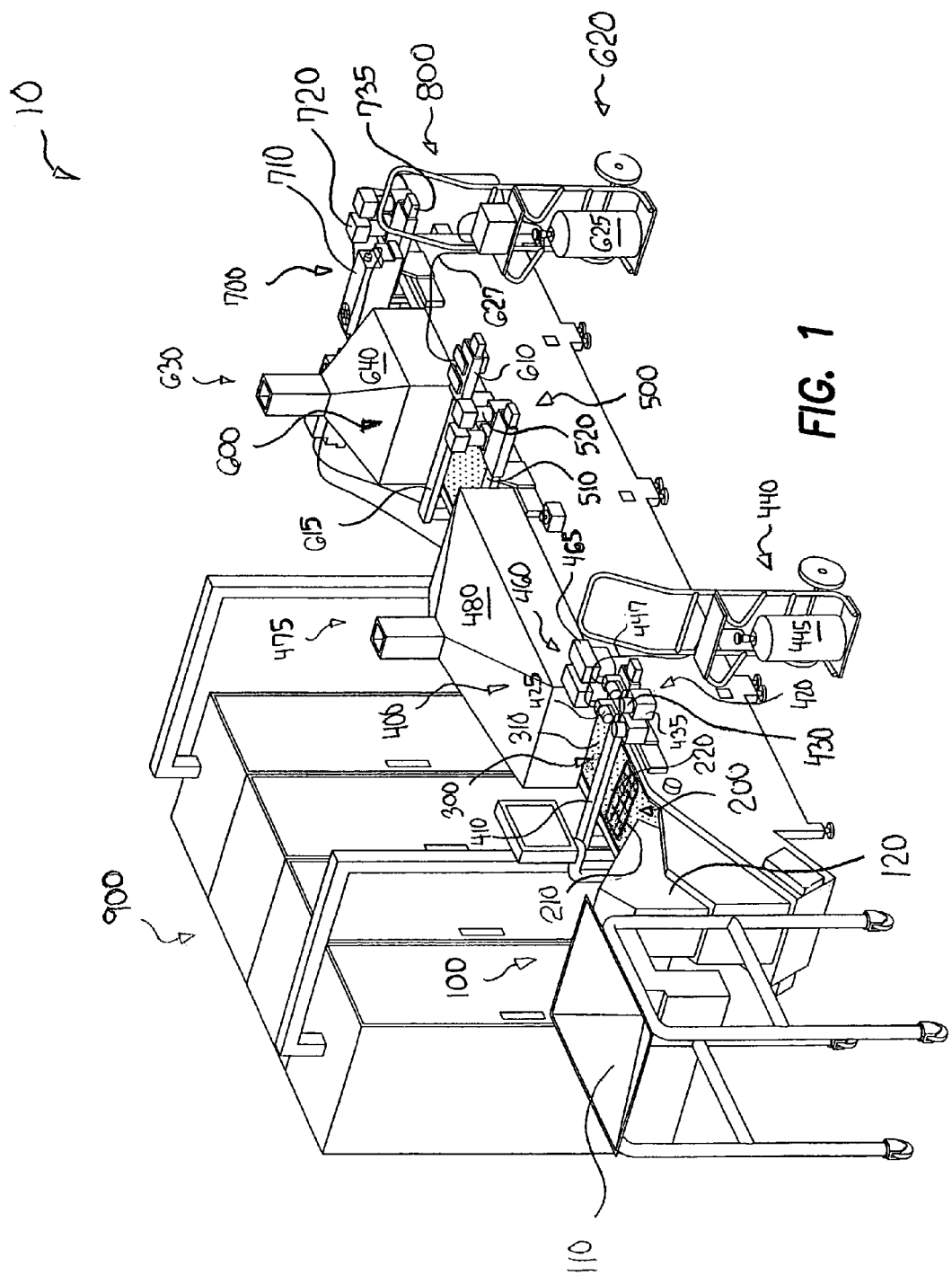
FIG. 1 is a perspective view of a preferred embodiment of a pharmaceutical manufacturing machine of the present invention.
Figure 2:
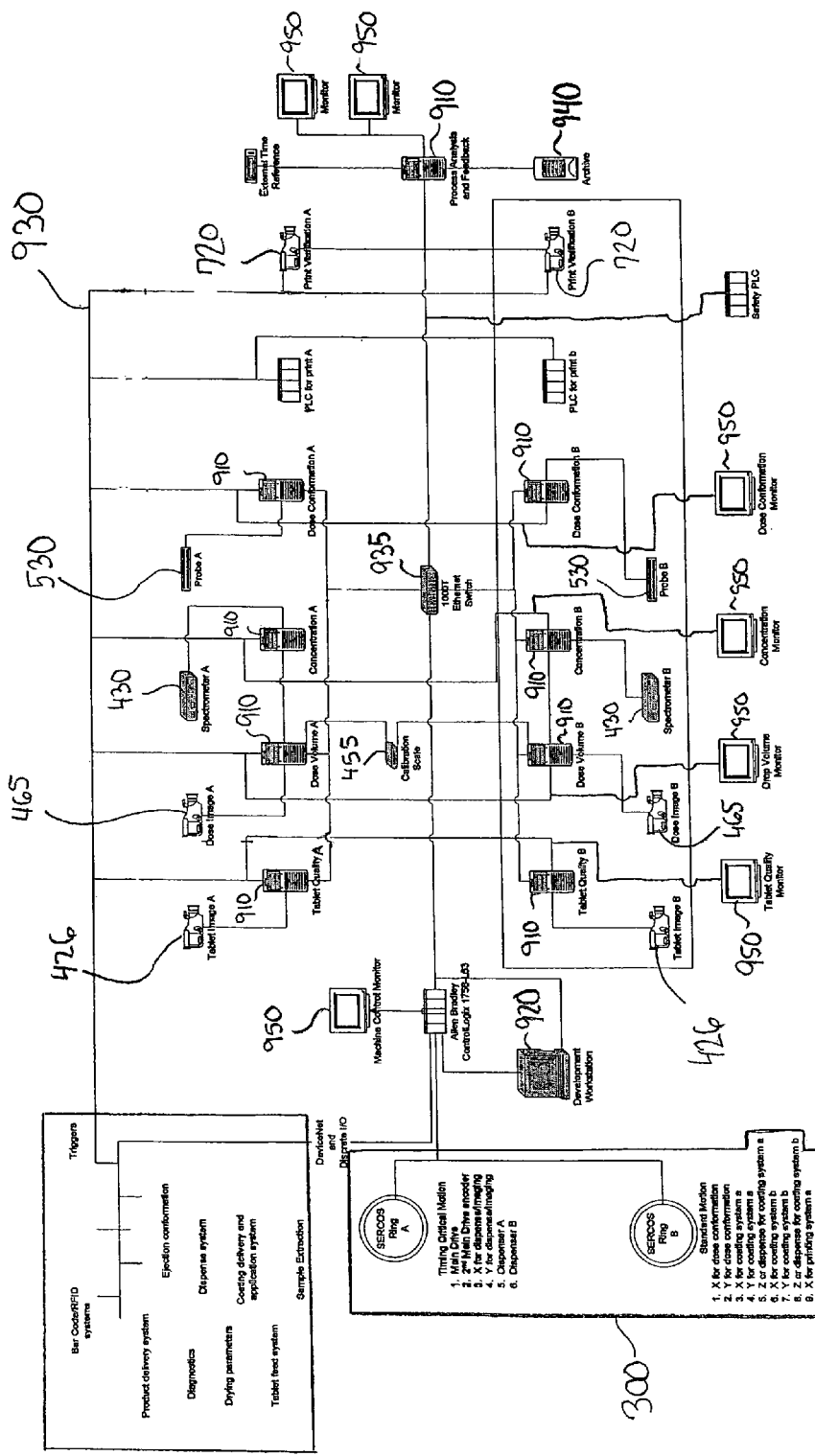
FIG. 2 is a schematic representation of the automation components of the pharmaceutical manufacturing machine of FIG. 1.
Figure 3:
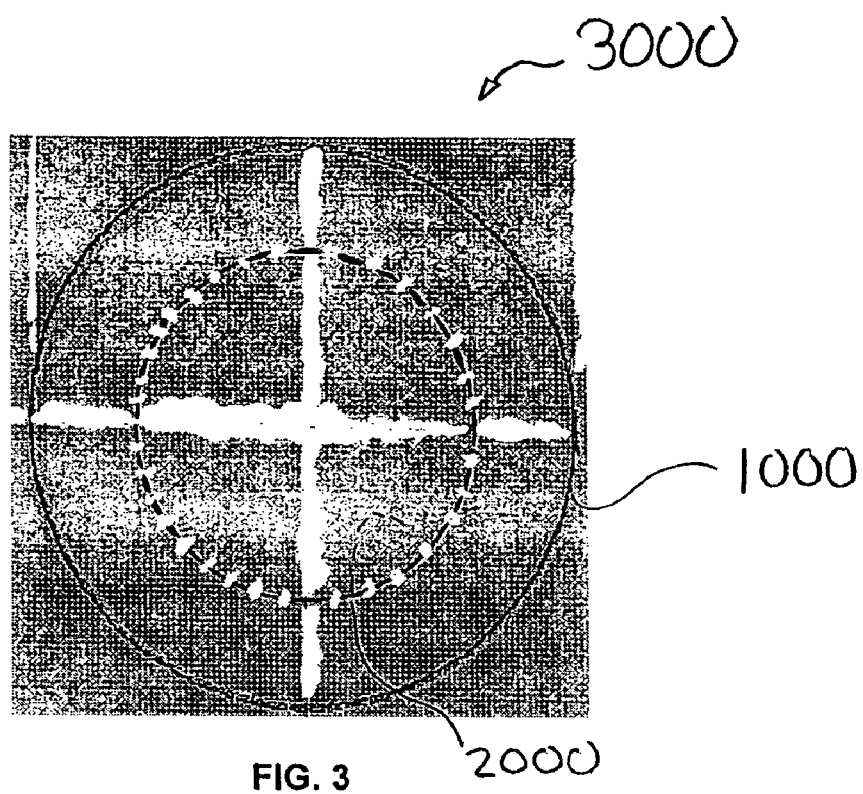
FIG. 3 is a plan view of a pharmaceutical product manufactured by the machine of FIG. 1.

Referring to the drawings, and in particular FIGS. 1 through 3, a preferred embodiment of the pharmaceutical manufacturing apparatus or machine of the present invention is shown and generally referred to by reference numeral 10. The machine 10 has a plurality of components that are operably connected to manufacture a pharmaceutical product 3000 and preferably a batch of pharmaceutical product, as will be described later in greater detail. A batch of pharmaceutical product 3000 is a quantity of product, which has been produced during a defined cycle of manufacture, such as, for example, a fixed number or one or more runs over a fixed time period. The machine 10 has various components arranged along a straight or substantially straight line. However, the present invention contemplates other arrangements and positionings of the various components, such as, for example, in circular or rectangular paths.

The arrangement and positioning of the components of machine 10 provide a smaller footprint for space savings, as well as providing a more efficient and ergonomic machine that facilitates operation. Machine 10 can have components stacked on each other or at differing heights to take advantage of vertical space, as well as facilitating operation, such as, for example, enabling the use of gravity in the process performed by the machine.

The machine 10 has a loading system 100, a holding system 200, a conveyor system 300, a drug dispensing system 400, a coating system 600, a printing system 700, a product acception-rejection system 800, and a control system 900. Each of these systems 100 through 900 are operably connected to each other to efficiently and ergonomically provide pharmaceutical product 3000 that is ready for packaging, and which have each undergone real-time monitoring, and preferably real-time feedback and adjustment or control.

Figure 4:
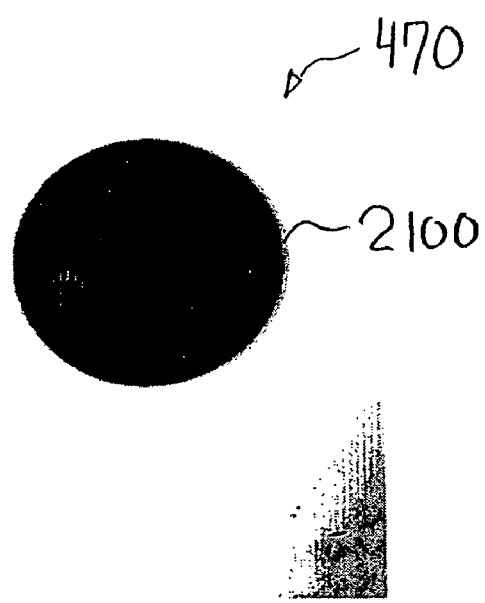
FIG. 4 is a high speed video image of a dose droplet dispensed by the pharmaceutical manufacturing machine of FIG. 1.

The machine 10 delivers the pharmaceutical product 3000, which is a combination of a carrier tablet or other substrate 1000 and a liquid dose 2000, as shown in FIG. 3. As will be described later in greater detail, the liquid dose 2000 is dispensed by drug dispensing system 400 in the form of a dose droplet 2100 (shown in FIG. 4) that is dispensed onto the carrier tablet 1000. It should be understood that the liquid dose 2000 can have a variety of properties, such as, for example, low-viscosity, high-viscosity, solution or suspension, such that the term liquid is not intended to be limiting.

The liquid dose 2000 has an active, active agent or therapeutic active agent, and is capable of being dispensed by the machine 10 onto the carrier tablet 1000. The terms active, active agent or therapeutic active agent include, but are not limited to, drugs, proteins, peptides, nucleic acids, nutritional agents, as described herein. These terms include pharmaceutically acceptable agents, bioactive agents, active agents, therapeutic agents, therapeutic proteins, diagnostic agents, or drug(s) as defined herein, and follows the guidelines from the European Union Guide to Good Manufacturing Practice. Such substances are intended to furnish pharmacological activity or other direct effect in the diagnosis, cure, mitigation, treatment, or prevention of disease or to affect the structure and function of the body. The substance may also include a diagnostic agent, such as an imaging agent and/or a radioactive labeled compound. Their use may be in a mammal, or may be in a human. The pharmacological activity may be prophylactic, or for treatment of a disease state. The agents herein include both small molecule therapeutics, as well as peptides and proteins. The pharmaceutical compositions described herein may optionally comprise one or more pharmaceutically acceptable active agent, bioactive agent, active agent, therapeutic agent, therapeutic protein, diagnostic agent, or drug(s) or ingredients distributed within.

It should further be understood that the present invention is not intended to be limited to the use of any particular active agents, formulations or resulting pharmaceutical or pharmaceutical-like product. The liquid dose 2000 can be a solution or suspension; and the resulting pharmaceutical or pharmaceutical-like product can be immediate release, slow release, or controlled release. The liquid dose 2000 can be aqueous, non-aqueous or mixtures thereof. Non-aqueous solutions or suspensions include, but are not limited to, organic solvents, propellants, liquefied gases, volatile silicons, or any combinations thereof. The terms pharmaceutical or pharmaceutical-like product are also not intended to be limiting. The present invention contemplates the use of any active agents and/or combinations of active agents that are suited for dispensing by the machine 10.

Figure 12:
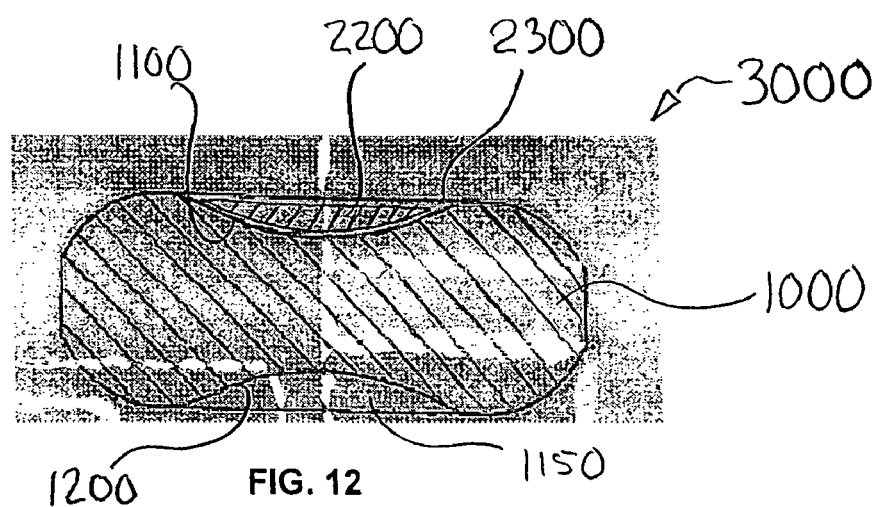
FIG. 12 is a cross-sectional view of the carrier tablet of FIG. 11 taken along line 12-12 of FIG. 11 with a dose droplet.

Dose droplet 2100 preferably forms a film 2200 upon the outer surface 1100 or substantially along the outer surface of the carrier tablet 1000 (shown in FIG. 12). As will be described later, the liquid dose 2000 is preferably heated so that excess amounts of liquid are evaporated and the active agent becomes captured in the film 2200. The carrier tablet 1000, the liquid dose 2000 and resulting pharmaceutical product 3000 undergo real-time monitoring, feedback and adjustment, which improves quality control.

In the preferred embodiment shown in FIG. 1, loading system 100 has a loading container or hopper 110 in communication with a loading chute 120. Hopper 110 is preferably movable so that carrier tablets 1000 can be loaded into the hopper and then the hopper can be moved into communication with the loading chute 120. Loading chute 120 is in communication with holding system 200 and conveyor system 300 so that the carrier tablets 1000 can be moved from the hopper 110 into the holding system 200 for movement along and through machine 10 by way of conveyor system 300.

The hopper 110 and loading chute 120 can use various devices and methods, such as, for example, powered wheels or wedges, powered belts, or gravity, to move each of the carrier tablets 1000 into their designated positions in holding system 200. In machine 10, a portion of loading system 100 is preferably disposed above a portion of conveyor system 300 to take advantage of gravity, in combination with a mechanical loading device.

In the preferred embodiment, holding system 200 has a plurality of holding members or trays 210 with tablet positions 220 having a size and shape that allows for holding of each of the carrier tablets 1000. Preferably, each of the holding trays 210 are rectangular, and the tablet positions 220 are arranged in an array of equi-distantly spaced rows and columns. As will be explained later, this array facilitates operation of the dispensing system 400 in adding the dose droplets 2100 to the carrier tablets 1000. However, the present invention contemplates the use of other structures and methods for securing each of the carrier tablets 1000 and the resulting pharmaceutical product 3000 as they travel along machine 10.

Preferably, each of the holding trays 210 has two rows of thirty tablet positions 220. However, alternative sizes, capacities and shapes of the holding trays 210 and the tablet positions 220 may be used to accommodate different shapes and/or sizes of carrier tablets 1000 and to increase efficiency.

Holding system 200 tracks individual carrier tablets 1000 by their designation in each of the tablet positions 220. This allows machine 10 to perform various real-time monitoring, feedback and adjustment activities upon each of the carrier tablets 1000, dose droplets 2100 and pharmaceutical product 3000, and also to make determinations as to whether each of the tablets, droplets or resulting product have met the quality control standards that are designated for a particular pharmaceutical product. The tracking of each of the carrier tablets 1000, dose droplets 2100 and/or pharmaceutical product 3000 throughout the process carried out by machine 10, allows for acceptance or rejection during the process. The present invention also contemplates tracking of unacceptable tablets for removal by acception-rejection system 800 based on the real-time monitoring.

Various tracking or identification methods can be used by holding system 200 for each of the carrier tablets 1000. In the preferred embodiment of machine 10, holding trays 210 have a bar code 230 that can be scanned to provide identification and information to control system 900, and which can also be used to track and monitor the individual carrier tablets 1000, dose droplets 2100 and/or pharmaceutical product 3000 throughout the process. As will be discussed later in greater detail, the data compiled throughout the process is stored by control system 900. The data is based upon the individual carrier tablets 1000, dose droplets 2100 and/or pharmaceutical product 3000, as opposed to contemporary quality control methods that use batch-sampling.

In the embodiment of machine 10, holding system 200 positions each of the carrier tablets 1000 so that dispensing system 400 can add the dose droplet 2100 to the outer surface 1100 (shown in FIG. 11), which is facing away from the holding tray 210. The present invention contemplates the dispensing system 400 also adding the dose droplet 2100 to the opposing outer surface 1200 of the carrier tablet 1000 (shown in FIG. 12). This would allow for a greater capacity of liquid dose 2000 being carried by the carrier tablet 1000 (on both of its outer surfaces 1100 and 1200), as well as providing a more uniform and symmetrical pharmaceutical product 3000.

Dosing of both sides of the carrier tablet 1000 would also provide the ability for different liquid doses 2000, e.g., different active agents, to be dispensed upon a single tablet, such as, for example, where the different liquid doses are incompatible and cannot be mixed together in liquid form or where the different liquid doses cannot be layered on top of each other. The present invention contemplates dispensing system 400 adding one or more different liquid doses 2000 to carrier tablets 1000 through layering, through depositing on opposing outer surfaces 1100 and 1200, and/or both.

Machine 10 can also be used to re-process the carrier tablets 1000 any number of times through the dispensing system 400 in order to add each of the different liquid doses 2000. Machine 10 may have additional dispensing systems 400 in series that will add each of the different liquid doses 2000 to the carrier tablets 1000.

Holding system 200 can alternatively provide for dispensing the liquid dose 2000 (or different liquid doses) on both sides of the carrier tablets 1000 by providing dispensing system 400 with access to both sides of the carrier tablet. Examples of such alternative methods of dispensing include, but are not limited to, inverting holding tray 210 so that each of the carrier tablets 1000 are transferred into a second holding tray 210 so that the opposing outer surfaces 1200 are now facing away from the second holding tray or using a holding tray that holds each of the carrier tablets around their perimeters or outer circumferences so that both outer surfaces 1100 and 1200 are simultaneously accessible.

The flipping or inverting of each of the carrier tablets 1000 or their holding tray 210 can be done near the end of the process so that the opposing outer surface 1200 is re-processed by the same components or a second set of components could be added to machine 10 to continue the process with respect to the opposing outer surface. Additionally, the inverting of each of the carrier tablets 1000 or their holding tray 210, can be done by holding system 200 to allow for other operations or processes to be performed on opposing outer surface 1200, such as, for example, coating or printing both sides of the pharmaceutical product 3000.

Conveyor system 300 provides for movement of holding trays 210 along machine 10 and through the various stages or systems of the machine. In the preferred embodiment of machine 10, conveyor system 300 provides for movement of holding trays 210 along a substantially horizontal path. However, the present invention contemplates movement of the holding trays 210 in other directions, such as, for example, in a vertical path, where spacial economy, the use of gravity or other reasons suggest or dictate such a direction of movement.

Conveyor system 300 has a drive conveyor 310. Drive conveyor 310 is controlled by control system 900, shown in FIG. 1, and is preferably variable speed. Holding trays 210 are preferably removably connected to drive conveyor 310. Holding trays 210 are securely connected to the drive conveyor 310 so that each of the tablet positions 220 remains constant with respect to the drive conveyor in order to provide accuracy in dispensing and monitoring of the carrier tablets 1000, dose droplets 2100 and pharmaceutical product 3000. In the preferred embodiment of machine 10, drive conveyor 310 is a circulating conveyor belt that traverses the length of machine 10 and, more preferably, is a serial real-time communications system drive unit. However, the present invention contemplates other types and methods of moving the holding trays 210, such as, for example, parallel drive chains, tracks, belts or wheels to which the holding trays can be removably connected.

The present invention also contemplates the use of a number or series of holding trays 210 that are pivotally secured to each other to form a belt-like structure or tray belt, which can be operably connected to the drive conveyor 310. Machine 10 can have a plurality of tray belts with different sizes and/or shapes of tablet positions 220 to accommodate different sizes and/or shapes of carrier tablets 1000. The tray belt is a length or line of holding trays 210 that is connectable at opposing ends to form a loop. When the holding trays 210 are to be replaced for a different pharmaceutical product 3000, the tray belt is fed along the drive conveyor 310 and then secured at its opposing ends to form the belt along the machine 10. To expedite the connection of the second tray belt to drive conveyor 310, the second tray belt can preferably be connected to the end of the first tray belt that is being removed, as that first tray belt is driven along and off of the drive conveyor.

The present invention also contemplates the use of any number of drive conveyors 310. For example, different systems of machine 10 can have independent drive conveyors 310 that allow for independent control of the speed of the drive conveyors, such as, for example, to more rapidly remove the pharmaceutical product 3000 from the end of the process. In such an alternative embodiment, control system 900 would preferably control the various independent drive conveyors 310, and be able to coordinate their movement.

In the preferred embodiment, dispensing system 400 provides for the addition of the liquid dose 2000 to each of the carrier tablets 1000, and provides for real-time monitoring, feedback and adjustment. To dispense the liquid dose 2000, dispensing system 400 has a gantry 410 that laterally spans above and across drive conveyor 310, and is longitudinally movable with respect to the drive conveyor. The movement of gantry 410, including speed and position, is controlled by control system 900.

The gantry 410 has a dispensing module 420 movably connected thereto. The dispensing module 420 is movable along the longitudinal axis of the gantry 410, which laterally traverses across the drive conveyor 310. The movement of the dispensing module 420, including speed and position, is also controlled by the control system 900.

Based upon the movement of the gantry 410, and its own movement with respect to the gantry, the dispensing module 420 is capable of movement along X and Y axes with respect to the drive conveyor 310 and the holding trays 210. Additionally, the present invention contemplates movement of the gantry 410, the dispensing module 420, and/or both, along a Z-axis with respect to the drive conveyor 310 and the holding trays 210. The movement of the dispensing module 420 allows it to accurately dispense the dose droplet 2100 on each of the carrier tablets 1000 that are in the array of tablet positions 220 on holding tray 210. Control system 900 can also adjust the movement of the dispensing module 420 and the gantry 410 to accommodate different sizes and shapes of holding trays 210, as well as different arrays of tablet positions 220 on the holding trays.

Figure 2A:
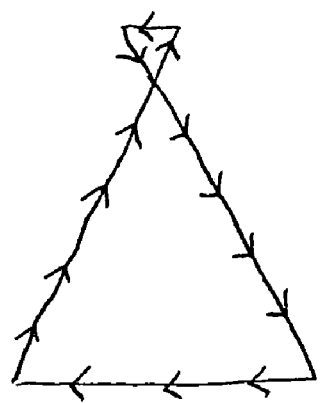
FIG. 2a is a representation of a path of continuous movement of the dispensing module of the pharmaceutical manufacturing machine of FIG. 1.
Figure 2B:
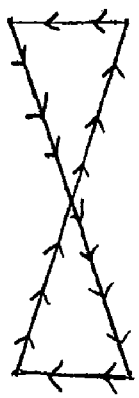
FIG. 2b is a representation of another path of continuous movement of the dispensing module of the pharmaceutical manufacturing machine of FIG. 1.
Figure 2C:
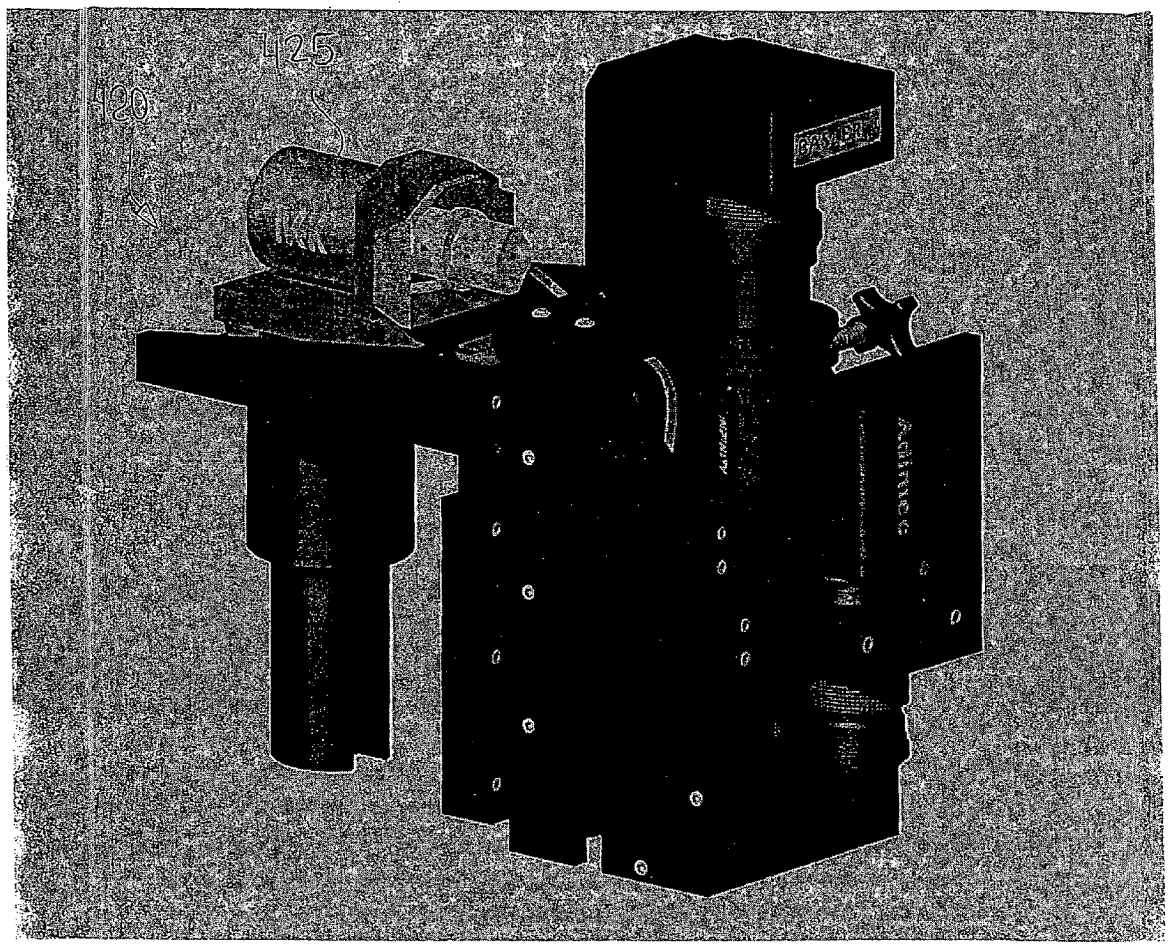
FIG. 2c is a perspective view of a dispenser assembly of the pharmaceutical manufacturing machine of FIG. 1.
Figure 2D:
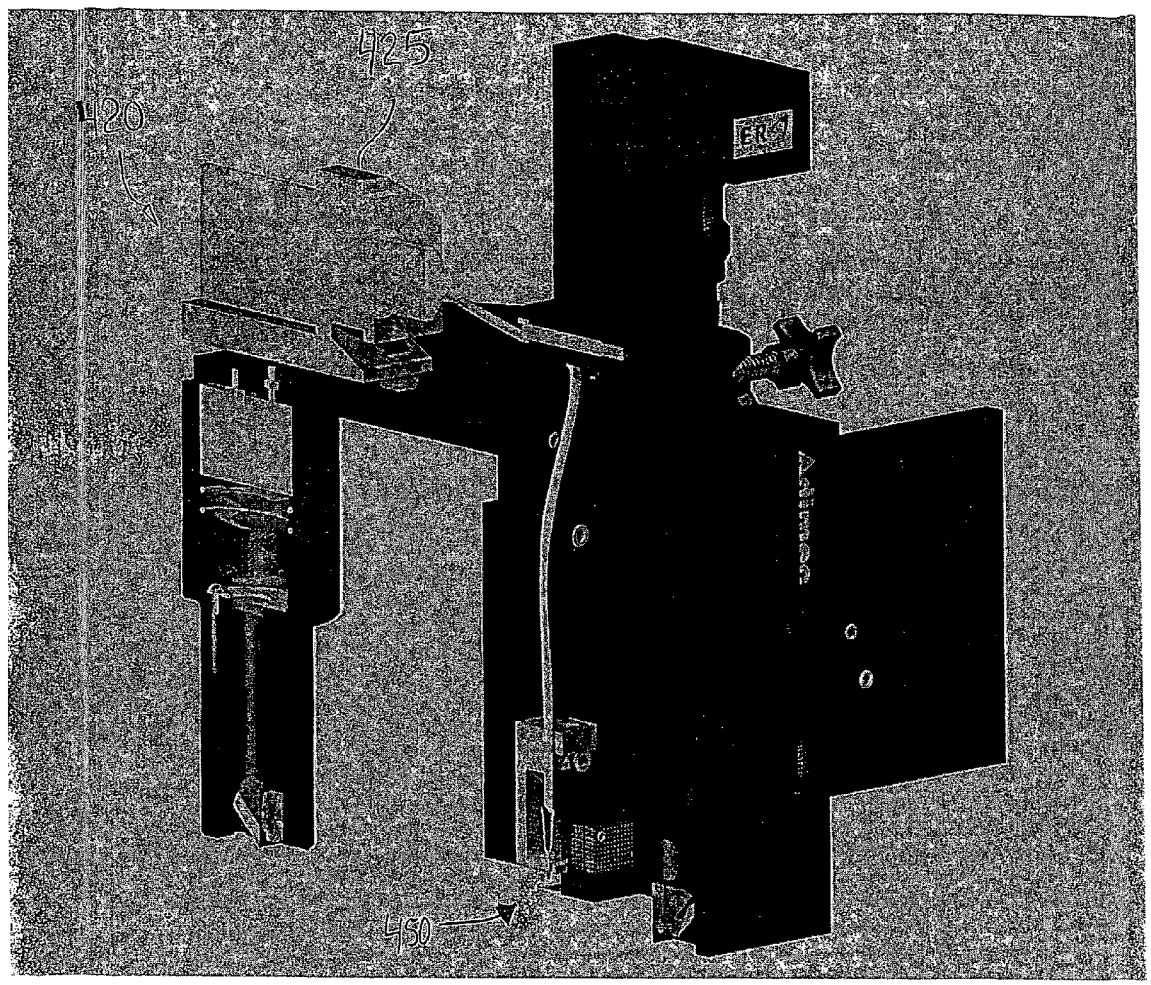
FIG. 2d is a perspective cross-sectional view of the dispenser assembly of FIG. 2c.

The use of the gantry 410 to move the dispensing module 420 along X and Y axes (and the Z axis if desired), provides for smooth movement and accurate alignment of the dispensing module with each of the carrier tablets 1000. This is especially significant in the preferred embodiment of machine 10 where the drive conveyor 310 continues to move the holding tray 210 through the dispensing system 400 as the dose droplets 2100 are being dispensed. The continuous movement of each of the carrier tablets 1000 along machine 10 as the dispensing step is occurring speeds up the manufacturing process. Additionally, smooth continuous movement of the holding tray 210 and the carrier tablets 1000 thereon, as opposed to dispensing onto the carrier tablets via indexing or discontinuous movement, provides for less wear and tear on the machine 10 and its components, particularly the drive conveyor 310. Dispensing module 420 preferably moves in an X-like path to accurately dispense on each of the carrier tablets 1000. The size and shape of the X-like path depends upon the dispensing speed and the spacing of tablet positions 220, as shown in FIGS. 2a and 2b. It should be further understood by one of ordinary skill in the art that the dispensing module 420 can be moved along alternative paths that preferably allow for continuous movement of the carrier tablets 1000 during dispensing.

The accuracy of the alignment of the dispensing module 420 with each of the carrier tablets 1000, and the efficiency of the movement of the module, is facilitated by the use of the rectangular array of tablet positions 220 along holding tray 210 and the control of the movement of the module and gantry 410 in a rectangular coordinate system. However, the present invention contemplates the use of other structures and methods that could also be used to move the dispensing module 420 with respect to each of the carrier tablets 1000, as the drive conveyor 310 continues to move through the dispensing system 400, such as, for example, a multiple axis robotic arm and/or along different coordinate systems.

In the preferred embodiment of machine 10, the dispensing system 400 has a pair of dispensing modules 420 connected to gantry 410. The use of more than one dispensing module 420 provides for increased speed and efficiency in dispensing of the liquid dose 2000. Additionally, the use of more than one dispensing module 420 would allow the dispensing system 400 to add different liquid doses 2000 to a carrier tablet 1000 without cleaning or replacing the module, such as, for example, in layering or on opposing outer surfaces 1100 and 1200 through re-processing the carrier tablet back through the dispensing system.

Dispensing module 420 dispenses a desired amount of active agent onto the carrier tablet 1000. In the preferred embodiment of machine 10, the dispensing module 420 has a pump 425, a flow cell 430, and a dispensing head 435. The present invention contemplates a single dispensing module 420 that has duplicate components, such as, for example, a pump 425 and a flow cell 430 that are in fluid communication with a pair of dispensing heads 435, and/or other combinations or numbers of components for any number of dispensing modules.

The pump 425 is connected to a liquid dose source 440. In the preferred embodiment of the machine 10, the liquid dose source 440 is a movable container 445 that is connected to the pump 425 via removably connectable conduit 447, so that the liquid dose 2000 can be quickly and efficiently replaced.

The present invention contemplates the use of a liquid dose source 440 with replaceable cartridges, containers or canisters (not shown) that can be easily inserted in, or connected to, the liquid dose source. For lower dosages where only small amounts of the liquid dose 2000 are being dispensed, the liquid dose source 440 with replaceable cartridges, containers or canisters is especially useful for facilitating operation of machine 10.

The pump 425 is preferably a metered, positive displacement pump (shown in FIGS. 2c through 2f), which causes the dispensing head 435 to dispense a single dose droplet 2100. The metered, positive displacement pump 425 is controlled by the control system 900, and facilitates the accuracy and control of dispensing a single dose droplet 2100 of the desired size so that the proper dosage of active agent is added to the carrier tablet 1000. However, the present invention contemplates the use of other types of pumps, such as, for example, a time-pressure pump or reciprocating piston pump connected to a dispensing module that can provide the same degree of accuracy and speed in dosing the carrier tablet 1000.

Figure 2E:
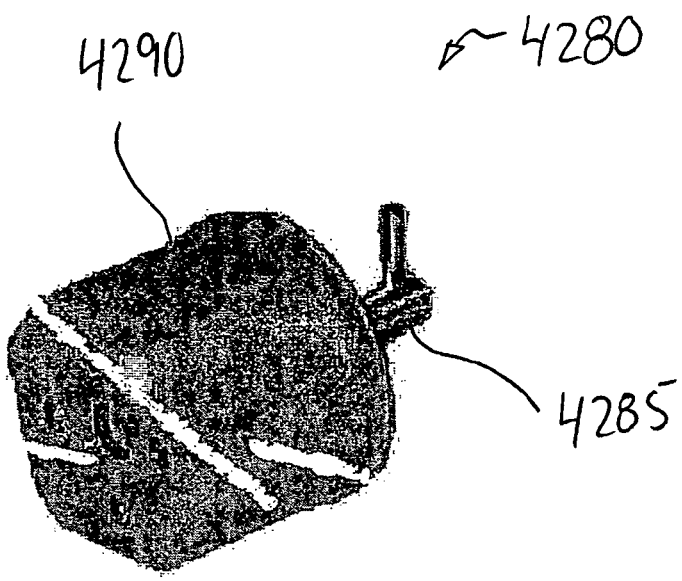
FIG. 2e is a perspective view of the pump module of the dispenser assembly of FIG. 2c.
Figure 2F:
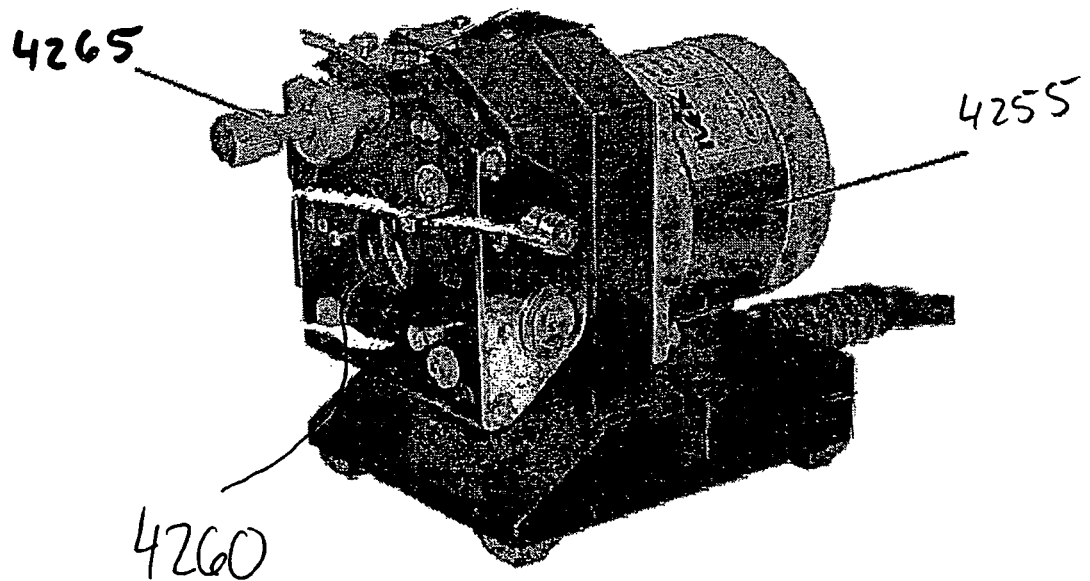
FIG. 2f is a perspective view of the motor module of the dispenser assembly of FIG. 2c.

Pump 425 has a motor module 4250 and a piston module 4280, as shown in FIGS. 2e and 2f. The motor module 4250 has a motor 4255, a connection port 4260 and an adjustment mechanism 4265. The piston module 4280 has a piston assembly 4285 and a cylinder 4290. When the piston module 4260 is operably connected to the motor module 4250 through connection port 4260, the piston on piston assembly 4285 is driven which imparts both reciprocating and rotary motion to the piston. The magnitude of the piston stroke is manually adjustable by the adjustment mechanism 4265. The present invention contemplates automatic adjustment through use of the real time monitoring, feedback and control as described herein.

Pump 425, as controlled by the control system 900, can skip select tablet positions 220, where the carrier tablets 1000 contained therein have been designated as rejected. Machine 10 provides for inspection of the carrier tablets 1000 before they undergo the dispensing process described above. In the preferred embodiment, the tablet inspection is performed by a camera or video/digital recording device (hereinafter referred to as "camera") 426 and gantry assembly (not shown), which provide images of each of the carrier tablets 1000 for inspection by control system 900.

Alternative inspection devices and methods can be used which determine the condition of the carrier tablet, as well as ensure that it is properly positioned in tablet position 220. Selective dispensing by pump 425 improves efficiency by not wasting any liquid dose 2000 on any carrier tablets 1000 that have already been deemed to not meet the required tolerances of the pharmaceutical product 3000 or are not properly positioned for receiving the dose droplet 2100.

The pump 425 is connected to the flow cell 430. The flow cell 430 determines the concentration of the active agent in liquid contained in container 445 that is going to be dispensed through the dispensing head 435, which will be used in the real-time monitoring of the dose droplets 2100. This concentration information is provided to the control system 900.

The dispensing head 435 has a dispensing nozzle 450 (shown in FIG. 2d) through which the pressurized, metered amount of liquid dose 2000 is dispensed, and forms the dose droplet 2100. The dose droplet 2100 dispenses onto the outer surface 1100 of the carrier tablet 1000.

Nozzle 450 provides for exact amounts of liquid dose 2000 being dispensed. The liquid dose 2000 is preferably dispensed by a very precise, positive displacement, piston pump 425 that pumps the liquid through tubing to the nozzle 450. The proper selection of liquid composition, viscosity, the materials of construction and orifice size of the nozzle 450 are significant and/or critical parameters to the reproducibility of droplets formed.

Nozzle 450 can also be made from a hydrophobic material and/or have a hydrophobic coating to facilitate formation and dispensing of dose droplet 2100 by compensating for liquid vehicle composition/formulation and surface tension.

Figure 2G:
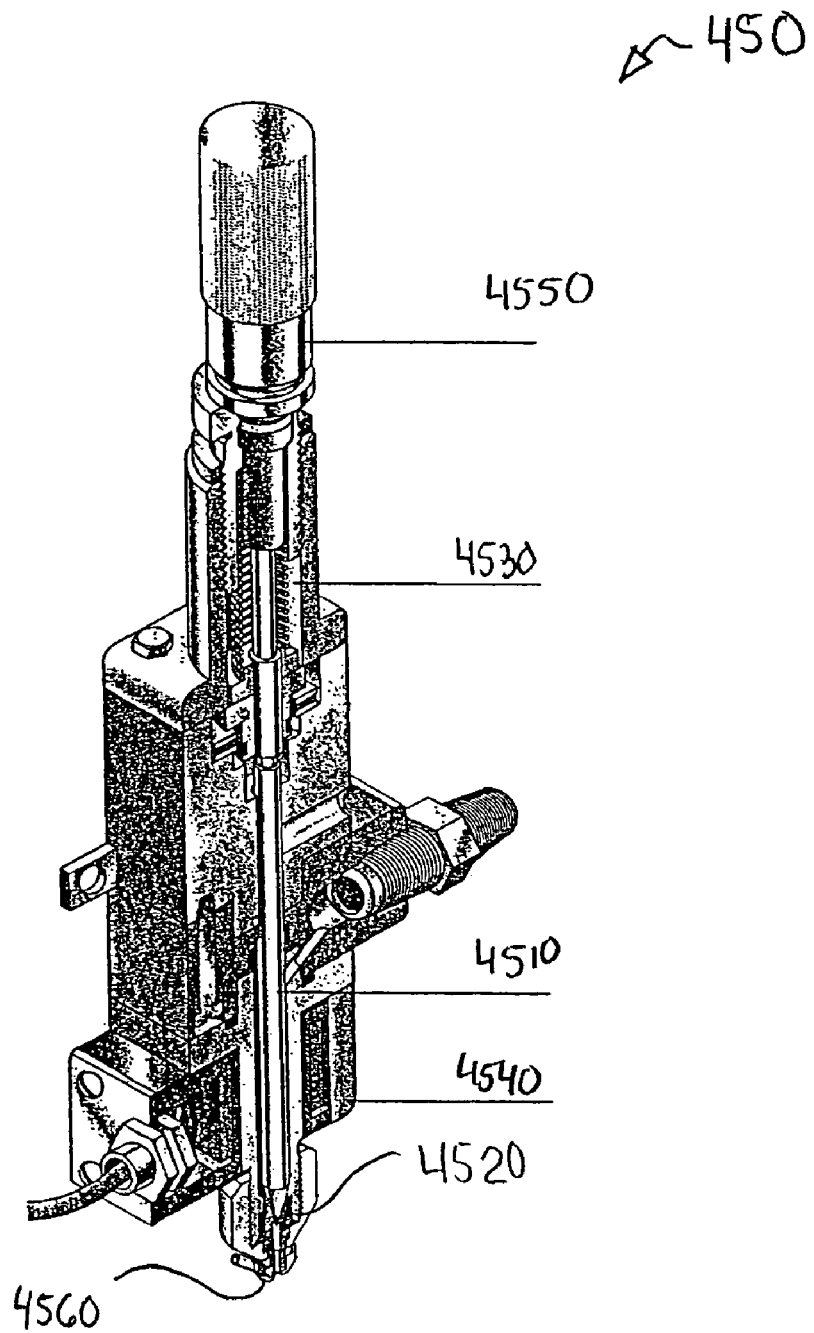
FIG. 2g is a perspective cross-sectional view of another embodiment of a nozzle of the pharmaceutical manufacturing machine of FIG. 1.
Figure 2H:
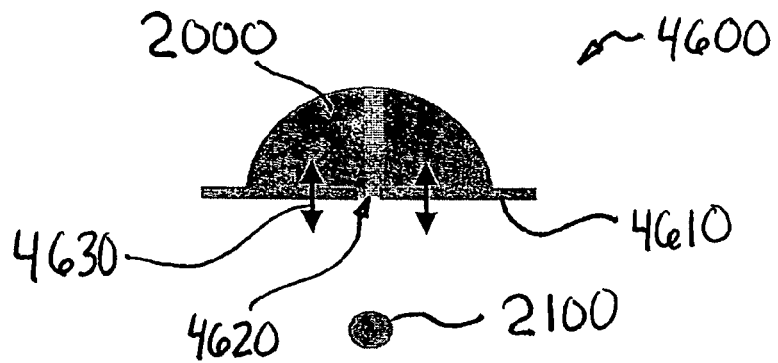
FIG. 2h is a schematic representation of another embodiment of a dispensing assembly of the pharmaceutical manufacturing machine of FIG. 1.

In an alternative embodiment shown in FIG. 2g, nozzle 450 has an internal plunger 4510 that is retracted to allow the exact amount of liquid dose 2000 to enter the dispensing chamber 4520 under pressure of pump 425. Preferably, plunger 4510 is spring-loaded by a spring 4530, or other biasing device, and can be retracted by air pressure, such as, for example, by a solenoid driven pressure source. The liquid dose 2000 is dispensed as a result of the retraction of the plunger 4510. Under automatic control, the time that the plunger 4510 is in the open position, the pressure maintained on the reservoir of liquid dose and the vehicle composition are significant and/or critical parameters to the reproducibility of the droplets formed.

Chamber 4520 is preferably selectively sealed so that the chamber and liquid dose 2000 contained therein remain under pressure. A heater 4540 may be utilized to facilitate the ejection process. Nozzle 450 may have a micro-adjuster 4550 or other adjustment mechanism, manual or automatic (such as being controlled by control system 900 with real-time monitoring, feedback and control), that provides for adjustment of the amount of liquid dose 2000 that is allowed to exit the dispensing chamber 4520. Nozzle 4560 may be a co-axial air exhaust 4560 that further facilitates dispensing of liquid dose 2000.

The dispensing system 400 uses a pump and nozzle assembly to form and dispense the dose droplet 2100. This is advantageous due to the accuracy of the components as described above and the ability to perform real-time monitoring of their activities. Also, the dispensing system 400, through use of nozzle 450, provides a spherical or substantially spherical dose droplet 2100, which reduces or prevents splashing and overspray.

To facilitate formation of a spherical droplet with a well-defined shape, the liquid dose 2000 can have additives included, such as, for example, a polymer, such as, for example, hydroxypropyl cellulose. The present disclosure also contemplates the use of other additives to be combined with the active agent, such as, for example, a film former to facilitate formation of film 2200 or a marker ingredient to be used with the imaging techniques described herein, such as, for example, a surrogate for chemical imaging.

The additive or additives, such as, for example, the polymer, enhances or facilitates the ability of the liquid dose 2000 to lock on to the tablet. The polymer or other such additive can also provide liquid dose 2000 with the desired surface tension and/or viscosity so that a single droplet is dispensed by dispensing system 400, which facilitates control of the amount of the liquid dose and measurement of the droplet, as will be described later in greater detail. Examples of such additives include, but are not limited to, hydroxypropyl cellulose, hydroxypropylmethyl cellulose, carboxymethyl cellulose, polyvinyl alcohol, polyvinylpyrrolidone, carrageenan (kappa, iota or lambda), gelatin, polyethylene glycol, polyethylene oxide, pullulan, and/or acrylic copolymers (e.g., EUDRAGIT® grades RL, RS, E, L, S, FS30D), or any combinations thereof.

The dispensing system 400, and the use of a liquid dose 2000 and dose droplet 2100 that are dispensed onto the carrier tablet 1000 is advantageous over contemporary systems and processes in that the production facilities or sites where the machine 10 is located can centrally process, e.g., liquify, the liquid dosage. This reduces the steps of the production, such as eliminating off-site production and delivery, which decreases production time and saves on costs. Where OHC4 compounds are being used, this is especially advantageous in reducing the handling of the compounds by the workers.

Dispensing system 400 can alternatively have a nozzle-plate assembly 4600 (a portion of which is schematically represented in FIGS. 2*h* through 2*j*) to form and dispense the dose droplet 2100. The assembly 4600 has a plate 4610 with an aperture or nozzle opening 4620 therethrough. The plate 4610 is capable of movement with respect to the supply of liquid dose 2000, as indicated by arrows 4630. Such movement includes, but is not limited to, vibration of the plate 4610 in order to actuate the dispensing. The liquid dose 2000 is dispensed through nozzle opening 4620 when the plate 4610 is selectively moved towards the supply of the liquid dose.

Figure 2I:
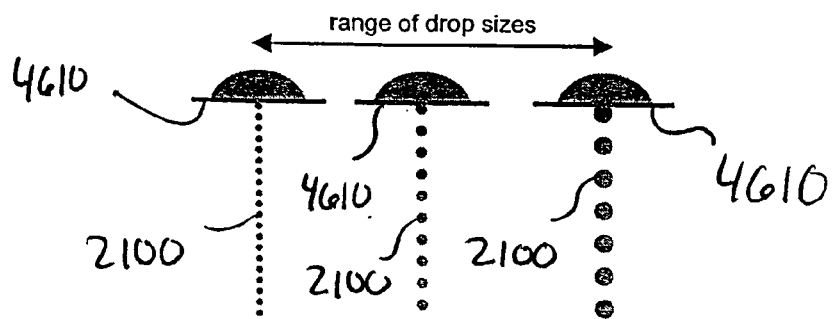
FIG. 2i shows the range of droplets that can be dispensed from the assembly of FIG. 2h.
Figure 2J:
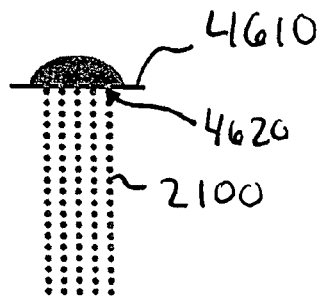
FIG. 2j shows the dispensing assembly of FIG. 2h with multiple nozzles or apertures.

As shown in FIG. 2i, the size of nozzle opening 4620 can be adjusted or changed to provide for a range of different sizes or volumes for dose droplet 2100. The ability to accurately size very small openings in plate 4610 and the dispensing dynamics of the assembly 4600 allow for dispensing of very small amounts of liquid dose 2000, preferably as small as one pico liter. As shown in FIG. 2j, a number of nozzle openings 4620 can also be used in the plate 4610 so that array dispensing can be done.

Nozzle-plate assembly 4600 is advantageous due to its minimization of components so that there are fewer materials in contact with the liquid dose 2000. The dispensing operation of the assembly 4600 is reliable since there are no narrow channels and the design is insensitive to air entrapment. Dispensing through the movement of plate 4610 makes the assembly 4600 easy to load and easy to clean. Dead volume for the supply of liquid dose 2000 is minimized or eliminated due to the planar or substantially planar shape of plate 4610.

The present invention further contemplates the use of other structures and methods of dispensing the liquid dose 2000 onto the carrier tablet 1000, such as, for example, by a pad-printing device where the drug is loaded into the ink cartridge.

Dispensing system 400 has a dose inspection system 460 that provides real-time monitoring of each dose droplet 2100 that is to be added to the carrier tablets 1000. In the preferred embodiment of the machine 10, dose inspection system 460 uses high-speed imaging of the dose droplet 2100 to determine the volume of the droplet. Dose inspection system 460 has a high-speed camera 465, preferably digital camera, that is connected to gantry 410 and which is able to take a high-speed image 470 (shown in FIG. 4) of each dose droplet 2100. In the preferred embodiment of machine 10, two high-speed digital cameras 465 are used, which correspond to each of the two dispensing modules 420.

Referring to FIGS. 1 through 4, the image 470 of the dose droplet 2100 is preferably taken in-flight after the dose droplet has left the nozzle 450 but before it makes contact with carrier tablet 1000. The machine 10 uses a laser detector to trigger the camera 465 to obtain the image 470 due to the high speed of the dose droplet 2100 (shown generally in FIG. 2d). However, the present invention contemplates the use of other triggering devices and methods for triggering camera 465 and obtaining image 470.

Image 470 is used by the control system 900 to calculate a volume of each of the dose droplets 2100. The calculated volume of the dose droplet 2100, along with the concentration obtained from flow cell 430, is used to determine the dosage of active agent that is being dispensed onto the carrier tablet 1000. Any dosage that does not meet tolerances will be marked with an error code by control system 900 so that the carrier tablet 1000 having that particular dose droplet 2100 can be rejected.

Where higher doses of active agent are required in a pharmaceutical product 3000, dispensing module 420 may dispense a number of dose droplets 2100 or a stream of liquid dose 2000. Dose inspection system 460 still has the ability to capture the image 470 of the stream of liquid dose 2000, and the volume and dosage calculations can be made therefrom.

Dispensing system 400 has a drying system 475 that performs drying of the dose droplet 2100 on the carrier tablet 1000. In the preferred embodiment of the machine 10, drying system 475 has an oven 480 and drying monitors or oven sensors 482 (not shown in detail). The oven 480 provides heat and air flow to the dose droplet 2100 and carrier tablet 1000 so that the film 2200 is formed on the outer surface 1100 or substantially along the outer surface of the carrier tablet. The oven sensors 482 monitor the drying conditions of each of the dose droplets 2100 and carrier tablets 1000 to ensure that the pharmaceutical product 3000 meets the required tolerances. The heating or drying of liquid dose 2000 may evaporate excess amounts of liquid, causing the active agent to become captured in the film 2200. The drying process of drying system 475, as opposed to allowing the liquid dose 2000 to 'air dry' on the carrier tablet 1000, can be particularly useful where reduction or elimination of certain excipients from the pharmaceutical product (via evaporation), such as, for example, a solvent like methanol, is desired.

For higher dosages of pharmaceutical product, such as, for example, above 5 or 10 mg, drying system 475 can dry layers of the liquid dose 2000 as they are dispensed on top of each other and/or can dry the liquid dose on opposing sides of the carrier tablet 1000. This allows for a greater volume of liquid dose 2000 to be carried by carrier tablet 1000.

Drying conditions, such as, for example, temperature, airflow and humidity are monitored by the oven sensors 482, and a number of such sensors are used to account for any variance in conditions along the oven 480. The data gathered by the sensors is provided to control system 900 for evaluation of the quality of the carrier tablets 1000 and dose droplets 2100 in each of the holding trays 220.

In the preferred embodiment, the drying conditions are monitored for the entire holding tray 220, and error codes can be assigned to the individual carrier tablets 1000 and dose droplets 2100 contained therein, based upon a holding tray being affected by an oven condition that does not meet the required tolerances. Alternatively, portions of trays can be monitored for drying conditions by placing more sensors 482 in the oven 480 in strategic positions. Additionally, the present invention contemplates the monitoring of other conditions or criteria related to the drying process, such as, for example, conditions that may be more significant to particular pharmaceutical product 3000.

The present invention also contemplates oven 480 being an infrared (IR) oven and/or having a combination of IR, convection, conduction and/or microwave heating. Drying system 475 can include dry sensors to detect conditions, such as, for example, the surface temperature of the carrier tablets 1000, or IR radiation. Drying system 475 may also include a sensor for turning on the oven, such as, for example, a photo-cell triggered by holding trays 210 entering the oven 480.

Dispensing system 400 has a dose confirmation system 500 that provides real-time monitoring, feedback and adjustment for the liquid dose 2000 that has been added to, and dried on, the carrier tablet 1000. In particular, the dose confirmation system 500 monitors the positioning of the liquid dose 2000 on the carrier tablet 1000 and the amount of the liquid dose contained thereon. Preferably, dose confirmation system 500 can also monitor the active agent type and distribution of the liquid dose 2000 on the carrier tablet 1000. Additionally, the dose confirmation system 500 can monitor for other substances, such as, for example, identifying contaminants present on the carrier tablet 1000, as well as the amount of such other substances.

The data obtained by the dose confirmation system 500 is provided to the control system 900. The control system 900 will assign error codes to individual carrier tablets 1000 and their liquid doses 2000 that do not meet the required tolerances of the pharmaceutical product 3000.

In the preferred embodiment of the machine 10, dose confirmation system 500 has a gantry 510 (similar to gantry 410 described above) with a pair of charge coupled device (CCD) cameras 520 that obtain images 525 of each of the carrier tablets 1000. The images 525 are provided to control system 900 for a determination of the position of the liquid dose 2000 with respect to the carrier tablet 1000.

Dose confirmation system 500 also has a probe 530 (shown in FIG. 2) that is used for determining the amount, type and/or distribution of the liquid dose 2000 on the carrier tablet 1000. In the preferred embodiment of machine 10, the probe 530 uses near-infrared (NIR) chemical imaging or UV induced fluorescence chemical imaging to determine the amount of the liquid dose 2000 present on the carrier tablet 1000.

Probe 530 has components that carry out NIR chemical imaging on each of the carrier tablets 1000 in holding tray 210, such as, for example, fiber optics, focal plane array (FPA) detectors, and/or charge coupled device (CCD) detectors. Additionally, liquid crystal tunable filters can be used as wavelength selectors for the NIR chemical imaging. The use of such components, in conjunction with each other or alternatively, is facilitated by the positioning of the active agent along or near the surface of the carrier tablet 1000.

The NIR chemical imaging provides good penetration into the liquid dose 2000 and upper surface 1100 of the carrier tablet 1000 for an accurate measurement of the quantity of the liquid dose. This technique is especially useful for the preferred dosing step where film 2200 is positioned on the upper surface 1100 or substantially on the upper surface of carrier tablet 1000.

In the preferred embodiment of machine 10, probe 530 uses a focal plane array detector to obtain a signal from every point in the sample area. The sample area preferably includes the entire holding tray 210 so that all of the carrier tablets 1000 are being simultaneously measured, which further improves the efficiency of the process. The focal plane detector is able to obtain simultaneous spectral information at every frequency for the sample area. Probe 530 can rapidly and non-destructively measure the liquid dose 2000 for amount, formulation and/or distribution of active agent, as well as monitor or detect other substances contained in or on the carrier tablet 1000.

The present invention contemplates the use of other methods and devices for determining the presence, type, distribution and/or amount of a particular liquid dose or doses 2000 on the carrier tablet 1000, such as, for example, spectroscopy and/or chemical imaging utilizing Raman and UV reflectance, and various other types of imaging, chemical imaging and/or spectroscopy, such as, for example, UV/visible absorption, fluorescence, laser-induced fluorescence, luminescence, photoluminescence, terahertz, and mid-IR. The present invention contemplates the use of various devices or components that facilitate the use of spectroscopy and/or chemical imaging for analysis of the pharmaceutical product 3000, such as, for example, lasers (e.g., pulse lasers), beam splitters, water-vapor free environments (e.g., nitrogen shrouds), optical delays (e.g., variable optical delays), antennas and/or semi-conductors. The present invention contemplates the use of room temperature solid state detectors and/or pulsed time-gated techniques and components. The present invention contemplates the use of techniques for analysis of the pharmaceutical product 3000 that are non-ionizing, non-invasive, non-destructive and/or require low power.

The present invention contemplates the use of any regions of the electromagnetic spectrum which allow for analysis of the carrier tablet 1000 and liquid dose 2000, as well as various techniques and sources for excitation in using the particular type of spectroscopy. The present invention also contemplates the use of other techniques and components for digital imaging to allow for use of chemical imaging of the tablet 1000 and liquid dose 2000. It should be further understood that dose confirmation system 500 also contemplates the use of surrogate detection in any of the spectral ranges.

The coating system 600 of machine 10 provides a coating 2300 (shown in FIG. 12) over the liquid dose 2000 in order to prevent possible abrasion and the resulting loss of any active agent. The coating 2300 may be a sealant. The coating 2300 provides a uniform appearance for the pharmaceutical product 3000 by hiding the liquid dose 2000. The coating can be chosen to closely resemble the color of the carrier tablet 1000 or be another color, such as, for example, a contrasting color to provide different commercial images. Any minor difference in color between the coating 2300 and carrier tablet 1000 is accounted for by having the perimeter of the coating align with the edge of the carrier tablet.

Coating system 600 preferably has a pad-printing device 610, a coating source 620 and a coating dryer 630. The pad-printing device transfers the coating to the upper surface 1100 of the carrier tablet 1000. The pad-printing device 610 is advantageous because of its efficient transfer of the coating to the carrier tablet without any waste, e.g., no overspray.

In the preferred embodiment of machine 10, pad-printing device 610 is connected to or positions adjacent to the machine 10 to print an array of tablets with each reciprocating stroke. Pad-printing device 610 can be movably connected to a gantry 615 or other similar device to facilitate movement of the pad-printing device with respect to the holding tray 220. The holding tray 220 continues to move as the coating 2300 is being applied by the pad-printing device 610. However, the present invention contemplates the use of other devices and methods of positioning the pad-printing device 610 with respect to each of the tablet positions 220 so that the coating 2300 is accurately applied.

The pad-printing device 610 is releasably connected to the coating source 620. In the preferred embodiment of the machine 10, the coating source 620 is a movable container 625 that is connected to the pad-printing device 610 via removably connectable conduit 627, so that the coating can be quickly and efficiently replaced.

Alternatively, a spray device (not shown) or ink jet device can be used to spray the coating upon the carrier tablet 1000. The spray device could also be movably connected to gantry 615 to pass over each of the tablet positions 220. The present invention contemplates the use of other devices and methods for applying a coating 2300 to the carrier tablet 1000, which covers the liquid dose 2000, such as, for example, an ultrasonic atomizer. The coating system 600 can use intermittent, low volume atomized sprayers to locally apply the coating 2300 over the surface of tablet 1000 where the dosage has been applied. The sprayer may use volumetric pumps to intermittently supply coating materials. A two fluid air-liquid atomization sprayer may also be used to generate a fine spray.

As described above with respect to dosing of the carrier tablet 1000 in layers or on opposing sides, the coating system can provide the necessary coating depending upon how the liquid dose or doses 2000 have been added to the carrier tablet, such as, for example, on both sides or between layers. This can facilitate the use of higher volumes of dosages for the pharmaceutical product 3000, such as, for example above 5 or 10 mg.

Coating dryer 630 performs drying of the coating 2300 that has been applied to the carrier tablet 1000 and over the liquid dose 2000. The coating dryer 630 preferably has an oven 640 and oven sensors 650 (not shown in detail). The oven 640 provides heat and air flow to the coating 2300. The oven sensors 650, similar to the oven sensors 482 discussed above, monitor the drying conditions of the coatings 2300 to ensure that the pharmaceutical product 3000 meets the required tolerances.

The printing system 700 of machine 10 provides an identification marker on the coating 2300. The printing system preferably has a pad-printing device 710 that transfers the marker to the coating 2300 of the carrier tablet 1000 and a pair of cameras 720 that obtain an image 730 of each of the identification markers to verify the quality of the image. Unacceptable tablets will be identified by the control system 900 for subsequent rejection by system 800.

In the preferred embodiment of machine 10, pad-printing device 710 and cameras 720 are movably connected to a gantry 735 (similar to gantries 410, 510 and 615) to facilitate movement of the pad-printing device with respect to the holding tray 210 that continues to move as the identification marker is being applied. However, the present invention contemplates the use of other devices and/or methods for positioning the pad-printing device 710 or alternative device with respect to each of the tablet positions 220 for accurate application of the identification markers, such as, for example, lasermarking, inkjet or rotogravure. Each of the marker images 730 is provided to control system 900 for inspection and to determine if the printed identification marker meets the required tolerances of the pharmaceutical product 3000. Also, the present invention contemplates machine 10 having an ink dryer (not shown), such as, for example, an oven, that applies heat and/or air-flow to the identification marker to dry it.

The acception-rejection system 800 provides a pharmaceutical product 3000 that has undergone real-time monitoring and adjustment for quality control to ensure that each of the product meets the required tolerances. Based upon the real-time monitoring being continuously performed at various stages of the process by machine 10, control system 900 has designated each and every pharmaceutical product 3000 as either acceptable or rejected.

Acceptable pharmaceutical product 3000 pass through to the delivery area (not shown in detail), preferably under pressure that is selectively controlled by the control system 900, while rejected product drop into a scrap area, preferably under the force of gravity. However, the present invention contemplates the use of other structures and methods of separating those pharmaceutical product 3000 that are designated by control system 900 as acceptable from those product that have been designated by the control system as rejected.

The control system 900 coordinates and synchronizes the various stages and systems of the machine 10. In the preferred embodiment, control system 900 is a distributed process control system that has a number of microprocessors 910 that control the different systems of machine 10. The microprocessors are preferably coordinated through a workstation 920. However, the present invention contemplates other types of system control including central and regional control, such as, for example, a single microprocessor 910 controlling all of the systems or similar systems being controlled by one of several microprocessors 910.

The microprocessors 910 and workstation 920 are in communication with each other, preferably through a network 930 using an Ethernet switch 935, which allows for the real-time monitoring, feedback and adjustment of the process being performed by the machine 10. The present invention contemplates the use of other structures and methods for communication, such as, for example, hardwiring. The control system 900 also has an archive microprocessor or historian 940, which is used to centrally store the large amount of data that is compiled for each and every pharmaceutical product 3000 that is processed by the machine 10. However, the present invention contemplates other methods of storage of the process data, such as, for example, microprocessors 910 individually storing the data that they have compiled.

The control system 900 preferably has a number of monitors 950 that provide displays of the data, portions of the data, summaries of the data, and/or calculations and conclusions based upon the data, so that the workers can monitor and/or adjust the process as it is occurring. More preferably, the monitors 950, through use of the various microprocessors 910 and/or workstation 920, can selectively display the data, portions of the data, summaries of the data, calculations based upon the data, and conclusions based upon the data. Preferably, control system 900 records data for every product 3000, which includes time, initial tablet status, dose droplet volume, dose droplet concentration, oven temperature, oven humidity, oven air flow, dosage location on tablet, dosage quantity and acceptability.

Figure 5:
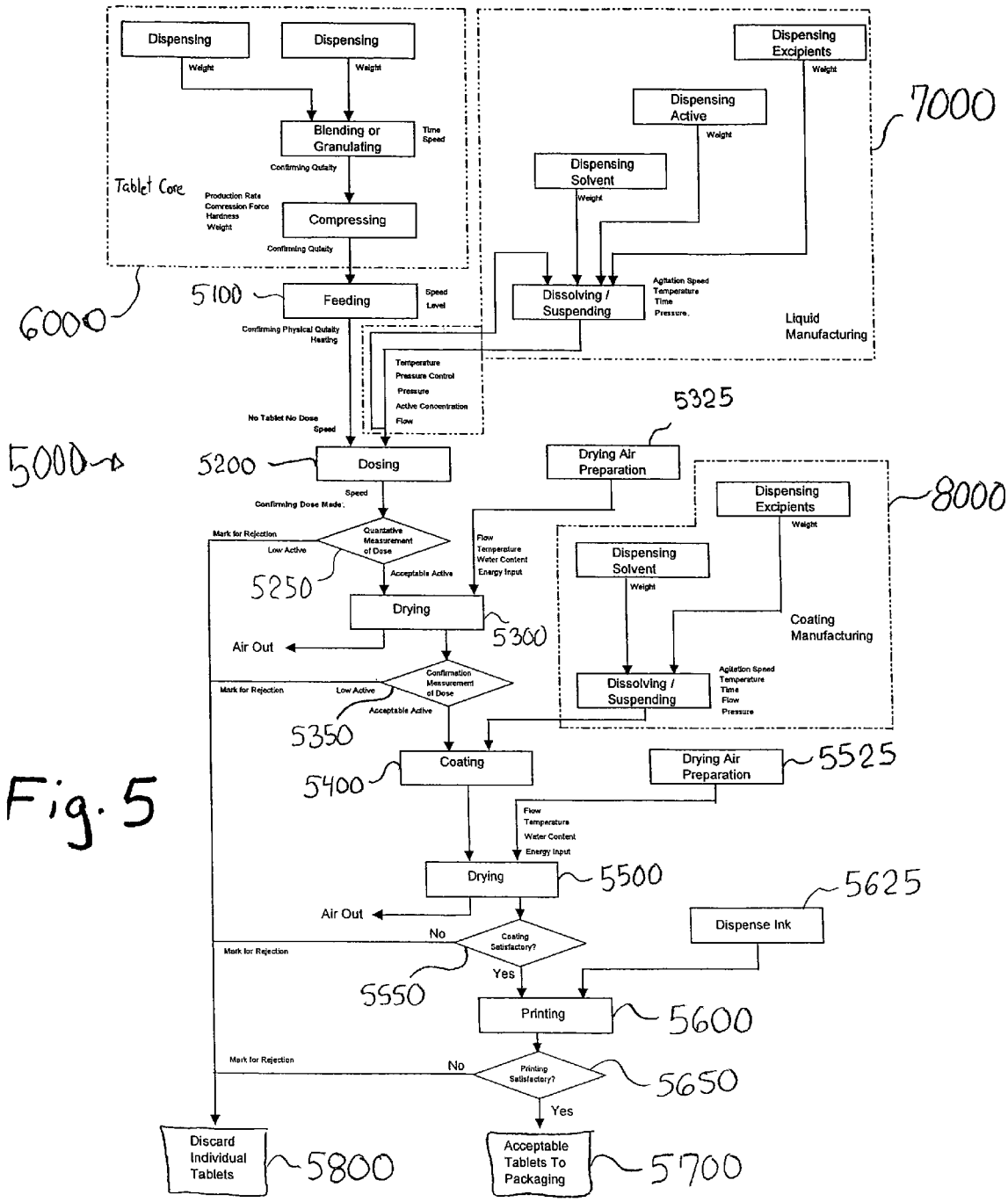
FIG. 5 is a process flow diagram for the process performed by the pharmaceutical manufacturing machine of FIG. 1.

The operation of the machine 10 is shown in the flow chart of FIG. 5. The process 5000 is continuous between each stage, and provides a pharmaceutical product 3000 that is ready for packaging. In addition to the advantage of cost and time savings, process 5000 minimizes worker contact with the various agents, active and inactive, of the pharmaceutical product 3000, which reduces potential contamination, as well as providing safety to the workers in dealing with potentially harmful active agents or other substances such as, for example, occupational hazard category 4 (OHC4) compounds.

The ability of machine 10 to minimize or eliminate worker contact with the product 3000 (including the addition of a packaging step as will be described later), provides a great advantage over contemporary processes and machines. Such contemporary processes require special safety features, such as, for example, dust containment devices and special handling by workers, where OHC4 drugs are being produced. The special safety features and special handling by workers of the contemporary machines and processes, increases the cost of production, as well as the time to produce the product. Machine 10 avoids such costs and reduces the production time, through its automated, real-time control, feedback and/or adjustment. The present invention also contemplates the use of machine 10 in a nitrogen-enriched environment in order to reduce or eliminate any oxidative degradation, which is facilitated by the lack of need for worker intervention in the process 5000.

FIG. 5 shows process 5000 in combination with processes 6000 and 7000 for the manufacture of the carrier tablet 1000 and the liquid dose 2000, respectively. Process 5000 requires the use of carrier tablets 1000 and liquid doses 2000. However, the carrier tablets 1000 and liquid doses 2000 can be manufactured at other facilities and delivered to machine 10. Also, other processes can be used to manufacture the carrier tablets 1000 and the liquid dose 2000 that are different from those shown in FIG. 5.

Feeding step 5100 provides an array of carrier tablets 1000 that will remain securely positioned as they proceed through machine 10 to ensure accurate dispensing of the liquid dose 2000, coating 2300 and identification marker. The feeding step 5100 is performed by the loading, holding and conveyor systems 100 through 300 as described above, and is subject to real-time monitoring, feedback and adjustment by the control system 900.

The feeding step 5100 includes adjustment of the speed of drive conveyor 310 based on a number of factors, such as, for example, the drying time required for the liquid dose 2000 or the amount of time required to dispense the dose droplets 2100. In the preferred embodiment, the speed of drive conveyor 310 dictates the speed and positioning of all other movements in machine 10, such as, for example, synchronization of gantries 410, 510 and 615 based upon the speed of the drive conveyor. However, the present invention contemplates synchronization of the systems being based off of other component's movements or other factors, which provides accuracy in the various dispensing steps of process 5000.

The present invention also contemplates the speed of the conveyor system 300 being adjustable based on the real-time monitoring of the position of the liquid dose 2000 that has been dispensed on the carrier tablet 1000. As described above, the dose confirmation system 500 obtains images 525 of each of the positions of the liquid dose 2000 on the carrier tablets 1000. Control system 900 could adjust the speed of the drive conveyor 310 with respect to subsequent holding trays 220 based upon this data, such as, for example, where the positioning of the liquid dose 2000 is consistently off center in the same direction. Also, the feeding step 5100 includes real-time monitoring of the quality of the carrier tablet 1000, such as, for example, a chipped or broken tablet, so that the carrier tablet can be designated as rejected, which prevents the dispensing of the dose droplet 2100 on that particular carrier tablet.

Dosing step 5200 is performed by dispensing system 400, and, in particular, by the pair of dispensing modules 420. Control system 900 provides a synchronized pulse to metered pump 425 to actuate the pressurized dispensing of the dose droplet 2100. However, the present invention contemplates the use of other signals and techniques to actuate dispensing module 420 for dosing.

Calibration of the dosing step 5200 is provided by a weigh cell 455 (not shown in detail), which monitors the accuracy of the dispensing modules 420. In operation, gantry 410 is positioned over the weigh cell 455, and a preset number of dose droplets 2100 are dispensed onto the weigh cell for weight measurements. This data is compared to data collected from each of the images 470 of the dispensed dose droplets 2100. The control system 900 can then calibrate the dispensing system 400 based upon volume versus weight comparisons of the preset number of dose droplets 2100.

Dose inspection step 5250 is performed by the dispensing system 400 and, in particular, by the dose inspection system 460. The dose inspection system 460 provides a quantitative measurement of the dose droplet 2100 prior to it being added to the carrier tablet 1000, and allows for rejection of those tablets receiving droplets that do not contain the required amount of active agent.

To calibrate the dose inspection step 5250, a vision reticle (not shown) and calibrated volume (not shown) are provided. The vision reticle allows for the determination of a position where the camera 465 can be triggered to capture the image 470 of the dose droplet 2100. The calibrated volume allows for calibration of the dose inspection system 460. In operation, gantry 410 is positioned over the vision reticle. The calibrated volume is released and detected by the dose inspection system 460, and the control system 900 compares the calculated volume (from image 470) to the known calibrated volume for calibration of the dose inspection system. The calibration sequence can be set during the run periodically, such as, for example, every 15 minutes, or by the number of tablets having been processed, and/or can be set by some other standard, which is periodic or otherwise.

The present invention contemplates real-time adjustment of the dosing and dose inspection steps 5200 and 5250 based upon the calibration techniques described above. These calibration steps can be interposed between holding trays 220, and control system 900 can adjust dispensing system 400, such as, for example, adjusting the image volume calculation, based upon discrepancies between the calibrated values and the measured values. Additionally, the present invention contemplates real-time adjustment of the dosing step 5200 based upon the real-time monitoring data obtained by dose inspection step 5250, such as, for example, adjusting the piston stroke of the pump 425 to account for dose droplets 2100 having too large or too small of a volume.

Figure 6:
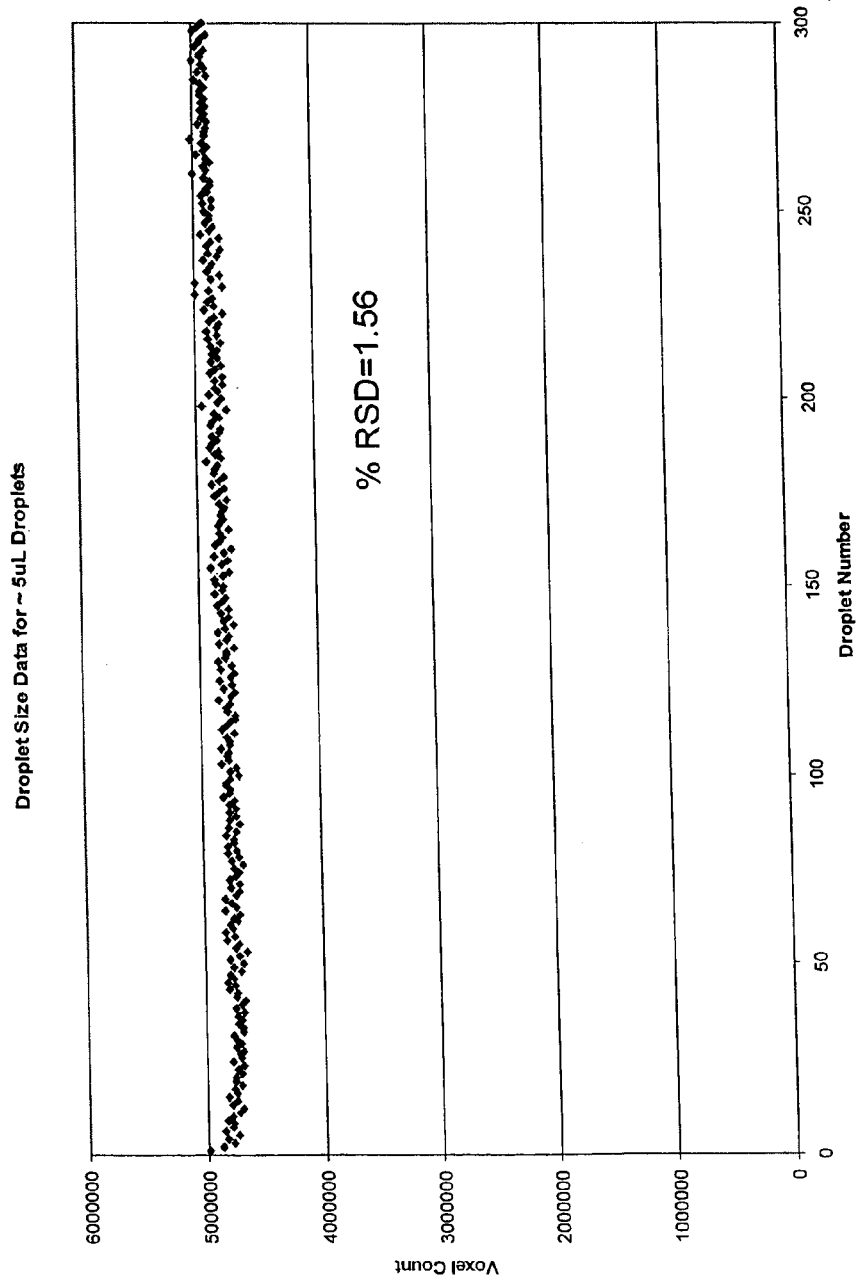
FIG. 6 is a graph of the dose droplet measurements by video imaging and processing for a run of 300 tablets.
Figure 6A:
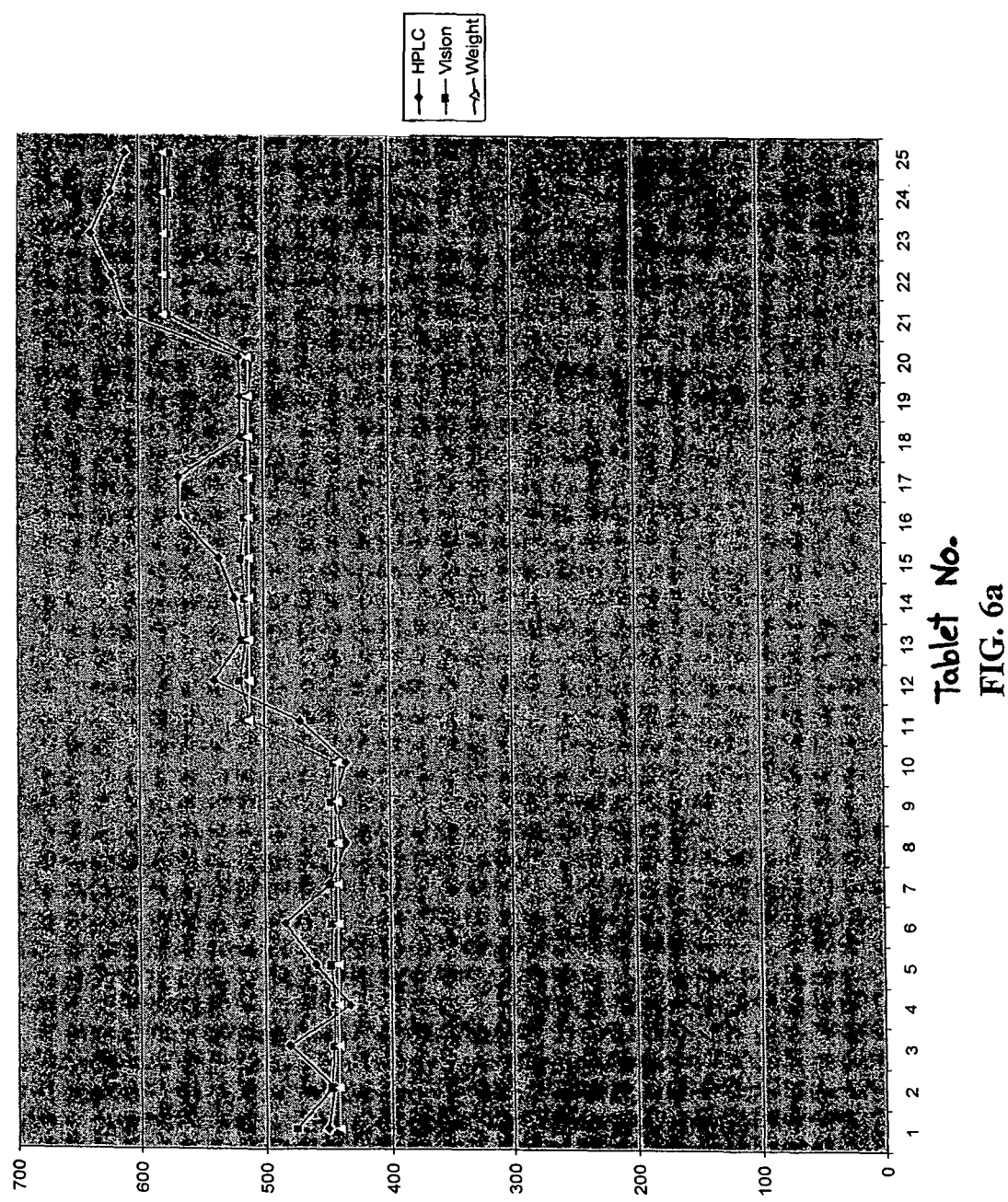
FIG. 6a is a graph comparing dose droplet measurements made by the video imaging, high performance liquid chromatography and weight.
Figure 6B:
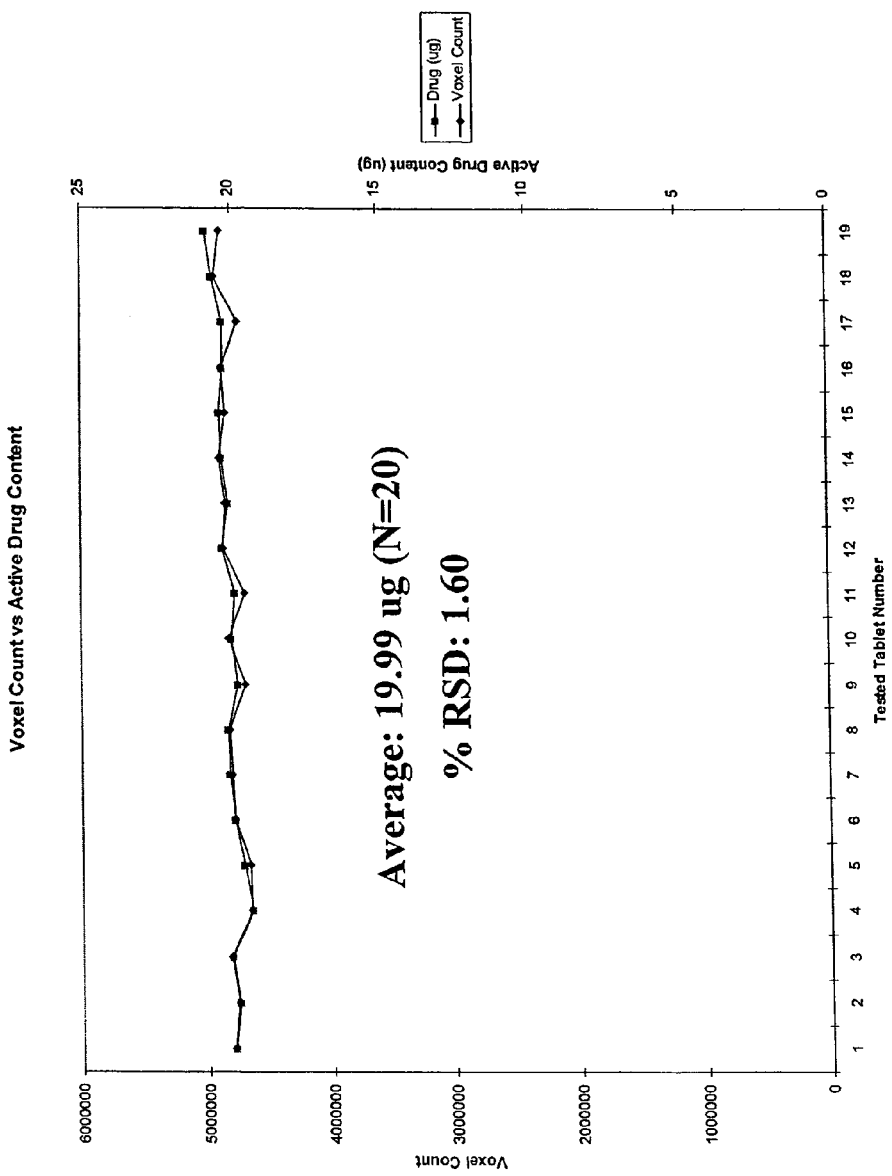
FIG. 6b is a graph of the volumetric determinations by the video imaging and processing compared to drug content measured by high performance liquid chromatography.
Figure 6D:
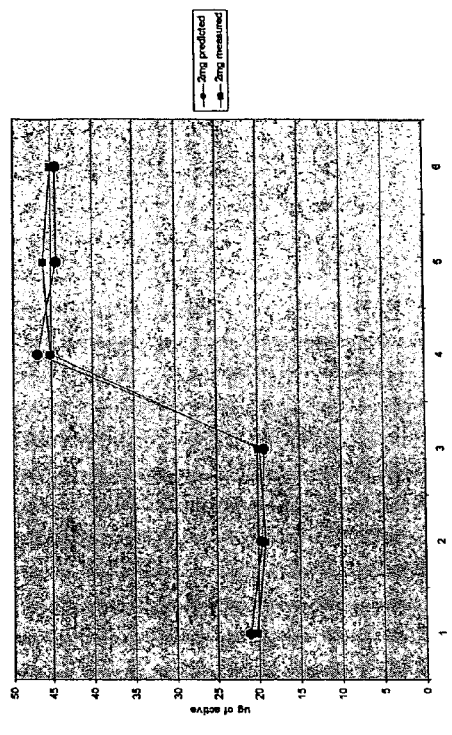
FIG. 6d is a graph of the amount of active agent as predicted by the video imaging compared to that measured by high performance liquid chromatography for a 2 mg dosage.
Figure 6C:
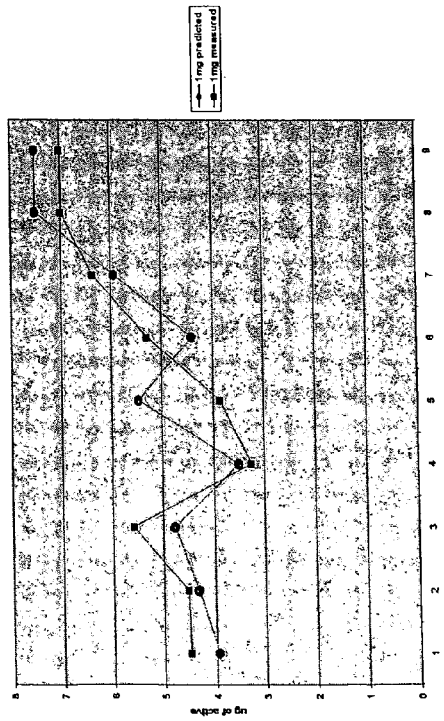
FIG. 6c is a graph of the amount of active agent as predicted by the video imaging compared to that measured by high performance liquid chromatography for a 1 mg dosage.
Figure 6E:
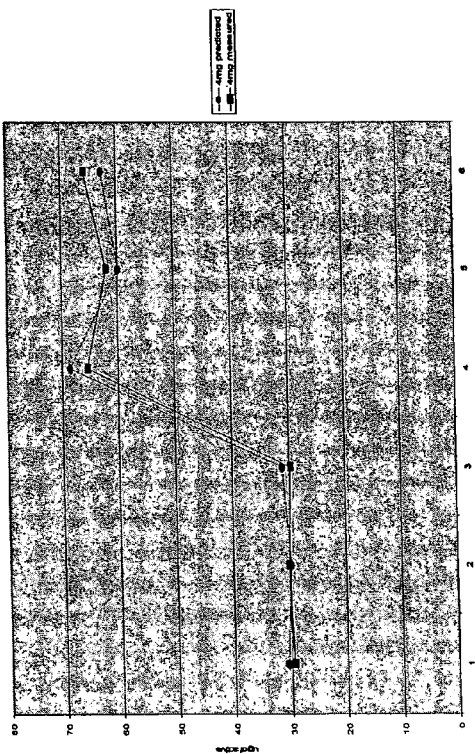
FIG. 6e is a graph of the amount of active agent as predicted by the video imaging compared to that measured by high performance liquid chromatography for a 4 mg dosage.

The high-speed video image method described above for determining the volume of dose droplets 2100, was compared to a High Performance Liquid Chromatography method using a weight analysis as a comparator. As shown in FIGS. 6 through 6e, the sample of results using images 470 and the algorithms performed on the images to determine the volume, provided an accurate determination of the volume of dose droplet 2100 as it is being dispensed.

Alternatively, dose inspection system 460 can utilize optical profilometry for real-time monitoring and feedback control. The components utilized by dose inspection system 460 to carry out the optical profilometry are known to one skilled in the art, such as, for example, a laser and camera. The technique of optical profilometry is especially useful for larger volumes of liquid dose 2000, such as, for example, greater than 10 microliters, where the dispensing system 400 is dispensing a stream, as opposed to the dose droplet 2100.

For the optical profilometry technique, dose inspection system 460 performs a first scan of the carrier tablet 1000 prior to dispensing of the liquid dose 2000 in order to obtain a first profile of the carrier tablet. A second scan is then performed by the dose inspection system 460 to obtain a second profile of the carrier tablet 1000 with the liquid dose 2000 thereon. The difference in the first and second profiles provides the measurement of the volume of liquid dose 2000 that has been dispensed onto the carrier tablet 1000. The present invention further contemplates the use of optical profilometry of the carrier tablet 1000 after the liquid dose 2000 has been dried on the carrier tablet. Also, the first profile may be based upon a predetermined value for the same carrier tablets 1000 to expedite the process and eliminate the need for two scans.

Drying step 5300 and drying air preparation step 5325 are performed by the drying system 475 and provide for drying of the dose droplet 2100 on the carrier tablet 1000 as the holding trays 220 move through oven 480. Various drying conditions are monitored for acceptance or rejection of the holding trays 220. The present invention contemplates the real-time monitoring of the drying conditions to be used for real-time adjustment of the drying system 475, such as, for example, temperature, air-flow rate and/or humidity being adjusted by control system 900 based upon detection of abnormalities in these conditions.

Figure 7:
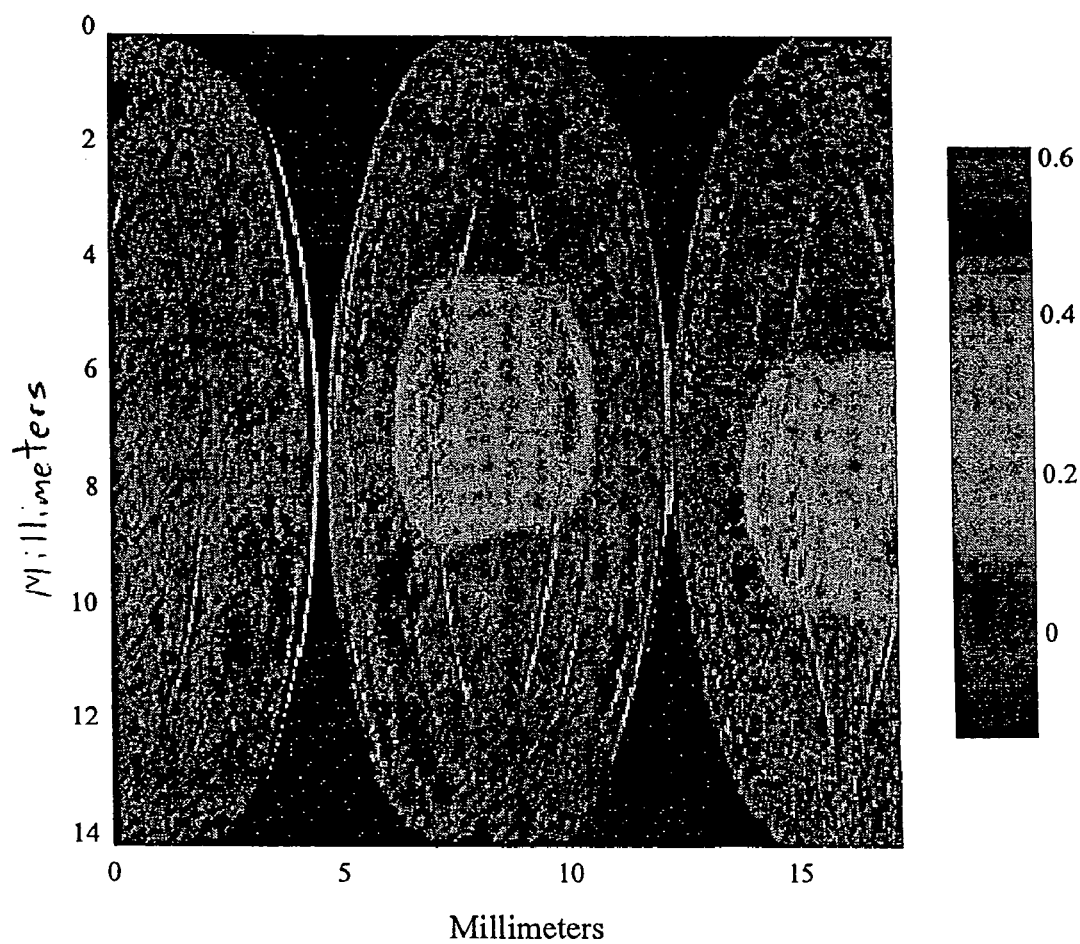
FIG. 7 is a near-infrared chemical image of a carrier tablet with the dose droplet as processed by the pharmaceutical manufacturing machine of FIG. 1.
Figure 7B:
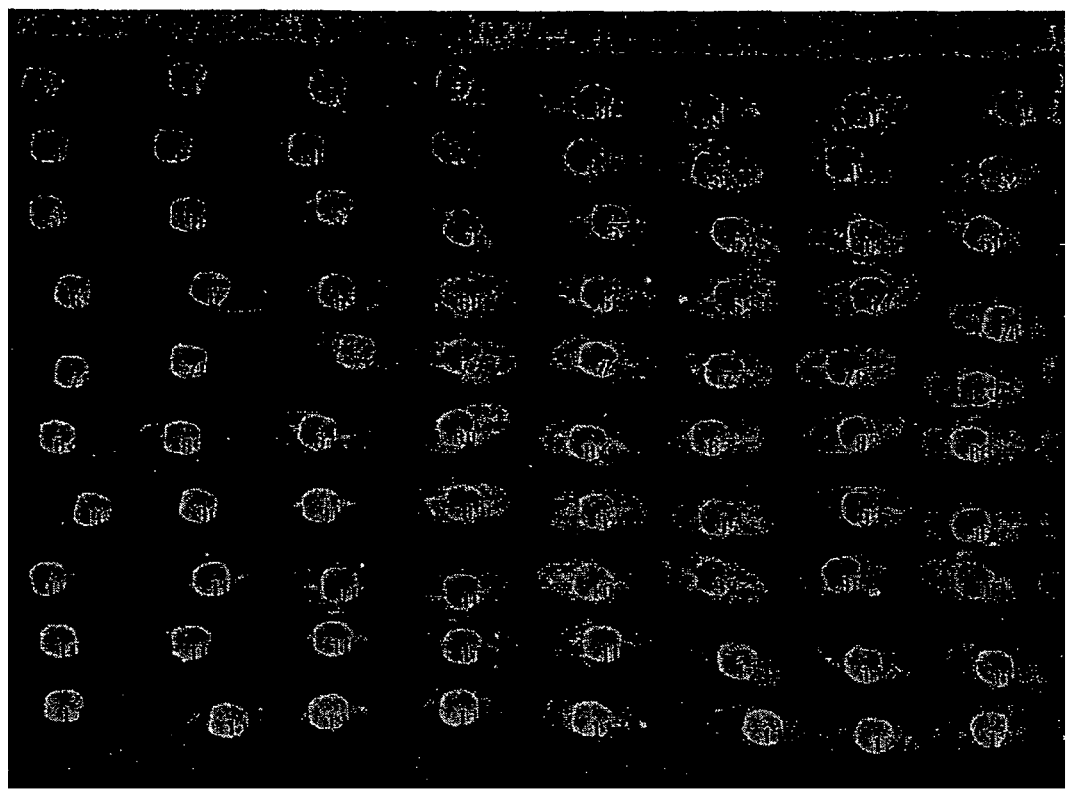
FIG. 7b is a UV induced fluorescence chemical image of a carrier tablet with the dose droplet as processed by the pharmaceutical manufacturing machine of FIG. 1.
Figure 7A:
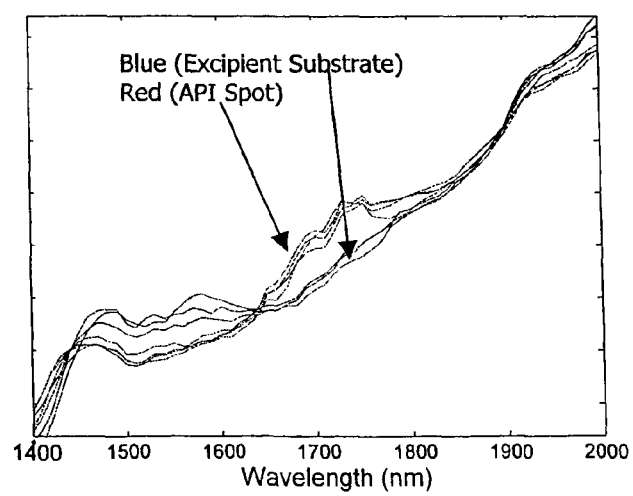
FIG. 7a is an alternative near-infrared chemical image of a carrier tablet with the dose droplet as processed by the pharmaceutical manufacturing machine of FIG. 1.

Dose confirmation step 5350 is performed by the dose confirmation system 500 and provides for real-time monitoring of the position, type, distribution and amount of the liquid dose 2000 that is on the carrier tablet 1000 through use of video images 525 and near-infrared chemical imaging. A sample of results of the NIR chemical imaging method are shown in FIGS. 7 and 7a.

A unique spectrum is collected for each pixel on the focal plane array detector, which results in individual carrier tablet data consisting of both spatially resolved spectra and wavelength dependent images. The output can be seen as a series of spatially resolved spectra (one for each point on the image) or as a series of wavelength resolved images, as shown alternatively in FIGS. 7 and 7*a*. The amount of liquid dose 2000 present on each carrier tablet 1000 can be determined by control system 900 based upon the relative size of the induced image of the liquid dose and the intensity at the individual pixels.

Figures 7C, 7D:
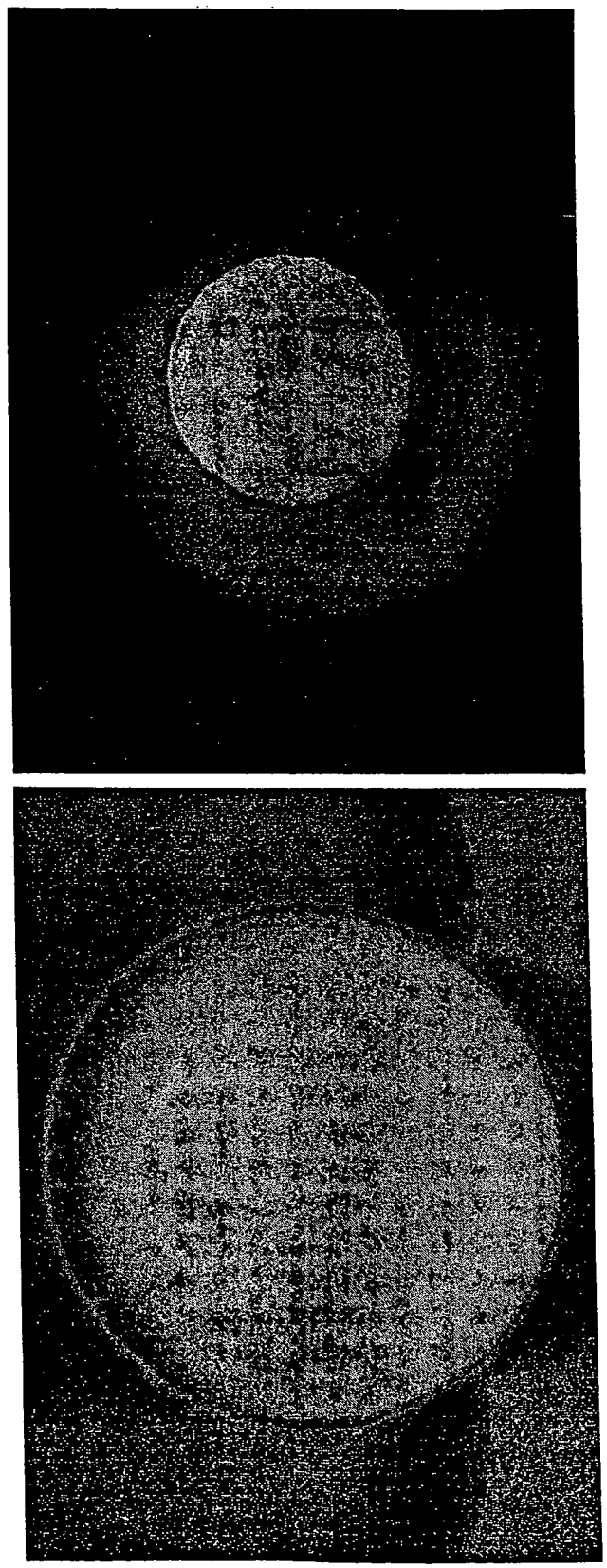
FIG. 7c is a luminescence image of a carrier tablet with only HPC present and no image processing.
FIG. 7d is a luminescence image of a carrier tablet with an active agent and HPC present with image processing.

However, as described above, other methods can be interchanged with the NIR chemical imaging for the analysis of the amount of active agent. For example, FIG. 7*b* shows an image derived from fluorescence where emissions were induced by subjecting the entire holding tray 210 to UV light excitation. A visible spectrum CCD camera was used to image the carrier tablets 1000 and each of their liquid doses 2000. Based upon the area of the liquid doses 2000 and their gray scale intensity at individual pixels, the amount of each liquid dose can be determined by control system 900. FIG. 7*c* shows a luminescence image of a carrier tablet with only HPC present and no image processing, in contrast to FIG. 7*d* which shows a luminescence image of a carrier tablet with an active agent and HPC present with image processing.

The present invention also contemplates the use of the real-time monitoring to provide real-time feedback and adjustment to the conveyor and dispensing systems 300 and 400, such as, for example, adjusting the speed for better positioning of the dose droplet 2100 on the carrier tablet 1000 or adjusting the pump 425 and/or nozzle 450 to increase or decrease the volume of the dose droplet, which increases or decreases the amount of active agent that is ultimately dried on the carrier tablet.

The use of real-time monitoring of the dose droplet 2100 both before and after contact with the carrier tablet 1000, also would allow for more efficient accounting for any losses occurring during the process. For example, but not limited to, if the dose confirmation step 5350 indicated that there is far less dosage present than was indicated by the dose inspection step 5250, the dosing and drying steps 5200 and 5300 can be analyzed and adjusted to account for these losses.

The coating step 5400 is performed by the coating system 600 and provides a coating 2300 over the liquid dose 2000 through use of pad-printing device 610 or other dispensing device. FIG. 5 shows process 5000 in combination with process 8000 for the manufacture of the coating. Process 5000 uses an over coat for the coating 2300 but the coating can be manufactured at other facilities and delivered to machine 10. Also, other processes can be used to manufacture the coating, which are different from the steps shown in process 8000.

The coating drying step 5500 and drying air preparation step 5525 are performed by the coating dryer 630 and provide for drying of the coating 2300 that has been applied over the liquid dose 2000. Similar to the real-time monitoring, feedback and adjustment described above with respect to the drying system 475 of the dispensing system 400, the coating drying step 5500 can provide real-time control of drying of the coating 2300.

The coating inspection step 5550 is performed based on the images 730 obtained by cameras 720 of the printing system 700. Alternatively, a separate image inspection stage, similar to the components and control used by the printing system 700, can be included along machine 10 after the holding trays 210 pass through the coating dryer 630. The coating inspection step 5550 uses real-time monitoring of the coating 2300 applied over the liquid dose 2000 for acceptance or rejection of each of the pharmaceutical product 3000. The present invention also contemplates the use of real-time feedback and adjustment of the coating system 600 and, in particular, the pad-printing device 610 or other dispensing device, such as, for example, adjustment to speed, positioning, quantity and/or pressure.

The printing step 5600 and the dispensing ink step 5625 are performed by the printing system 700 and provide the identification marker on the coating 2300 through use of another pad-printing device or other dispensing device.

The printing inspection step 5650 is also performed based upon the images 730 obtained by the cameras 720 of the printing system 700 and determines the accurate positioning and clarity of the identification marker. The printing inspection step 5650 uses real-time monitoring of the identification marker applied over the coating 2300 for acceptance or rejection of each of the pharmaceutical product 3000. The present invention also contemplates the use of real-time feedback and adjustment of the printing system 700 and, in particular, the pad-printing device 710 or other dispensing device, such as, for example, adjustment to speed, positioning, quantity and/or pressure.

The delivery step 5700 is performed by the acception-rejection system 800 and provides a pharmaceutical product 3000 that is ready for packaging, and which has undergone real-time monitoring, feedback and adjustment to ensure that each of the product meets the required tolerances. Each and every pharmaceutical product 3000 has been designated as either acceptable or rejected, and control system 900 accepts the selected/accepted pharmaceutical product accordingly.

The rejection step 5800 is also performed by the acception-rejection system 800 and rejects those pharmaceutical product 3000 that do not meet the required tolerances based upon the data obtained throughout the process by the real-time monitoring, feedback and adjustment of the machine 10.

Figure 8:
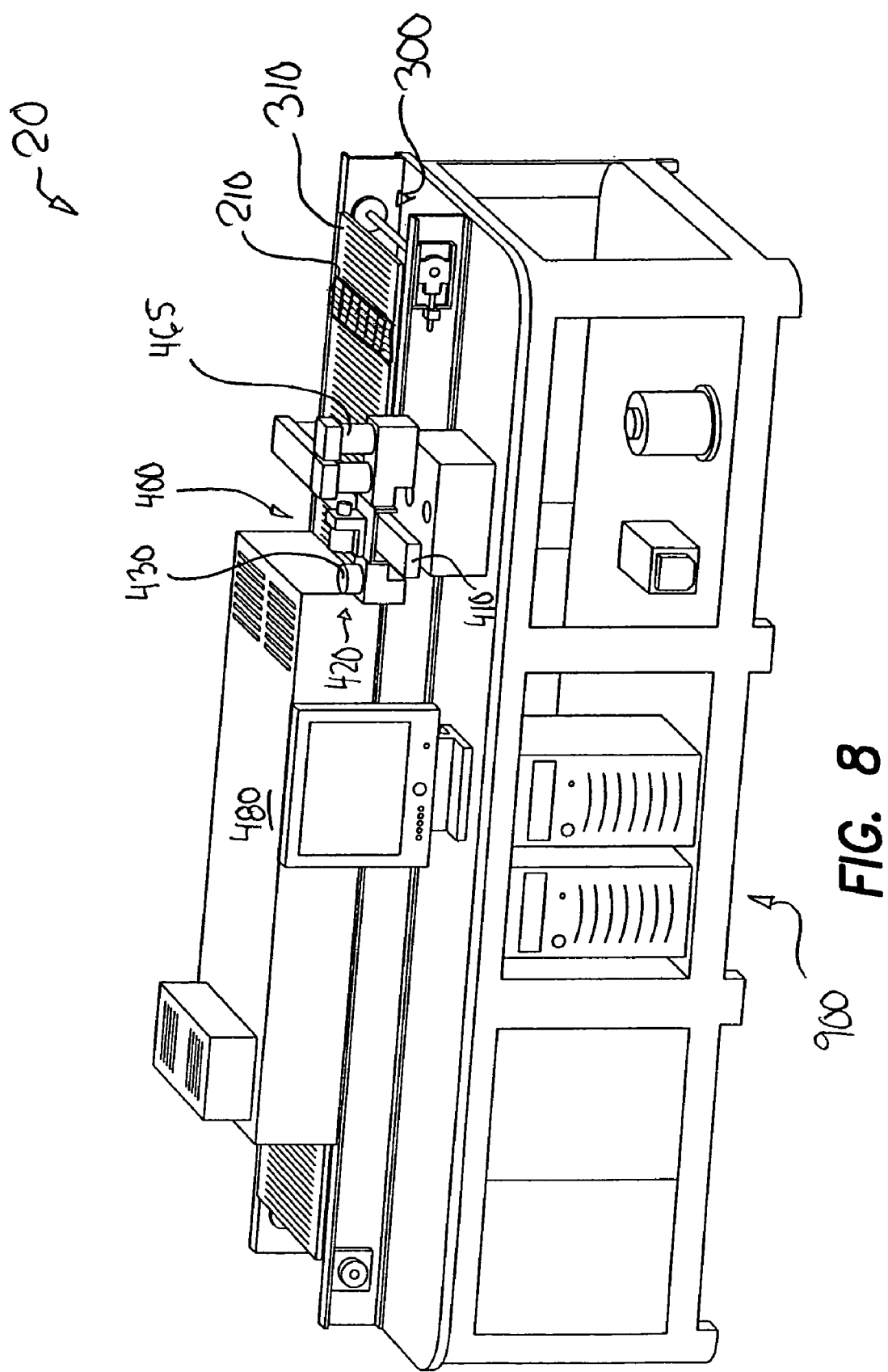
FIG. 8 is a perspective view of an alternative embodiment of a pharmaceutical manufacturing machine of the present invention.
Figure 9:
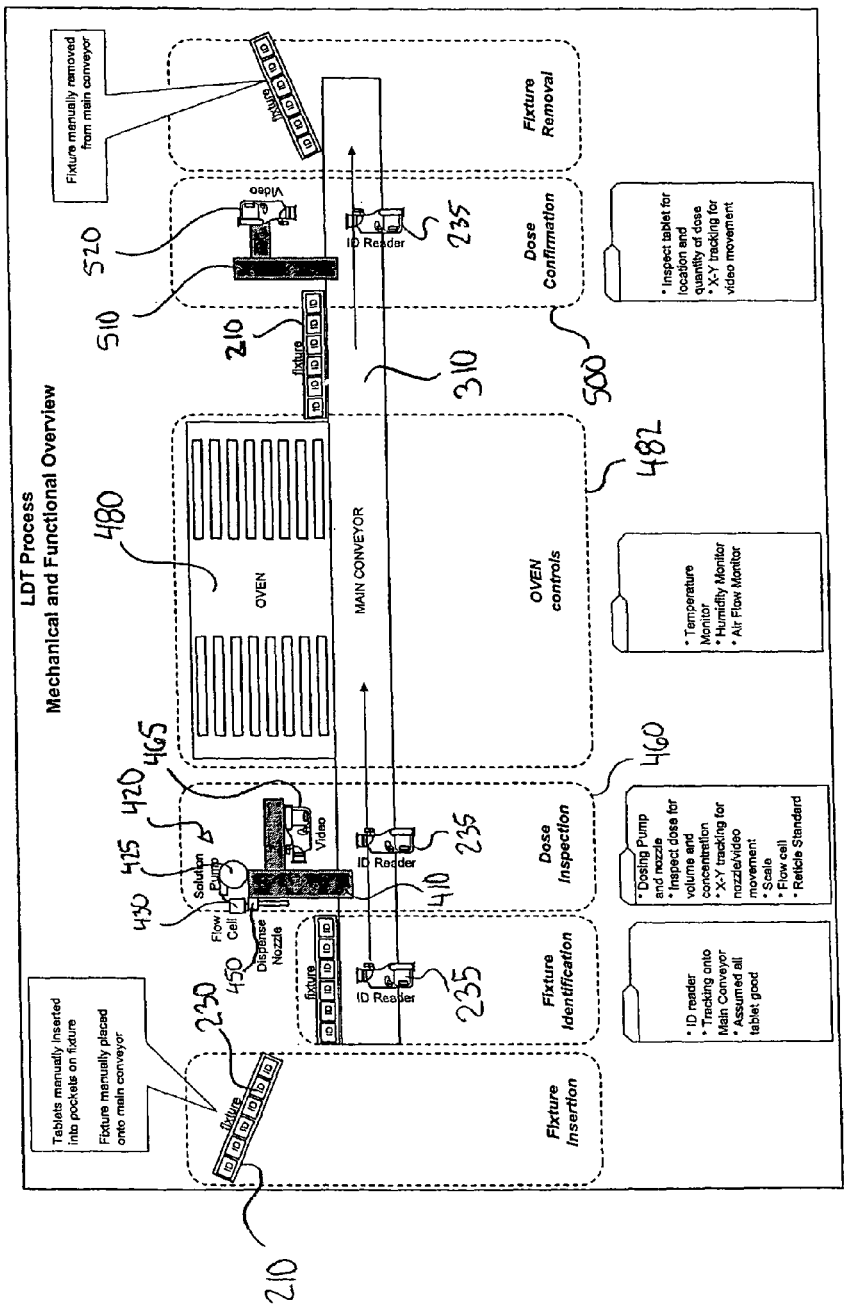
FIG. 9 is a schematic representation of components of the pharmaceutical manufacturing machine of FIG. 8.
Figure 10:
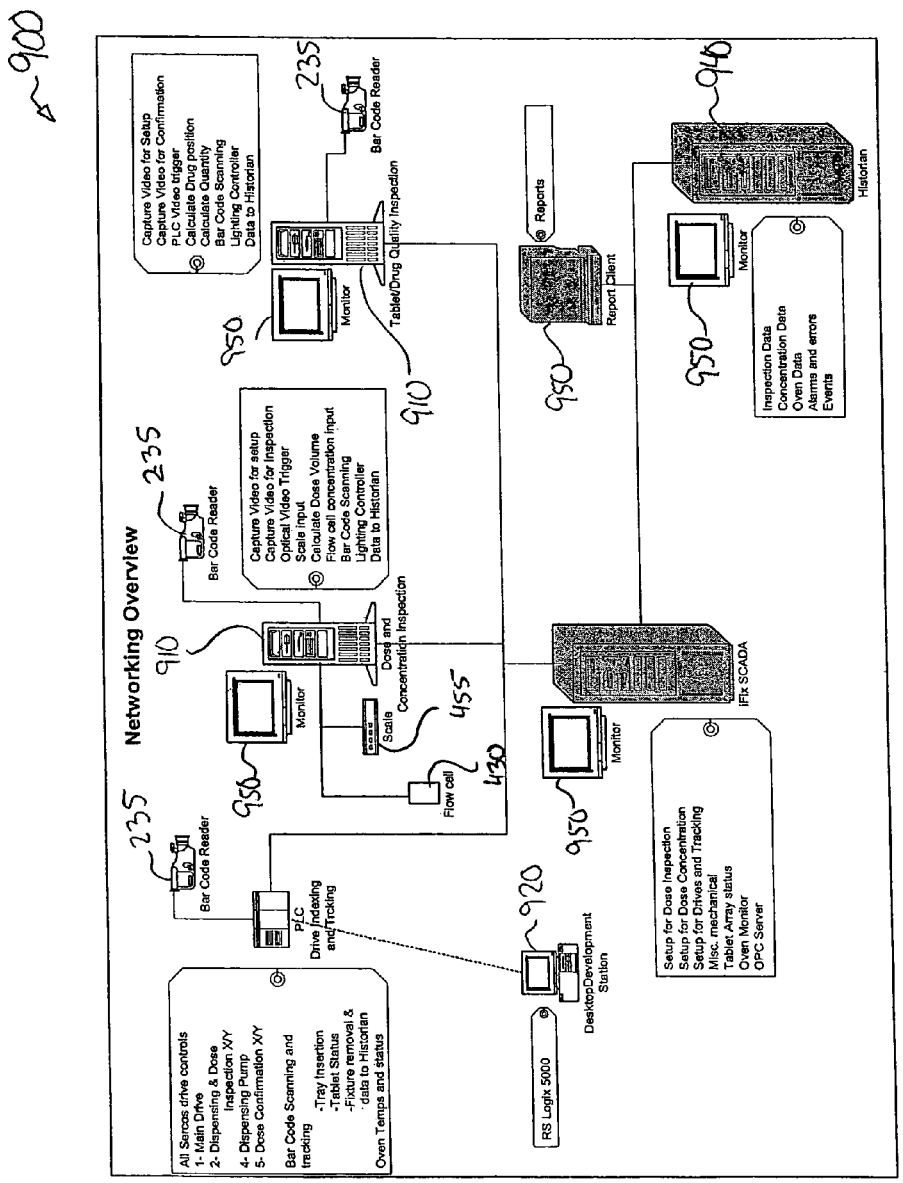
FIG. 10 is a schematic representation of the communication between the components of the pharmaceutical manufacturing machine of FIG. 8.

Referring to FIGS. 8 through 10, another embodiment of a pharmaceutical manufacturing apparatus or machine of the present invention is shown and generally referred to by reference numeral 20. The machine 20 has components that are similar to the components described above with respect to the preferred embodiment of FIG. 1 and are similarly numbered, such as, conveyor system 300, drug dispensing system 400 and control system 900. Machine 20 is a scaled-down version of the preferred embodiment but still provides real-time monitoring for the process. Each of these systems 300, 400 and 900 is operably connected to each other to efficiently and ergonomically provide pharmaceutical product 3000 that have each undergone real-time monitoring, and, preferably, real-time feedback and adjustment.

Holding trays 210 are manually placed on drive conveyor 310 where the carrier tablets 1000 begin their descent through machine 20. Each holding tray 210 is identified through use of the bar code 230 on the tray and a scanner 235. The holding trays 210 continue to move along machine 20 and pass through to the dispensing system 400 where a dispensing module 420, which is mounted to gantry 410, dispenses dose droplets 2100 on each of the carrier tablets 1000. Camera 465 takes an image of each dose droplet being dispensed and, in conjunction with concentration data obtained from flow cell 430, the real-time monitoring of the amount of active agent being dispensed occurs.

After passing through oven 480, where the liquid dose 2000 is dried into a film 2200 on the outer surface 1100 or substantially along the outer surface of the carrier tablet 1000, each of the carrier tablets undergoes real-time monitoring of the position and amount of the liquid dose. Camera 520 (shown in FIG. 9), which is mounted on gantry 510, obtains an image 525 of each of the carrier tablets 1000 and liquid doses 2000 thereon. The images 525 are processed by control system 900 for the location and quantity of the dose.

Under NIR or UV induced fluorescence, camera 520 captures the image 525 of the deposition spot left after dosing and drying. Image analysis software uses gray scale to tabulate the number of pixels and relative intensity of the pixel to develop an image of the dried spot left behind. High doses will give either a greater area of coverage or a higher intensity of gray scale. Based on this information, the dose on the tablet is determined.

The holding tray 210 is then manually removed from the drive conveyor 310. Data has been compiled for each pharmaceutical product 3000 regarding droplet dosage, dose position, quantity of dose, and drying conditions. This data is used by control system 900 to provide a designation for each of the pharmaceuticals as either acceptable or rejected. The machine 20 uses separate scanners 235 at different stages of the machine for identification of the individual carrier tablets 1000.

A second alternative embodiment of the pharmaceutical manufacturing apparatus of the present invention is shown in FIG. 8a and is generally represented by reference numeral 20'. Similar to the embodiment described above with respect to FIGS. 8 through 10, machine 20' is a scaled down version of the preferred embodiment of machine 10 shown in FIG. 1. Machine 20' has many features similar to machines 10 and 20, and such features are similarly numbered, such as, conveyor system 300, and drug dispensing system 400. Machine 20' exemplifies the modularity of the present invention as it includes the features of machine 20 and additionally has gantry 510, which is readily available for connection with dose confirmation system 500.

Figure 8B:
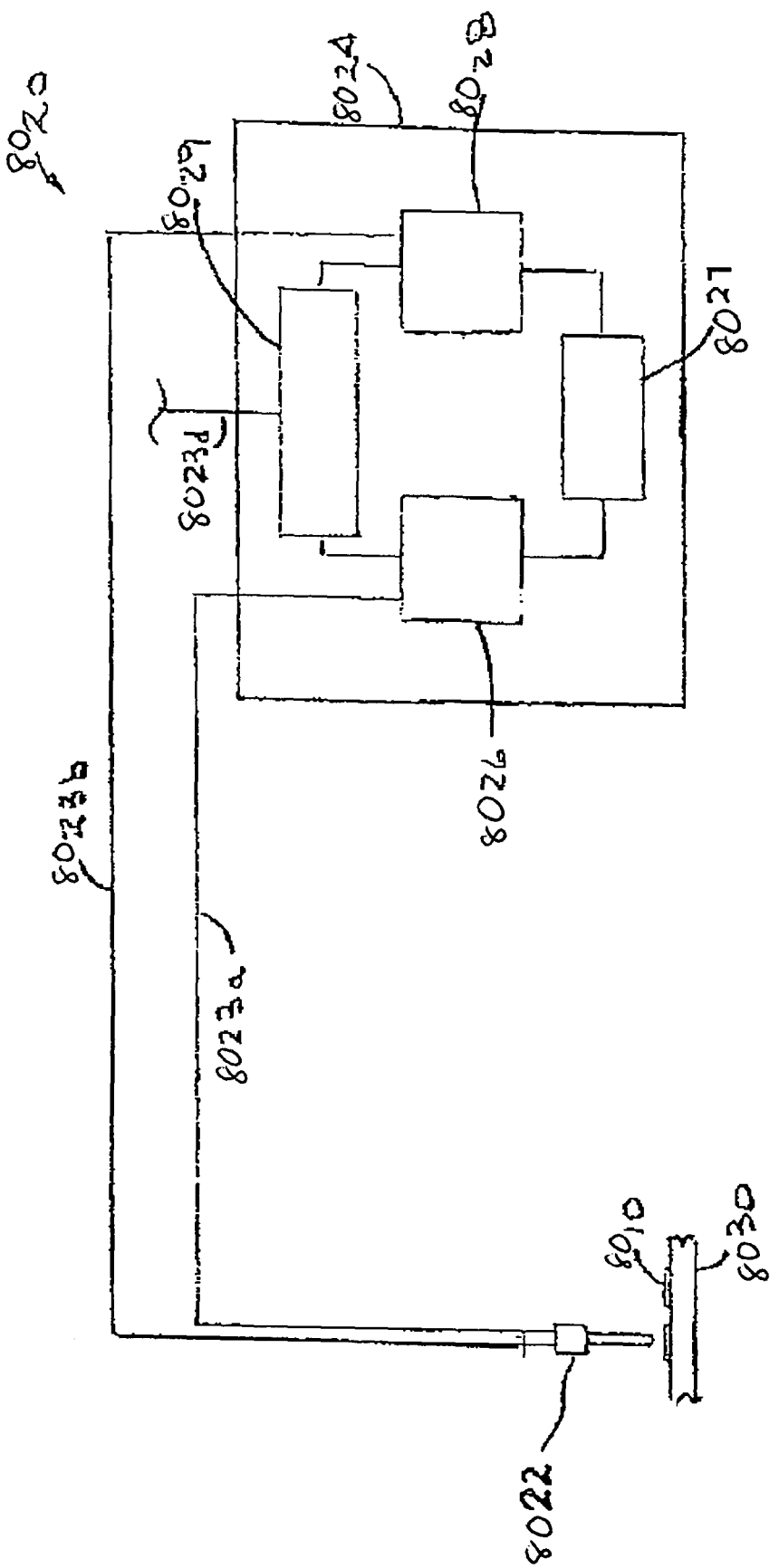
FIG. 8b is a schematic illustration of an alternative embodiment of a spectroscopic detection system.

Referring now to FIGS. 8b through 8o, there is shown a schematic illustration of an alternative exemplary embodiment for a spectroscopic detection system or device, which is generally represented by reference numeral 8020. The spectroscopic detection system 20 generally comprises at least one radiation transmission system 8022 and a first control system 8024. Radiation transmission system 8022 is adapted to provide or transmit incident radiation (e.g., incident radiation pulse) to at least one pharmaceutical sample 8010 and detect the emission radiation emitted from the sample 8010. As illustrated in FIG. 8b, the first control system 24 preferably includes a light source 8026 for providing the desired wavelength of light or incident radiation to the radiation transmission system (or light probe) 8022 via excitation line 8023a, an analyzer 8028 for analyzing the emission radiation detected by the radiation transmission system 8022, which is communicated to the analyzer 8028 via collection line 23b, and storage or memory system 8027 for storing emission characteristics of selected (or desired) actives for subsequent comparison with detected emission radiation from the sample(s) 8010. Preferably, the excitation and collection lines 8023a, 8023b are contained within a single optical line (e.g., fiber optic cable).

Figure 8C:
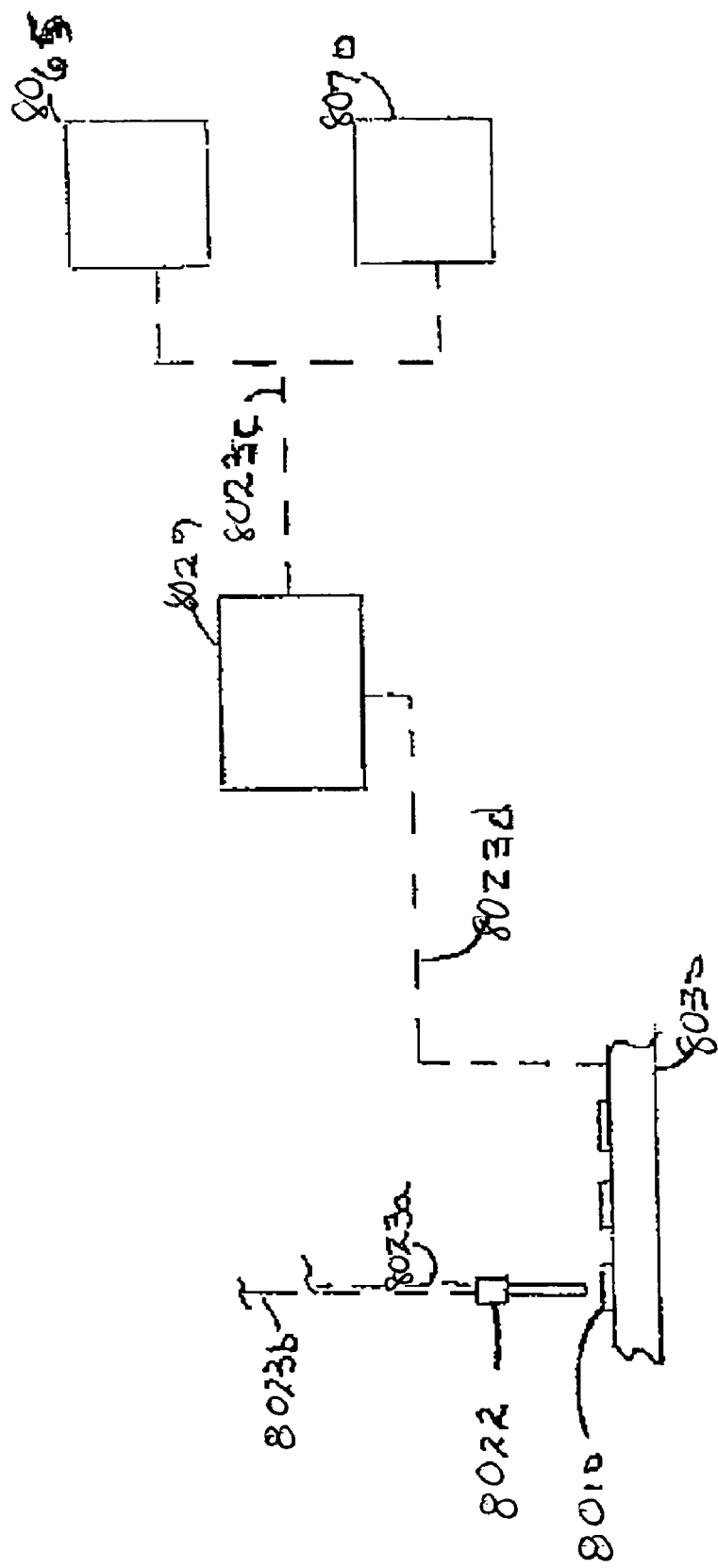
FIG. 8c is a schematic illustration of one of the control devices for the spectroscopic detection system of FIG. 8b.
Figure 8:
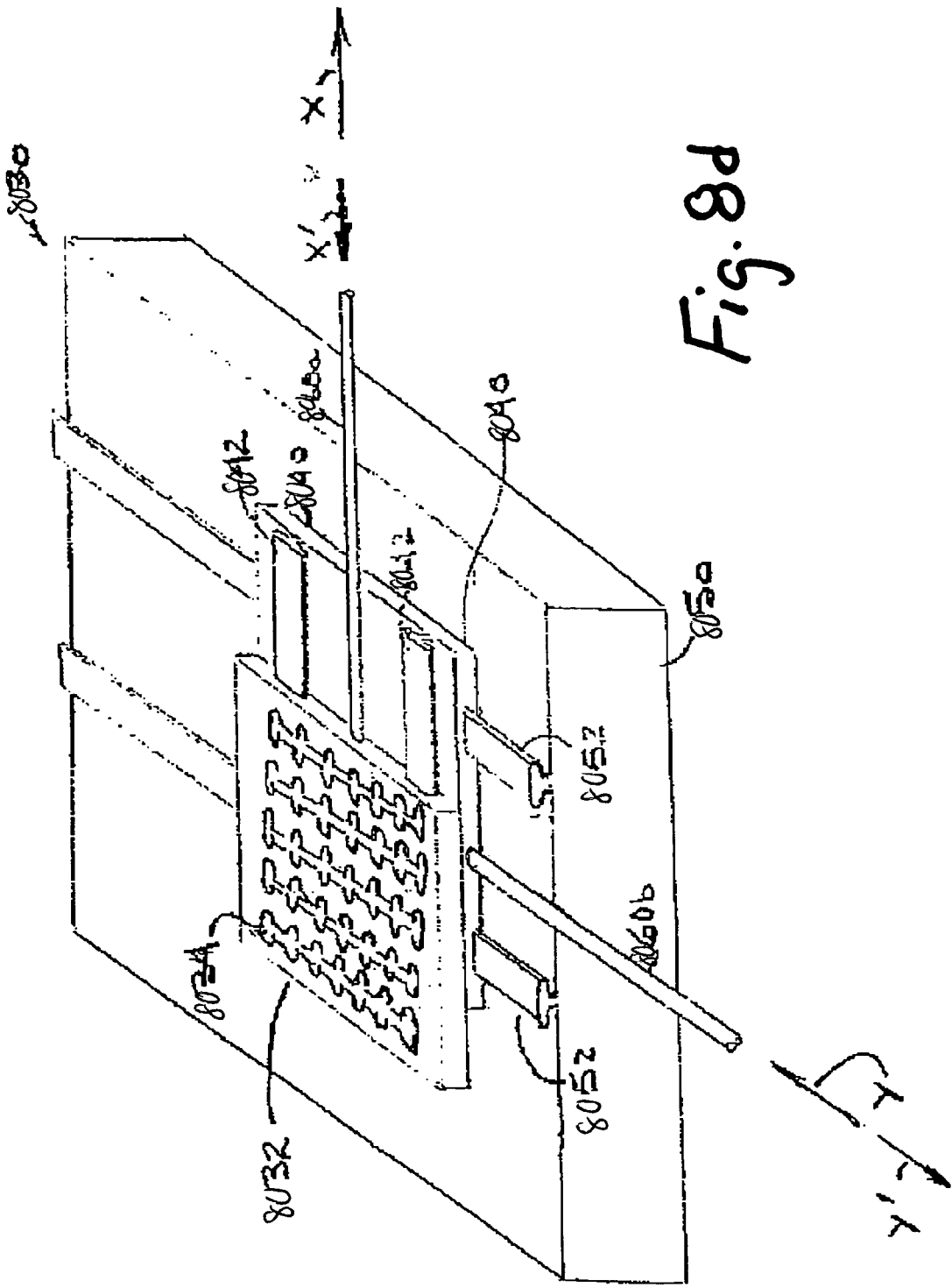

According to this alternative embodiment, the light source 8026 is adapted to generate and provide at least one incident radiation pulse. More preferably, the light source 8026 is adapted to generate and provide a plurality of incident radiation pulses. As discussed in detail below, the spectroscopic detection system 8020 further includes second control (or synchronizing) system 8029 preferably in communication with the first control system 8024 (and, hence, the light source 8026, analyzer 8028 and memory system 8027) and transport system via line 8023d for (i) positioning a respective sample 8010 proximate the light probe 8022 and (ii) synchronizing the movement of the samples 8010 on the transport system 8030 with at least the incident radiation generating system, more preferably, the incident radiation transmission to and detection of the emission radiation from the samples 8010 (see FIG. 8c).

As illustrated in FIG. 8b, the second control system 8029 is preferably a sub-system or component of the first control system 8024. Alternatively, the second control system 8029 is a separate component. Radiation transmission system 8022 can be various types that are employed to effectuate the transmission of light to the pharmaceutical sample(s) 8010 and receipt of emission radiation therefrom, such as, for example, a conventional light probe (e.g., an n-around-1 fiber light probe). Preferably, the incident radiation provided by the light probe 8022 comprises light (or pulse thereof) in the ultraviolet-visible spectral range. The light thus preferably has a wavelength in the range of approximately 200-800 nm. In one alternative embodiment, the light has a wavelength in the range of approximately 225-600 nm. In a further alternative embodiment, the light has a wavelength in the range of approximately 300-450 nm. The wavelength of the light is preferably active specific, i.e., based on the spectral or reflectance characteristics of the selected active agent.

Although the spectroscopic detection system 8020 illustrated in FIG. 8b shows one light probe 8022 and associated excitation and collection lines 8023a, 8023b, it is to be understood that a plurality of light probes and associated lines can readily be employed within the scope of this alternative embodiment. As discussed above, the emission radiation emitted by a pharmaceutical sample (or each of a plurality of pharmaceutical samples) is detected by the radiation transmission system or light probe 8022 and at least a first signal indicative of a respective pharmaceutical sample emission characteristics is communicated to the analyzer 8028. The emission radiation is then compared to the stored emission characteristics of selected actives to determine at least the presence and identity of an active contained in or on a respective sample or the absence of an active in or on a respective sample. The concentration of a detected active can also be determined through known formulations, such as the formulation disclosed in Massart, et al., *Chemomertrics: a Textbook*, Data Handling in Science and Technology, Vol. 2 (1988), which is incorporated by reference herein.

Referring now to FIG. 8d, there is shown an alternative embodiment of a transport system generally designated by reference numeral 8030 that is usable with the spectroscopic detection system 8020. As illustrated in FIG. 8d, the transport system 8030 includes a sample table 8032, a position table 8040 and a base 8050.

Figure 8E:
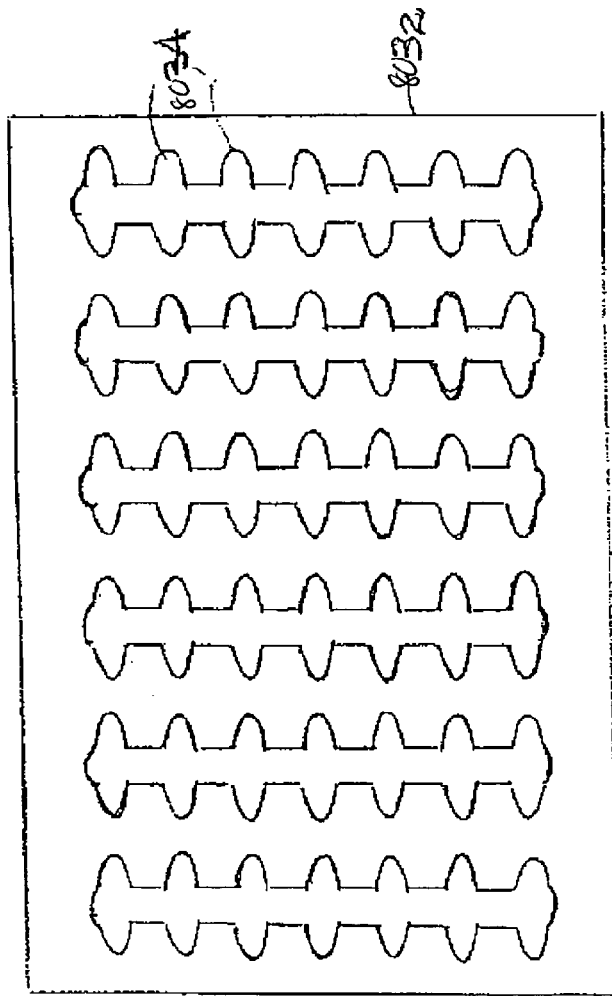
FIG. 8e is a top plan view of the sample table for the spectroscopic detection system of FIG. 8b.
Figure 8G:
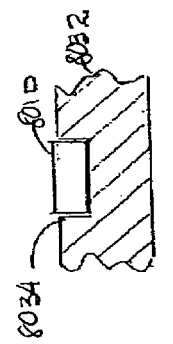
FIG. 8g is a partial section, side plan view of the sample table of FIG. 8e, illustrating the placement of a pharmaceutical sample in one of the sample table receptacles.
Figure 8F:
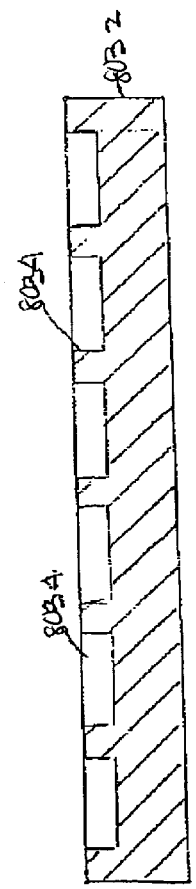
FIG. 8f is a sectioned, side plan view of the sample table of FIG. 8e.
Figure 8H:
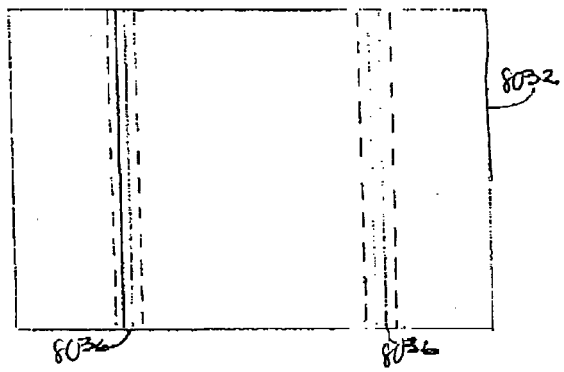
FIG. 8h is a bottom plan view of the sample table of FIG. 8e.
Figure 8I:
FIG. 8i is a partial side plan view of the sample table of FIG. 8e.

Referring now to FIGS. 8e through 8g, the sample table 8032 includes at least one, and more preferably a plurality of, recessed sample receptacles (or holders) 8034 on the top surface with each receptacle 8034 being adapted to receive a respective pharmaceutical sample 8010. Referring to FIGS. 8h and 8i, the sample table 8032 further includes at least two substantially parallel "T-shaped" slots 8036 on the bottom surface that are adapted to slideably receive the position table tracks 8042 (see FIG. 8d).

According to this alternative embodiment, the sample table 8032 can comprise various sizes to accommodate the desired number of receptacles 8034. By way of illustration, in one alternative embodiment, the sample table 8032 has a length of approximately 16 mm a width of approximately 9 mm and includes 200 receptacles 8034. The sample table 8032 is preferably constructed of an inert material, such as Teflon™, stainless steel and coated aluminum, to substantially reduce the possibility of interference with the transmission of light to and emission of light from the samples 8010 contained in the receptacles 8034. In an alternative embodiment, the sample table 8032 comprises a two-piece member, with a lightweight base portion (e.g., aluminum) and a top receptacle portion (having the receptacles 8034 formed on the top surface) constructed of an inert material that is secured on the base portion.

Figure 8J:
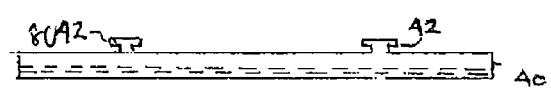
FIG. 8j is a side plan view of the position table for the spectroscopic detection system of FIG. 8b.

Referring now to FIGS. 8*d* and 8*j*, there is shown the position table 8040 of the transport system 8030. As illustrated in FIG. 8*j*, the position table 8040 includes at least two "T-shaped" tracks 8042 that preferably extend across the top surface of the position table 8040. According to this alternative embodiment, the position table tracks 8042 are configured and positioned for slideable entry into and through the sample table slots 8036.

Figure 8K:
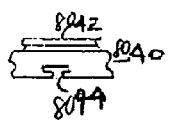
FIG. 8k is a partial front plan view of the position table of FIG. 8j.
Figure 8L:
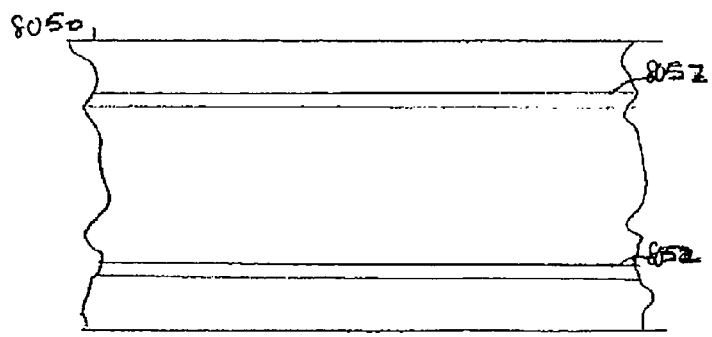
FIG. 8l is a partial top plan view of the transport system base for the spectroscopic detection system of FIG. 8b.
Figure 8M:
FIG. 8m is a partial side plan view of the base of FIG. 8l.

Referring now to FIG. 8*k*, the position table 8040 similarly includes two substantially parallel "T-shaped" slots on the bottom surface that are adapted to slideably receive the base tracks 8052 (see FIGS. 8*d*, 8*l* and 8*m*). The position table 8040 and base 8050 can be constructed out of various lightweight materials, such as aluminum and ABS. Preferably, the position table 8040 and base 8050 are constructed out of aluminum.

Referring now to FIGS. 8*d* and 8*n*, according to the invention, slideable engagement of position table tracks 8042 in sample table slots 8036 effectuates substantially linear movement of the sample table 8032 in the directions denoted by Arrows X and X' (i.e., sample path "SP$_1$"). Slideable engagement of base tracks 8052 in position table slots 8044 effectuates substantially linear movement of the position table 8040 in the directions denoted by Arrows Y and Y' (i.e., sample path "SP$_2$"). As will be appreciated by one having ordinary skill in the art, various conventional system can be employed within the scope of the invention to provide the noted movement of the transport system 8030 and, hence, samples 8010. In a preferred alternative embodiment, a pair of motorized shafts or screws 8060*a*, 8060*b* are provided.

As illustrated in FIG. 8*d*, the first shaft 8060*a* is preferably in communication with the sample table 8032 and provides motive forces in the X' and X directions. The second shaft 8060*d* is preferably in communication with the position table 8040 and provides motive forces in the Y' and Y directions. As will further be appreciated by one having ordinary skill in the art, various alternative transport systems can be employed within the scope of the invention. Such systems include a conventional conveyor, which would provide a single sample path. As indicated above, the spectroscopic detection system 8020 is further adapted to be in synchrony with the transport system 8030 of the invention. In a preferred alternative embodiment, the detection system 8020 includes second control system 8029 that is in communication with the first control system 8024 and transport system 8030. The second control system 8029 is designed and adapted to at least perform the following functions: (i) control the positioning of a sample or samples 8010 by the transport system 8030, (ii) position a respective sample 8010 proximate the light probe 8022 (i.e., illumination position), and (iii) synchronize the movement of the sample or samples 8010 by the transport system 8030 with at least the incident radiation generating system (i.e., light source 8026) of the invention, more preferably, the illumination of and detection of emission radiation from each sample 8010 as it traverses a respective sample path (i.e., SP$_1$, SP$_2$). The noted synchronized sample transport, illumination, detection and analysis is preferably accomplished at a minimum rate (or speed) in the range of 1-5 samples/sec., more preferably, approximately 1 sample/sec. Thus, the method and system of the invention provides high speed, accurate, in-situ analysis of pharmaceutical formulations, and, in particular, drug candidate samples that is unparalleled in the art.

Referring now to FIG. 8*o*, the spectroscopic system 8020 preferably includes a display system to visually display the sample I.D., system and test parameters and, most importantly, the results achieved by virtue of the spectroscopic system and method described above, e.g., the presence, identity and concentration of the active present in a sample. As illustrated in FIG. 8*o*, in one alternative embodiment, the display system comprises at least one monitor 8065 that is in communication with the second control system 8029 and, hence, first control system 8024 via line 8023*c*. In a further alternative embodiment, the display system includes at least one computer system or PC 8070 that includes an associated monitor 8072. As will be appreciated by one having ordinary skill in the art, the computer system 8070 can further be adapted and programmed to provide direct operator control of the first and/or second control system 8024, 8029. In yet a further alternative embodiment, the display system includes at least one monitor 8065 and at least one computer system 8070.

The method for in-situ determination of the presence of an active agent in a pharmaceutical sample in accordance with one alternative embodiment of the invention thus comprises providing at least one pharmaceutical sample, moving the pharmaceutical sample along at least one sample path, generating at least one incident radiation pulse having a wavelength in the range of approximately 200-800 nm, illuminating the pharmaceutical sample with the radiation pulse when the sample is moved proximate the probe 8022 (i.e., illumination position), detecting the emission radiation emitted from the pharmaceutical sample, and comparing the detected emission radiation with stored emission characteristics of selected actives to determine at least the presence or absence of an active.

In a further alternative embodiment, the method for in-situ determination of the presence of an active agent in pharmaceutical samples comprises providing a plurality of pharmaceutical samples, moving the pharmaceutical samples along at least one sample path, generating a plurality of incident radiation pulses, each of the radiation pulses having a wavelength in the range of 200-800 nm, illuminating each of the pharmaceutical samples when moved to an illumination position with at least a respective one of the incident radiation pulses, detecting the emission radiation emitted from each of the pharmaceutical samples, and comparing the emission radiation emitted from each of the pharmaceutical samples with stored emission radiation characteristics of pre-determined actives to determine the presence or absence of the active. In an additional alternative embodiment, the noted method includes the step of synchronizing at least the step of moving the pharmaceutical samples with the step of generating the incident radiation pulses.

Figure 11:
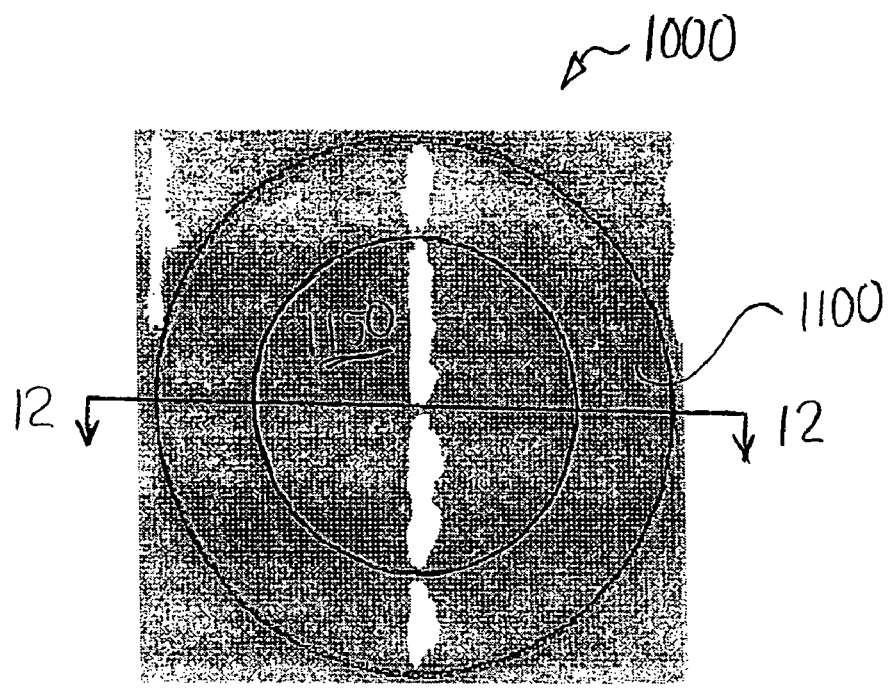
FIG. 11 is a plan view of a preferred embodiment of a carrier tablet of the present invention.

Referring to FIGS. 11 and 12, a first embodiment of the carrier tablet 1000 and the resulting pharmaceutical product 3000, after being processed by machine 10, are shown. The carrier tablet 1000 preferably has a recess or reservoir 1150 disposed centrally along outer surface 1100. Reservoir 1150 provides a basin for the dose droplet 2100 to land after being dispensed to avoid spillage. The reservoir 1150 has a volume that is sufficient to hold the liquid dose 2000. Depending on the viscosity of the liquid dose 2000, the volume of the reservoir 1150 may be less than the volume of the liquid dose (where the viscosity allows the liquid dose to curve above the open end of the reservoir) or may be equal or slightly more than the dose volume.

The reservoir 1150 is preferably smoothly concave to minimize or avoid splashing. However, the present invention contemplates the use of other shapes, sizes and positions for reservoir 1150 to facilitate the dose droplet being added to the carrier tablet 1000. The present invention also contemplates the outer surface 1100 not having any reservoir where the liquid dose 2000 has a high viscosity or there is strong surface tension that prevents the dose from sliding off of the carrier tablet 1000.

The carrier tablets 1000 preferably have reservoirs 1150 formed in both outer surface 1100 and the opposing outer surface 1200. This avoids having to provide the proper orientation of the carrier tablet 1000 during the loading stage. Carrier tablets 1000 can also be pre-coated to prevent absorption so that the film 2200 is maintained on outer surface 1100 or substantially along outer surface 1100. However, for certain liquid doses 2000 and carrier tablets 1000, this may be unnecessary, where there is no absorption by the carrier tablet.

The preferred embodiment of pharmaceutical product 3000 provides the liquid dose on outer surface 1100 or substantially along the outer surface. This prevents the active agent from damaging the structure of the carrier tablet 1000. This also facilitates various methods of real-time monitoring, such as, for example, NIR chemical imaging that has the ability to analyze through some depth but not through the entire carrier tablet. However, the present invention contemplates dispensing the liquid dose 2000 into the matrix of the carrier tablet 1000, where the tablet absorbs the dose but is not de-stabilized, such as an orally disintegrating tablet that is frequently uncoated and has a lesser hardness than that of a conventionally compressed tablet. For active agents that will not damage the structure of the carrier tablet 1000, such as, for example, dissolving of portions of the tablet, this type of dispensing is sufficient. The present invention further contemplates a combination of absorption of the active agent into the matrix of the carrier tablet 1000, while also forming a film on the outer surface of the carrier tablet.

Figure 13:
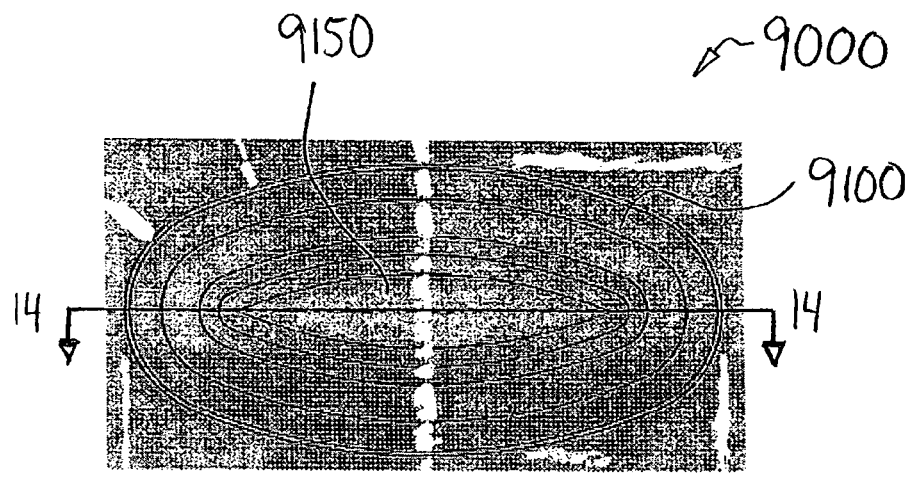
FIG. 13 is a plan view of an alternative embodiment of a carrier tablet of the present invention.
Figure 14:
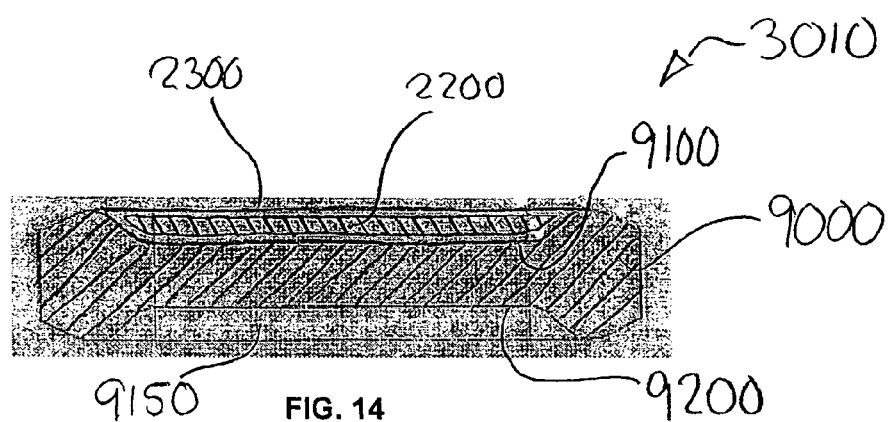
FIG. 14 is a cross-sectional view of the carrier tablet of FIG. 13 taken along line 14-14 of FIG. 13 with a dose droplet.

Referring to FIGS. 13 and 14, a second embodiment of a carrier tablet 9000 and the resulting pharmaceutical product 3010, after being processed by machine 10, are shown. The carrier tablet 9000 preferably has a recess or reservoir 9150 disposed centrally along outer surface 9100. Reservoir 9150 provides a basin for the dose droplet 2100 to land after being dispensed to avoid spillage. Additionally, a second reservoir (not shown) can be used to surround reservoir 9150, which provides a basin for the coating to land after being dispensed to avoid spillage and to provide a more uniform appearance.

It should be understood that alternative sizes and shapes for carrier tablets 1000 and 9000 can also be used. For example, but not limited to, machines 10, 20 and 20' could dispense liquid dose 2000 into gelatin, Hydroxy Propyl Methyl Cellulose (HPMC) or injection molded polymer capsule shells, where the shell is used to hold the dose.

It should further be understood that some of the components and/or systems described with respect to machines 10, 20 and 20' may not need to be utilized for certain pharmaceutical product. For example, but not limited to, pharmaceutical products that are vitamins or cosmetics may not require the same rigorous quality control for all of the criteria as compared to more powerful active agents. In such instances, control system 900 will not apply any unnecessary real-time monitoring activities. Additionally, control system 900 will synchronize the other systems based upon the lack of use of certain systems, which will further maximize the efficiency of the process, such as, for example, where drying of the carrier tablet 1000 and liquid dose 2000 is minimal or not required, the other activities can be greatly sped up.

The present invention contemplates machines 10, 20 and 20', and the various components and systems therein, being modular. This will allow machines 10, 20 and 20' to carry out only the necessary activities for a particular pharmaceutical product 3000 by removing selected unnecessary components, and will provide time saving, such as, for example, avoiding passing holding trays 220 through the coating dryer oven 630 where no coating is being applied.

The present invention contemplates the interchangeability of different components to perform the various activities of machines 10, 20 and 20', such as, for example, probe 530 that performs NIR chemical imaging being interchangeable with other probes that perform other types of analysis, such as, for example, spectroscopy and chemical imaging such as, for example, utilizing Raman, UV reflectance, fluorescence, and/or terahertz. Machines 10, 20 and 20' can utilize the type of analysis, and hence the components that perform that analysis, which are most efficient and accurate for a particular pharmaceutical product 3000. The present invention also contemplates control system 900 indicating which types of analysis and their corresponding components are to be used for a particular pharmaceutical product 3000.

The present invention further contemplates process 5000 including a packaging step so that the end result is a product 3000 that is ready for shipping, especially where real-time release of pharmaceutical product 3000 is utilized. The design and modularity of machines 10, 20 and 20' facilitates the addition of a packaging step to process 5000.

Machines 10, 20 and 20' also provide the ability to change production to a different pharmaceutical product 3000 in a fraction of the time that it takes to make a similar adjustment to a contemporary machine. The cleaning of the machines 10, 20 and 20' for a change of production to a different pharmaceutical product 3000 requires only the cleaning of the dispensing module 420, which can be quickly disassembled. Dispensing modules 420 are relatively low-cost which allows for their replacement rather than a time-consuming repair.

Machines 10, 20 and 20' and process 5000 improve efficiency in manufacturing the pharmaceutical product 3000 based upon the manufacturing steps as well as the quality control steps. The continuity of process 5000 quickly and efficiently provides the product 3000 that are directly ready for packaging, without the need for any quality control testing, e.g., wet chemistry, being performed on them. Also, machines 10, 20 and 20' provide the process 5000 that can be run continuously without the need for stopping as in contemporary devices and techniques.

The real-time monitoring, feedback and adjustment of the present invention avoids unnecessary manufacturing steps (e.g., dispensing on rejected tablets) and provides quality control based on the individual properties of each of the pharmaceutical tablets 3000. The present invention is cost effective because it only discards the defective product 3000 identified by control system 900, rather than discarding all of the product in a batch that has a significant number of defective tablets, as by contemporary methods of product sampling.

Process 5000 is particularly efficient at the production of low dosage pharmaceuticals, e.g., less than 5 mg of active agent. Process 5000 provides for the depositing of precise amounts of the active agent and is thus particularly useful at the lower dosages, e.g., 1 μg to 1000 μg. Although, machines 10, 20 and 20' and process 5000 can produce pharmaceuticals with higher amounts of dosages, e.g., greater than 5 mg, as well as pharmaceutical-like products, such as, for example, vitamins.

The dispensing performed by process 5000 results in a dosage of active agent for the product with a content uniformity for the batch that is preferably less than 5% relative standard deviation (RSD), more preferably less than 3% RSD, and most preferably less than 2% RSD. The accuracy in dispensing of the active agent by process 5000 is over any range of dosage. The advantage of process 5000, and the resulting accuracy of the dispensing, is especially evident at lower dosages compared to contemporary manufacturing processes.

The present invention contemplates the use of coatings and/or additives in combination with the liquid dose 2000 for the purpose of controlling the rate of release of the pharmaceutical product along the Gastro Intestinal (GI) track. As described above, where a plurality of active agents are dispensed onto carrier tablet 1000, such as, for example by layering or on opposing sides of carrier tablet 1000, the release of the different active agents can be controlled to occur at desired areas along the GI track through use of the coatings and/or additives.

The present invention contemplates the use of individual systems or combinations of systems of machines 10, 20 and 20' in combination with other devices, to provide one or more of the steps described in process 5000. For example, but not limited to, dispensing module 420 (including pump 425, flow cell 430 and dispensing head 435) and dose inspection system 460 can be operably connected to a blister filling machine (not shown).

The combination of dispensing module 420 and dose inspection system 460 with the blister filling machine would allow for tablets that are held in the thermoformed pockets of the blister package to receive the liquid dose 2000 from the dispensing module. Similar to the real-time monitoring, feedback and control described above with respect to machines 10, 20 and 20', the positioning of dispensing module 420 with respect to the blister package, and, in particular, each of the tablets, would be adjusted to provide for accurate dispensing.

The combination of dispensing module 420, dose inspection system 460 and the blister filling machine would further provide for quality control assessment of each and every tablet. If one or more of the tablets of a blister package were found to not meet the required tolerances, then the entire blister package would be rejected. Based upon the accuracy of dispensing module 420, which will provide a very low rejection rate of tablets, this would still be a commercially viable process. Alternatively, any tablet that was rejectable would be removed from the blister package and replaced by another tablet that was taken from a reservoir of acceptable tablets.

It should be further understood by one of ordinary skill in the art that the degree of real-time monitoring and/or feedback can be varied depending upon the particular product being manufactured and/or based upon other factors. For example, but not limited to, the machine 10, 20 and 20' may only utilize the high-speed imaging for detection of whether the dose droplet 2100 has accurately been dispensed upon carrier substrate 1000. Preferably the volume calculation of dose inspection system 460 is also utilized to calculate the amount of liquid dose 2000 in the dose droplet 2100. However, the use of contemporary quality control techniques is also contemplated, such as batch sampling. Also, the present invention contemplates the use of contemporary quality control techniques, such as, for example, batch sampling, in parallel with the real-time monitoring and/or feedback described herein for machines 10, 20 and 20'.

It should be further understood by one of ordinary skill in the art that the various devices, techniques and/or systems described herein for machines 10, 20 and 20' can be utilized by themselves or in combination with one or more of the other systems of machines 10, 20 and 20' or in combination with contemporary devices for manufacturing pharmaceutical and pharmaceutical-like product. For example, but not limited to, the high-speed imaging and volume calculation of dose inspection system 460 may be followed by a contemporary batch sampling technique for quality control of the resulting pharmaceutical product 3000.

The video imaging and volume calculation of dose inspection system 460 provides versatile real-time monitoring and feedback control for the pharmaceutical product 3000. This type of quality control is not dependent on the particular formulation of the active agent in the liquid dose 2000, as opposed to some forms of chemical imaging which have such dependency.

The present invention contemplates the use of other techniques for real-time monitoring and/or feedback control for machines 10, 20 and 20' including both contact and non-contact methods. Alternative non-contact monitoring techniques include measurement of change in the capacitance before and after dispensing, measurement of electrical field produced by liquid dose 2000 due to magnetics, and micro-electro-mechanical-systems, such as, for example, utilizing piezo-resistive pressure sensors. An alternative contact monitoring technique includes measurement of the conductance of liquid dose 2000. The present invention contemplates these alternative contact and non-contact techniques being used instead of either or both of the dose inspection system 460 and the dose confirmation system 600, as well as in combination with either or both of the systems, where such alternative techniques are able to appropriately monitor the pharmaceutical product being processed, as desired.

It should also be noted that the terms "first", "second", "third", "fourth", "upper", "lower", and the like, are used herein to modify various elements. These modifiers do not imply a spatial, sequential, or hierarchical order to the modified elements unless specifically stated.

While the present invention has been described with reference to one or more exemplary embodiments, it will be understood by those skilled in the art that various changes may be made and equivalents may be substituted for elements thereof without departing from the scope of the present invention. In addition, many modifications may be made to adapt a particular situation or material to the teachings of the disclosure without departing from the scope thereof. Therefore, it is intended that the present invention not be limited to the particular embodiment(s) disclosed as the best mode contemplated, but that the invention will include all embodiments falling within the scope of the appended claims.

What is claimed is:

1. An apparatus for producing pharmaceutical product, the pharmaceutical product having a carrier substrate and a dosage of active agent, the apparatus comprising:
   a dispensing system for dispensing the dosage of active agent onto the carrier substrate, wherein said dispensing system dispenses the dosage of active agent as a droplet;
   a holding member for holding the carrier substrate;
   a conveyor for moving said holding member along the apparatus;
   a dose inspection system for determining a first amount of the dosage of active agent that is being added to the carrier substrate by said dispensing system, said dose inspection system comprising a camera for obtaining a first image of said dosage of active agent in-flight between said dispensing system and the carrier substrate; and a control system in communication with said dispensing system, said conveyor, and said dose inspection system, wherein said control system controls said conveyor to move said holding member along the apparatus continuously as said dose inspection system determines said first amount of the dosage of active agent.

2. The apparatus of claim 1, wherein said dispensing system comprises a flow cell for determining a concentration of said active agent in said droplet.

3. The apparatus of claim 1, wherein said dose inspection system further comprises a trigger operably connected to said camera, and wherein said trigger actuates said camera to obtain said first image of said droplet in-flight.

4. The apparatus of claim 1, wherein said dose inspection system determines said first amount of the dosage of active agent that is being added to the carrier substrate based at least in part on said first image.

5. The apparatus of claim 1, further comprising a dose confirmation system for determining a second amount of the dosage of active agent after it has been dispensed onto the carrier substrate by said dispensing system, and wherein said dose confirmation system performs spectroscopy on the carrier substrate to determine said second amount of the dosage of active agent.

6. The apparatus of claim 5, wherein said spectroscopy is taken from the group consisting essentially of near infrared, mid-infrared, ultraviolet/visible, fluorescence, laser induced fluorescence, Raman, terahertz, and any combinations thereof.

7. The apparatus of claim 5, wherein said dose confirmation system comprises a second camera for obtaining a second image of the carrier substrate, and wherein said dose confirmation system determines said second amount of the dosage of the active agent on the carrier substrate based on said second image.

8. The apparatus of claim 7, wherein said control system controls said conveyor to move said holding member continuously along the apparatus as said second camera obtains said second image.

9. The apparatus of claim 5, wherein said dose confirmation system comprises a second camera for obtaining a second image of the carrier substrate, and wherein said dose confirmation system determines a position of the dosage of active agent on the carrier substrate based on said second image.

10. The apparatus of claim 1, further comprising a drying system with drying monitors, wherein said drying system dries the dosage of active agent on the carrier substrate and said drying monitors obtain drying conditions for the carrier substrate.

11. The apparatus of claim 10, wherein said drying conditions are taken from the group consisting essentially of temperature, air-flow rate, humidity, radiation, product surface temperature, and any combinations thereof.

12. The apparatus of claim 1, further comprising a printing system for applying an identification marker to the carrier substrate, and a second camera for obtaining a second image of said identification marker for inspection.

13. The apparatus of claim 12, wherein said control system controls said conveyor to move said holding member continuously along the apparatus as said second camera obtains said second image.

14. The apparatus of claim 1, further comprising a second camera, wherein said second camera obtains a second image of the carrier substrate for inspection, and wherein said second image is obtained prior to said dispensing system adding the dosage of active agent to the carrier substrate.

15. The apparatus of claim 1, wherein said control system further controls said dispensing system to move continuously with respect to the carrier substrate as it dispenses the dosage, and as said conveyor moves said holding member along the apparatus.

16. A monitoring system for a pharmaceutical machine that produces pharmaceutical product, the pharmaceutical product comprising a carrier substrate and a dosage of active agent, the system comprising:

a dose inspection system operably connected to the pharmaceutical machine, said dose inspection system determining an amount of the dosage of active agent that is being added to the carrier substrate by the pharmaceutical machine; and a control system in communication with said dose inspection system and said pharmaceutical machine, wherein said pharmaceutical machine dispenses a droplet of the dosage of active agent onto the carrier substrate, wherein said dose inspection system obtains an image of said droplet in-flight, and wherein said dose inspection system determines said amount of the dosage of active agent that is being added to the carrier substrate based at least in part on said image, and wherein said control system controls said pharmaceutical machine to move the carrier substrate along the pharmaceutical machine continuously as said dose inspection system obtains said image.

17. The system of claim 16, wherein said dose inspection system comprises a camera, a flow cell, and a trigger, wherein said trigger is operably connected to said video camera, and wherein said trigger actuates said video camera to obtain said image of said droplet in-flight.

18. An apparatus for producing pharmaceutical product, the pharmaceutical product comprising a carrier substrate and a dosage of active agent, the apparatus comprising:

a dispensing system that adds the dosage of active agent to the carrier substrate;

a holding member for holding the carrier substrate;

a conveyor for moving said holding member along the apparatus;

a dose inspection system that performs real-time monitoring of said dispensing system to determine an amount of the dosage of active agent that is being added to said carrier substrate by said dispensing system, said dose inspection system comprising a camera for obtaining a first image of said dosage of active agent in-flight between said dispensing system and said carrier substrate; and a control system in communication with said dispensing system, said conveyor, and said dose inspection system, wherein said control system controls said conveyor to move said holding member continually continuously along the apparatus as said dose inspection system determines said first amount of the dosage of active agent.

19. The apparatus of claim 18, wherein said control system performs real-time control of said dispensing system based at least in part on said real-time monitoring.

20. The apparatus of claim 19, wherein said real-time control comprises adjusting said amount of the dosage of active agent that is being added to each of the carrier substrate.

21. The apparatus of claim 19, wherein said real-time control comprises adjusting a position of the dosage of active agent added to each of the carrier substrate.

22. A method of providing quality control for a pharmaceutical machine comprising:

obtaining an image of a droplet of a dosage of active agent that is being added to a carrier substrate that is processed by the pharmaceutical machine;

determining said amount of said dosage of active agent that is being added to said carrier substrate based at least in part on said image; and controlling said carrier substrate to move along the pharmaceutical machine continuously as said image is obtained, wherein said image is taken in-flight.

* * * * *